US005976545A

United States Patent [19]
Harris et al.

[11] Patent Number: 5,976,545
[45] Date of Patent: Nov. 2, 1999

[54] ZPC POLYPEPTIDES

[75] Inventors: Jeffrey D. Harris; Kuang T. Hsu; Joseph S. Podolski, all of The Woodlands, Tex.

[73] Assignee: Zonagen, Inc., The Woodlands, Tex.

[21] Appl. No.: 08/484,158

[22] Filed: Jun. 7, 1995

Related U.S. Application Data

[60] Division of application No. 08/149,223, Nov. 9, 1993, which is a continuation-in-part of application No. 08/012,990, Jan. 29, 1993, abandoned, which is a continuation-in-part of application No. 07/973,341, Nov. 9, 1992, abandoned.

[51] Int. Cl.$^6$ ..................................................... A61K 39/00
[52] U.S. Cl. .................................... 424/192.1; 424/184.1; 424/185.1; 424/193.1; 530/350; 530/395; 530/326; 514/14
[58] Field of Search .................................... 530/350, 345, 530/326; 424/184.1, 192.1, 185.1, 193.1; 514/14

[56] References Cited

U.S. PATENT DOCUMENTS

| 4,996,297 | 2/1991 | Dunbar | 530/395 |
| 5,641,487 | 6/1997 | Dean et al. | 424/184.1 |
| 5,820,863 | 10/1998 | Dunbar | 424/185.1 |

FOREIGN PATENT DOCUMENTS

| WO 90/15624 | 12/1990 | WIPO . |
| WO 92/03548 | 3/1992 | WIPO . |

OTHER PUBLICATIONS

Colman et al. Research in Immunology. vol. 145: 33–36, 1994.
Chamberlin et al. P.N.A.S. vol. 87: 6014–6018, 1990.
Aitken et al., "Immunization against Zona Pellucida Antigens," *Immunological Aspects of Reproduction and Fertility Control*, Hearn, J., (ed.), MTP Press. Ltd. (1980).
Aitken et al., "The Influence of Anti–zona and Anti–sperm Antibodies on Sperm–egg Interactions," *J. Reprod. Fert.*, 62:597–606 (1981).
Bleil et al., "Identification of a Secondary Sperm Receptor in the Mouse Egg Zona Pellucida: Role in Maintenance of Binding of Acrosome–Reacted Sperm to Eggs," *Developmental Biology*, 128:276–385 (1988).
Bleil et al., "Mammalian Sperm–Egg Interaction: Identification of Glycoprotein in Mouse Egg Zonae Pellucidae Possessing Receptor Activity for Sperm," *Cell*, 20:873–882 (1980).
Bleil et al., "Structure and Function of the Zona Pellucida: Identification and Characterization of the Proteins of the Mouse Oocyte's Zona Pellucida," *Developmental Biology*, 76:185–202 (1980).
Chamberlin et al., "Genomic Organization of a Sex Specific Gene: The Primary Sperm Receptor of the Mouse Zona Pellucida," *Developmental Biology*, 131:207–214 (1989).

Chamberlin et al., "Human Homolog of the Mouse Sperm Receptor," *Developmental Biology*, 87:6014–6018 (1990).
Dunbar et al., "Proteolysis of Specific Porcine Zona Pellucida Glycoproteins by Boar Acrosin," *Biology of Reproduction*, 32:619–630 (1985).
Dunbar et al., "Identification of the Three Major Proteins of Porcine and Rabbit Zonae Pellucidae by High Resolution Two–Dimensional Gel Electrophoresis: Comparison with Serum, Follicular Fluid, and Ovarian Cell Proteins," *Biology of Reproduction*, 24:1111–1124 (1981).
Hedrick et al., "Isolation of the Zona Pellucida and Purification of Its Glycoprotein Families from Pig Oocytes," *Analytical Biochemistry*, 157:63–70 (1986).
Hedrick et al., "On the Macromolecular Composition of the Zona Pellucida from Porcine Oocytes," *Developmental Biology*, 121:478–488 (1987).
Jones et al., "Histology of Ovaries of Female Rabbits Immunized with Deglycosylated Zona Pellucida Macromolecules of Pigs," *J. Reprod. Fert.*, 95:513–525 (1992).
Keenan et al., "Endocrine Response in Rabbits Immunized with Native versus Deglycosylated Porcine Zona Pellucida Antigens," *Biology of Reproduction*, 44:150–156 (1991).
Kinloch et al., "Primary Structure of the Mouse Sperm Receptor Polypeptide Determined by Genomic Cloning," *Proc. Natl. Acad. Sci., USA*, 85:6409–6413 (1988).
Kinloch et al., "Genomic Organization and Polypeptide Primary Structure of Zona Pellucida Glycoprotein hZP3, the Hamster Sperm Receptor," *Developmental Biology*, 142:414–421 (1990).
Liang et al., "Oocyte–Specific Expression of Mouse Zp–2: Developmental Regulation of the Zona Pellucida Genes," *Molecular and Cellular Biology*, 10(4):1507–1515 (1990).
Mahi–Brown et al., "Fertility Control in the Bitch by Active Immunization with Porcine Zonae Pellucidae: Use of Different Adjuvants and Patterns of Estradiol and Progesterone Levels in Estrous Cycles," *Biology of Reproduction*, 32:761–722 (1985).
Maresh et al., "Antigenic Comparison of Five Species of Mammalian Zonae Pellucidae," *The Journal of Experimental Zoology*, 244:299–307 (1987).
Millar et al., "Vaccination with Synthetic Zona Pellucida Peptide Produces Long–Term Contraception in Female Mice," *Science*, 246:935–938 (1989).
Ringuette et al., "Molecular Analysis of cDNA Coding for ZP3, a Sperm Binding Protein of the Mouse Zona Pellucida," *Developmental Biology*, 127:287–295 (1988).

(List continued on next page.)

*Primary Examiner*—Christina Y. Chan
*Assistant Examiner*—Patrick J. Nolan
*Attorney, Agent, or Firm*—Marshall, O'Toole, Gerstein, Murray & Borun

[57] ABSTRACT

A method for specifically inducing transient infertility or permanent sterility in a host animal by selective vaccination with specific zona pellucida proteins or immunocontraceptively active fragments thereof. Novel zona pellucida DNA sequences encoding specific zona pellucida proteins are disclosed.

16 Claims, 6 Drawing Sheets

OTHER PUBLICATIONS

Ringuette et al., "Oocyte–specific Gene Expression: Molecular Characterization of a cDNA Coding for ZP–3, the Sperm Receptor of the Mouse Zona Pellucida," *Proc. Natl. Acad. Sci., USA,* 83:4341–4345 (1986).

Sacco et al., "Application of a Radioimmunoassay (RIA) for Monitoring Immune Response to Porcine Zonae Pellucidae," *Proceedings of the Society for Experimental Biology and Medicine,* 167:318–326 (1981).

Sacco et al., "Carbohydrate Influences the Immunogenic and Antigenic Characteristics of the ZP3 Macromolecule ($M_r$ 55 000) of the Pig Zona Pellucida," *J. Reprod. Fert.,* 76:575–586 (1986).

Schwoebel et al., "Isolation and Characterization of Full–length cDNA Encoding the 55–kDa Rabbit Zona Pellucida Protein," *The Journal of Biological Chemistry.,* 266(11):7214–7219 (1991).

Skinner et al., Species Variation in the Zona Pellucida *Immunological Approaches to Contraception and to Promotion of Fertility,* GP Talwor, (Ed.), Plenum:New York, pp. 251–268 (1986).

Subramanian et al., "Specific Radioimmunoassay for the Detection of a Purified Porcine Zona Pellucida Antigen (PPZA)," *Biology of Reproduction,* 24:933–943 (1981).

Timmons et al., "Use of Specific Monoclonal and Polyclonal Antibodies to Define Distinct Antigens of the Porcine Zonae Pellucidae," *Biology of Reproduction,* 36:1275–1287 (1987).

Timmons et al., "Perspectives in Immunoproduction: Conception and Contraception," Mathur, S. and Fredericks, C.M., (eds.), Hemisphere Publishing Co., New York, pp. 242–260 (1988).

Wassarman, "Zona Pellucida Glycoproteins," *Ann. Rev. Biochem.,* 57:415–442 (1988).

Wolgemuth et al., "Formation of the Rabbit Zona Pellucida and Its Relationship to Ovarian Follicular Development," *Developmental Biology,* 106:1–14 (1984).

Yurewicz et al., "Isolation and Preliminary Characterization of a Purified Pig Zona Antigen (PPZA) from Porcine Oocytes," *Biology of Reproduction,* 29:511–523 (1983).

Yurewicz et al., "Nucleotide Sequence of cDNA Encoding ZP3α, a Sperm–binding Glycoprotein from Zona Pellucida of Pig Oocyte," *Biochimica et Biophysica Acta.,* 1174:211–214 (1993).

Yurewicz et al., "Structural Characterization of the Mr= 55,000 Antigen (ZP3) of Porcine Oocyte Zona Pellucida," *The Journal of Biological Chemistry,* 262(2):564–571 (1987).

Chamow and Dean, "Anti–Zona Pellucida Antibodies in Mice Immunized With Recombinant ZP3–β–Galactosidase Fusion Protein," *Fed. Proc.,* 46(6):2015 (1988).

East, I.J., "Scintigraphy of Normal Mouse Ovaries with Monoclonal Antibodies to ZP–2, the Major Zona Pellucida Protein," *Science,* 225:938–941 (Aug. 31, 1984).

Lou and Tung, "T Cell Peptide of a Self–Protein Elicits Autoantibody to the Protein Antigen," *J. of Immunology,* 151:5790–5798 (1993).

Paterson et al., "Analysis of the Contraceptive Potential of Antibodies against Native and Deglycosylated Porcine ZP3 in Vivo and in Vitro," *Biol. Reprod.,* 46(4):523–534 (Apr., 1992).

Rhim et al., "Autoimmune Disease of the Ovary Induced by a ZP3 Peptide from the Mouse Zona Pellucida," *J. Clin. Invest.,* 89:28–35 (Jan., 1992).

Tung et al., "Autoimmune Disease of the Ovary: a Mechanism of Premature Ovarian Failure and a Complication of ZP3 Contraceptive Vaccine," *Reprod. Immunol.,* 97:169–179 (1993).

Chamberlin and Dean, "Human Homolog of the Mouse Sperm Receptor," *Proc. Nat'l Acad. Sci., USA,* 87:6014–6018 (Aug., 1990).

Koyama et al., "Blocking of Human Sperm–Zona Interaction by Monoclonal Antibodies to a Glycoprotein Family (ZP4) of Porcine Zona Pellucida," *Biology of Reproduction,* 45:727–735 (1991).

Liu et al., "Contraception in Mares Heteroimmunized with Pig Zonae Pellucidae," *J. Reprod. Fert.,* 85:19–29 (1989).

Henderson et al., "Contraceptive Potential of Antibodies to the Zona Pellucida," *J. Reprod. Fert.,* 83:325–343 (1988).

Chamow et al. (1987) Fed Proc 46(6):2015.

Keenan et al. (1991) Biology of Reproduction vol. 44(1): 150–6.

ID POLYPEPTIDES

CROSS REFERENCE TO RELATED APPLICATION

This is a divisional of application Ser. No. 08/149,223 filed Nov. 9, 1993, pending which is a continuation-in-part of U.S. application Ser. No. 08/012,990, filed Jan. 29, 1993, now abandoned which is a continuation-in-part of U.S. application Ser. No. 07/973,341, now abandoned filed on Nov. 9, 1992.

FIELD OF THE INVENTION

This invention relates generally to the production and use of zona pellucida proteins, and more particularly to novel DNA sequences encoding zona pellucida proteins, to recombinant materials and methods for producing such proteins and to materials and methods for selectively effecting either transient infertility or permanent sterility in mammals through use of naturally occurring and recombinant zona pellucida proteins.

BACKGROUND OF THE INVENTION

The present invention relates to a method for inducing reproducible transient infertility or sterility in a mammal by inducing in that mammal antibodies directed to proteins found in the zona pellucida of that mammal's oocytes. The invention also relates to purified, isolated DNA sequences encoding the zona pellucida proteins herein designated "ZPA" and "ZPB" and "ZPC" from various mammalian species. The invention is further directed to pharmaceutical compositions capable of inducing antibody production in a subject mammal.

The zona pellucida (ZP) is a complex matrix surrounding the mammalian oocyte, formed of glycoproteins secreted by ovarian cells. Zona pellucida glycoproteins perform a variety of functions. For example, the mouse ZP proteins previously designated ZP2 and ZP3 are complexed into long filaments which are cross-linked by the protein designated ZP1 in the ZP matrix providing structural integrity to the matrix. Wassarman, P. M., *Annu. Rev. Biochem.* 57:415–442 (1988). In addition to its structural role, mouse ZP3 has been shown to be a sperm receptor in the ZP matrix. Bleil, J. P. and Wassarman, P. M., *Cell* 20: 873–882 (1980). Following binding of sperm to ZP3 and the subsequent induction of the sperm acrosome reaction on the surface of the ZP, ZP2 acts as a secondary sperm receptor that is necessary for the maintenance of sperm binding to the egg. Bleil et al., *Dev. Biol.* 128: 376–385 (1988). Because of its role in the maintenance of the oocyte and in sperm-oocyte interactions, the ZP represents a logical target for design of contraceptive agents which interfere with the fertilization process.

Various groups have undertaken an immunological approach in attempts to interfere with ZP functions and thus to decrease fertility in immunized animals. See, Dunbar et al. In: *International Congress on Reproductive Immunology*. T. Wegman and T. Gills (eds.). London: Oxford Press, pp. 505–528 (1983); and Dunbar et al. In: *Mechanisms and Control of Animal Fertilization*. J. Hartman (ed.) Academic Press, New York, pp. 139–166 (1983). These studies showed that active immunization of mammals with ovarian homogenates decreased fertility. However, the large number of components in such homogenates made the identification of antigens responsible for the decrease in fertility nearly impossible. In addition, the use of such a complex mixture creates a potential for unwanted and potentially harmful side-effects.

Research by various investigators using chromatographic methods including SDS polyacrylamide gel electrophoresis (PAGE) and high pressure liquid chromatography (HPLC) have resulted in the identification of numerous zona pellucida proteins from a variety of mammalian species. Data compiled by Timmons and Dunbar in "*Perspectives in Immunoreproduction: Conception and Contraception*", pp. 242–260, Mathur, S. and Fredericks, C. M. eds.; New York, Hemisphere Publishing Co (1988), as described below, illustrate examples of zona pellucida proteins that have been characterized.

Zona pellucida proteins isolated from pig include: PZI, a 40–110 kD protein isolated by Dunbar et al., *Biol. Reprod.* 24:1111 (1981); PZII, a 70–110 kD protein, PZIII, a 95–118 kD protein, and PZIV, an 18–25 kD protein, all isolated by Dunbar et al., *Biol. Reprod.* 32:619 (1985); 90K, a 89–119 kD protein, 65K, a 61–83 kD protein, 55K, a 47–66 kD protein, and 25K, an 18–26 kD protein, all isolated by Hedrick, J. L. and Wardrip, N. J. *Biochem.* 157: 63 (1986); ZP1, an 82–118 kD protein, ZP2, a 58–96 kD protein, ZP3 (PPZA), a 40–74 kD protein, and ZP4, a 21 kD protein, all isolated by Subramanian et al., *Biol. Reprod.* 24:933 (1981); 87K (ZP1/ZP2), a 77–97 kD protein, 58K, a 40–70 kD protein both isolated by Yurewicz et al., *Biol. Reprod.* 29: 511 (1983); deglycosylated PZI, a 35 kD protein; PZII, a 55 kD protein; and PZIII, an 80 kD protein all isolated by Skinner and Dunbar as described in *Immunological Approaches to Contraception and the Promotion of Fertility*, G. P. Talwar (ed.) New York: Plenum pp. 251–268 (1986); and deglycosylated ZP3 having a molecular weight of 45 kD isolated by Sacco et al., *J. Reprod. Fertil.* 76:575 (1986).

Isolated rabbit zona pellucida proteins include: RZI, RZII, and RZIII, having molecular weights of 68–125 kD, 80–100.5 kD, and 100–132 kD respectively, all isolated by Dunbar et al., *Biol. Reprod.* 24:1111 (1986); ZP1, ZP2, and ZP3 having molecular weights of 100–118 kD, 83–110 kD, and 80–92 kD respectively, all isolated by Sacco et al., *Proc. Soc. Exp. Biol. Med.* 167:318 (1981); deglycosylated RZI, and RZII having molecular weights of 65 kD, and 80 kD respectively, both isolated by Skinner and Dunbar and described in *Immunological Approaches to Contraception and Promotion of Fertility*. G. P. Talwar (ed.). New York: Plenum, pp. 251–268 (1986); and deglycosylated RZIII, a 90 kD protein isolated by Timmons and Dunbar, *Biol. Reprod.* 36: 1275 (1987).

A number of mouse zona pellucida proteins have been isolated including: ZP1, ZP2, and ZP3 having molecular weights of 200 kD, 120 kD, and 83 kD respectively, all isolated by Bleil and Wassarman *Dev. Biol.* 76:185 (1980); and ZP1 and ZP2 having molecular weights of 166–122 kD and 90–92 kD respectively, isolated by Sacco et al., *Proc. Soc. Exp. Biol. Med.* 167: 318 (1981). The differences in the molecular weights of mouse ZP1 and ZP2 as reported by Bleil et al. and Sacco et al. may be due to the fact that Bleil used 2D-PAGE under non-reducing conditions while Sacco used 2D-PAGE under reducing conditions.

The cat zona pellucida proteins CZI and CZII were isolated by Maresh and Dunbar *J. Exp. Zool.* 244:299 (1987) and have molecular weights of 50–110 kD and 90–110 kD respectively.

Maresh and Dunbar *J. Exp. Zool.* 244:299 (1987), have also isolated the dog zona pellucida proteins DZI, DZII, and DZIII which have molecular weights of 50–110 kD, 70–95 kD, and 90–100 kD respectively.

Sacco et al., *Proc. Soc. Exp. Biol. Med.* 167:318 (1981) described squirrel monkey ZP1, ZP2, ZP3, and ZP4 having molecular weights of 63–78 kD, 63–70 kD, 47–51 kD, and 43–47 kD respectively. In the same publication Sacco et al. described human ZP1, ZP2, and ZP3 having molecular weights of 80–120 kD, 73 kD, and 59–65 kD respectively.

To date, few mammalian zona pellucida genes or proteins have been isolated and sequenced. None has been successfully used to produce an effective immunocontraceptive. A lack of consensus among those of skill in the art regarding the number and characteristics (e.g. molecular weight) of proteins present in the zona pellucida of various mammalian species, and difficulties in purifying these heavily glycosylated proteins have hampered attempts to utilize zona pellucida proteins to produce an effective immunocontraceptive with predictable function.

A number of groups have had success in cloning cDNAs or genes encoding various mammalian zona pellucida proteins.

Ringuette et al., *Dev. Biol.*, 127:287–295 (1988) and Liang et al., *Mol. Cell. Biol.*, 10:1507–1515 (1990), reported cloning of mouse DNA encoding zona pellucida proteins ZP3 and ZP2, respectively. The clones were obtained by screening mouse cDNA libraries with anti-ZP3 and anti-ZP2 antibodies. No sequence homology was found between mouse ZP3 and ZP2.

Ringuette et al., *Proc. Natl. Acad. Sci. USA*, 83:4341–4345 (1986), reported isolation of a partial cDNA clone for mouse ZP3, which clone hybridized with total genomic DNA of mouse, rat, dog, cow, and human, but not with pig or rabbit genomic DNA unless the hybridization was performed at very low stringency. The full length ZP3 cDNA characterized by Ringuette *Dev. Biol.* 127:287–295 (1988) represents a germ-line specific mRNA having relatively short 5' and 3' untranslated regions and an open reading frame of about 1317 nucleotides with an additional 200–300 nucleotide poly-A tail. Ringuette also found that rat, rabbit, dog, and cow ovary transcribes mRNA which hybridized to the mouse ZP3 cDNA and that the ZP3 transcripts had similar molecular weights. Liang et al. *Mol. Cell. Biol.*, 10:1507–1515 (1990), showed that the nucleic acid and deduced amino acid sequence of ZP2 is distinctly different from that of ZP3 although it had the same short motif of 5' and 3' untranslated regions. The ZP2 mRNA is reported to have single open reading frame of 2,139 nucleotides which codes for a polypeptide of 80,217 Daltons representing 713 amino acids.

Chamberlin and Dean, *Dev. Biol.* 131:207–214 (1989) and Kinloch, R. A. et al., *Proc. Nat. Acad. Sci. USA*, 85:6409–6413 (1988) have reported the cloning of the mouse ZP3 gene. The mouse ZP3 gene is reported to have 8 exons and 7 introns in a transcription unit of 8.6 kbp.

Kinloch et al., *Dev. Biol.* 142:414–421 (1990), reported cloning of hamster genomic ZP3 DNA from a hamster genomic DNA library screened with mouse ZP3 DNA as a probe. The hamster ZP3 gene has a transcription unit of 7900 nucleotides and was found to contain 7 introns and 8 exons. The hamster ZP3 protein is approximately 81% homologous to mouse ZP3 protein. The hamster transcript contained 1266 nucleotides, six less than mouse ZP3 mRNA.

Chamberlain and Dean, *Proc. Natl. Acad. Sci. USA* 87:6014–6018 (1990), reported the cloning of human ZP3 from a human genomic DNA library using mouse ZP3 cDNA as a probe. The human ZP3 gene is composed of 8 exons in a transcription unit of 18.3 kbp. The exons are almost identical in size to the eight exons of mouse ZP3 and the nucleotide sequence of the coding region is 74% homologous. The human ZP3 transcript is very similar to mouse ZP3 mRNA. Both have short 5' and 3' untranslated regions, and both have a single open reading frame of 1272 nucleotides that encodes a 424-amino acid protein.

U.S. Pat. No. 4,996,297, to Dunbar, reported the isolation of three rabbit zona pellucida clones encoding rabbit ZP1 and ZP2 proteins, using anti-ZP1 and anti-ZP2 antibodies as screening probes. The sequences designated as P2 and P3 in FIG. 4 of the Dunbar patent represent rabbit ZP cDNAs of 812 and 1705 nucleotides respectively.

Schwoebel et al., *J. Biol. Chem.* 266:7214–7219 (1991), isolated and characterized a full length cDNA (designated rc 55) encoding the 55-kD rabbit zona pellucida protein using cross-species affinity purified antisera. The protein encoded by this cDNA has some similarity to the mouse ZP2 protein described by Liang. However, comparisons of rc 55 with the mouse ZP3 protein revealed no homology.

The functional activities of the cloned ZP DNAs and their encoded proteins have not been fully characterized and neither has their potential use as immunocontraceptives been demonstrated.

In order to develop a useful zona pellucida product for use in fertility control, particularly in the form of a vaccine, it is highly desirable to purify, isolate, and characterize zona pellucida proteins from a species of an animal of interest. Because of factors such as the purity of such proteins needed for vaccine production, and the high cost and numerous problems associated with purification of these proteins, it would be highly desirable to ascertain the DNA and amino acid sequences of zona pellucida proteins of a specific species of interest. Having such known, isolated and characterized zona pellucida proteins, the function of each zona pellucida protein may be understood and a fertility control product may be designed based upon the specific functional characteristics of a particular zona pellucida protein and for a particular mammalian species.

It would be thus highly useful and desirable to provide isolated, purified, sequenced, and characterized recombinant zona pellucida proteins which would permit the development of fertility control products possessing specific reproducible effects in eliciting transient and/or permanent infertility. Such products, where used to elicit transient infertility, would desirably have long lasting effects so as to minimize the number of times the immunocontraceptive agent must be administered to maintain infertility.

SUMMARY OF THE INVENTION

The present invention provides novel methods and materials for inducing either reproducible transient or permanent infertility effects in female mammals, including humans, by selective administration of homologous and/or heterologous mammalian species ZP proteins or immunocontraceptively active fragments thereof hereinafter designated as ZPA, ZPB and ZPC. By "reproducible" is meant that, unlike prior art attempts to induce transient infertility by administration of ZP proteins (in the form of mixtures of such proteins), this invention achieves its transient infertility effects by the administration of ZPA and/or ZPB in a form such that the duration of transient infertility is controllable and can be maintained in an on or off condition in a controllable and/or predictable fashion. This is achieved primarily through administration of the highly pure ZPA and ZPB proteins or immunocontraceptively active fragments thereof of this invention, e.g., in recombinant form and thus essentially devoid of ZPC. By immunocontraceptively active fragments is meant a ZP protein fragment capable of inducing infertility.

In one of its aspects, the present invention provides methods for inducing reproducible transient infertility in a mammal by administering to a subject female mammal a zona pellucida protein (or fragment thereof) selected from the group consisting of mammalian ZPA, and ZPB, and combinations thereof in doses effective to stimulate production in said mammal of antibodies which recognize ZPA or ZPB proteins of said mammal. It is presently preferred that mammalian ZPA and ZPB for use in such methods be derived from the same mammalian species as the subject mammal although the use of heterologous species proteins is also contemplated. Use of purified isolates of mammalian ZPA or ZPB protein such as obtained by chromatographic separatory procedures is contemplated. Use of proteins produced by recombinant methods is expected to be most preferred.

According to another aspect of the invention, methods are provided for inducing permanent sterility in a female mammal by administering to a subject female mammal a recombinant mammalian ZPC protein (or fragment thereof) in a form essentially devoid of ZPA and/or ZPB, in a dose effective to stimulate production in said female mammal of antibodies which recognize the ZPC protein of said mammal. As is the case with induction of transient infertility, use of homologous species ZPC is preferred, but not required, and the protein may be derived from natural sources or produced by recombinant methods. Modified ZPC proteins including but not limited to palmitylated and chitosan modified proteins are also contemplated by the present invention.

Presently preferred ZPA, ZPB, and ZPC proteins for veterinary application of the transient infertility and sterility inducing methods include porcine, rabbit, canine, feline, bovine, and cynomolgus monkey ZP proteins.

In another of its aspects, the present invention provides pharmaceutical compositions for use in inducing reproducible transient infertility in a female mammal (including humans) comprising an effective dose of a zona pellucida protein (or fragment thereof) selected from the group consisting of mammalian ZPA, and ZPB (substantially free of ZPC), in combination with one or more pharmaceutically acceptable carriers, diluents and adjuvants. Modified ZPA and ZPB proteins (for example, palmitylated or chitosan modified) are also contemplated by the present invention.

According to another aspect of the present invention, novel purified and isolated DNA sequences are provided which encode porcine ZPA, ZPB, and ZPC, as illustrated by the DNA sequences set out in SEQ ID NOS. 1, 3, and 5. Also, provided are purified and isolated DNA sequences encoding: rabbit ZPC, as illustrated by the DNA sequence set out in SEQ ID NO. 7; canine ZPA and ZPC, as illustrated by the DNA sequences set out in SEQ ID NOS. 9 and 11; feline ZPA, ZPB, and ZPC, as illustrated by the DNA sequences set out in SEQ ID NOS. 13, 15, and 17; bovine ZPA, ZPB, and ZPC, as illustrated by the DNA sequences set out in SEQ ID NOS. 19, 21, and 23; human ZPA and ZPB as illustrated by sequences set out in SEQ ID NO. 42 and 40, respectively, and as contained as human DNA inserts in lambda phage clones A1 and A4, (ZPA) and as contained in human DNA inserts in lambda phage clones 1-1 and 4-9 (ZPB).

Polynucleotide sequences of the invention are useful for the production of ZPA, ZPB and ZPC proteins by recombinant methods and as probes for the isolation of heterologous species polynucleotides encoding corresponding zona pellucida proteins by hybridization methods.

Also provided by the present invention are novel host cells, especially unicellular eucaryotic and procaryotic cells, stably transformed or transfected with polynucleotides of the invention in a manner allowing expression of the ZP proteins (or immunologically significant fragments thereof) in the host cells. Host cells expressing such ZP products, when grown in a suitable culture medium, and particularly useful for large scale production processes wherein the desired polypeptide products, in glycosylated or non-glycosylated form are isolated from the cells or the medium in which the cells are grown.

Recombinant polypeptides provided by the invention thus comprise ZPA, ZPB and ZPC, and full equivalents of such zona pellucida proteins including both glycosylated and non-glycosylated forms, variants and immunologically active fragments thereof which retain substantial biological activity, i.e., at least one of the biological activities of the zona pellucida protein discussed herein, e.g., the ability to stimulate the production of antibodies as discussed herein upon administration to a mammal. Such immunologically active fragments may be defined as containing at least one epitope effective to stimulate the production of antibodies upon administration to a mammal in accordance with this invention.

In another aspect of the invention, a method is provided for the isolation of nucleic acid sequences encoding other mammalian ZPA, ZPB, and ZPC proteins by hybridization under stringent conditions of heterologous species ZPA, ZPB, and/or ZPC probes to cDNA or genomic DNA libraries, derived from the mammalian species of interest.

More particularly, it is an aspect of the invention to provide a method for the isolation of nucleic acid sequences encoding human ZPA and ZPB by hybridization under stringent conditions of sequences encoding ZPA and/or ZPB from heterologous species.

Other aspects and advantages of the present invention will be readily understood upon consideration of the following detailed description of presently preferred embodiments thereof, reference being made to the figures wherein:

DETAILED DESCRIPTION OF THE INVENTION

Figure 1:
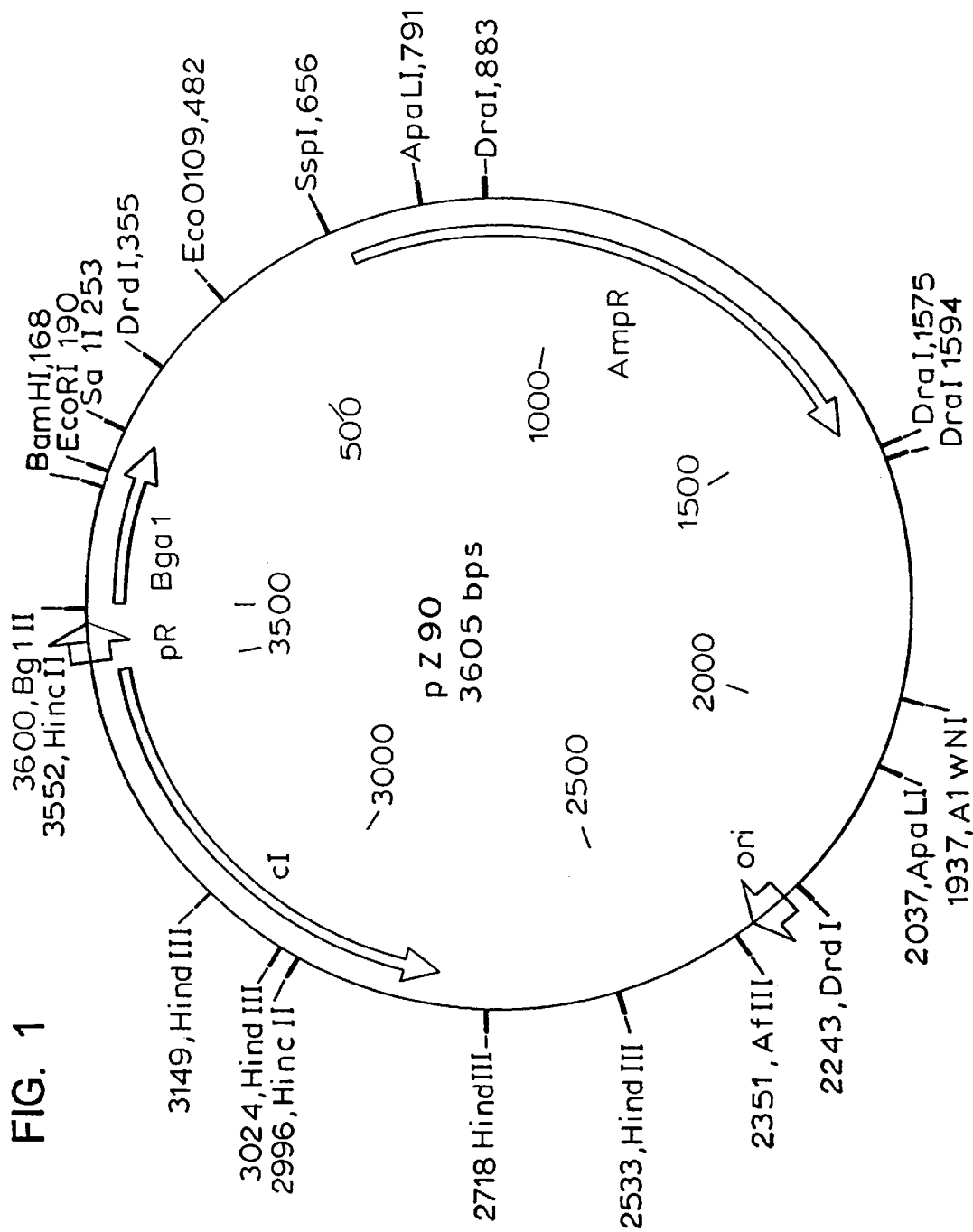
FIG. 1 is a diagrammatic representation of the plasmid vector pZ90.

The present invention is directed to mammalian zona pellucida proteins characterized in three major classes: ZPA, ZPB, and ZPC. This classification scheme has resulted from repetitive screening of various mammalian ovarian cDNA libraries and retrieval of clones which encode proteins showing significant homology in three distinct groups, designated herein as ZPA, ZPB and ZPC. Although similarity is seen between DNA sequences encoding ZPA, ZPB, or ZPC between animal species, very little homology is found between the individual species' ZPA, ZPB, and ZPC proteins.

DNA sequences encoding zona pellucida proteins A, B, and C and their deduced amino acid sequences for various mammalian species ZPs are presented in SEQ ID NOS. 1–24. It is understood that the DNA sequence of a particular animal may vary slightly due to the phenomenon of allelic variation. Small differences in the precise DNA sequence between animals or slight errors due to the inefficiency of sequencing procedures are to be expected. Such variants are included within the scope of the present invention.

The zona pellucida DNA sequences described above were obtained from ovarian cDNA libraries screened with specific zona pellucida antibodies or known zona pellucida DNA probes. Comparison of isolated sequences to published protein or DNA sequences and with other clones as they were isolated was used to classify and identify the clones as described above.

The term "zona pellucida protein" is meant to include full length proteins ZPA, ZPB, and ZPC, as well as expected variants, immunologically active fragments or peptides contained within these proteins. The term "zona pellucida DNA" is meant to include those nucleic acid sequences encoding zona pellucida protein or fragments thereof.

The three major classes of mammalian zona pellucida proteins have been determined on the basis of homology within the DNAs encoding ZP proteins of a variety of mammalian species. ZPA includes those peptides previously, variously described in the literature as ZP1, ZP2, and ZP4; ZPB includes those peptides previously, variously described as ZP3α and rc 55; and ZPC includes those peptides previously variously described as ZP3β and ZP3.

The homology of various species of zona pellucida proteins within a specific class as compared with a consensus sequence for each class is shown in Table 1. The consensus sequence was derived using the Microgenie® Sequence Analysis Program (Beckman Instruments, Inc. Spinco Division, Palo Alto, Calif.). The minimum percent of aligned sequences which must have the same residue at a given position for that residue to be included in the consensus sequence was 50%. The DNA sequences corresponding to the amino acid consensus sequences for ZPA, ZPB, and ZPC proteins are set out in SEQ ID NOS 25, 26, and 27, respectively.

TABLE 1

HOMOLOGY OF DEDUCED ZP PROTEINS AMINO ACIDS

|  | ZPA | ZPB | ZPC |
| --- | --- | --- | --- |
| DOG | 78.9% | — | 77.3% |
| CAT | 78.4% | 70.9% | 77.5% |
| COW | 77.2% | 80.4% | 77.2% |
| PIG | 73.0% | 77.8% | 79.0% |
| RABBIT | 70.1% | 74.6% | 71.3% |
| MOUSE | 61.6% | — | 69.6% |
| HUMAN | — | — | 76.9% |
| HAMSTER | — | — | 70.5% |

The deduced amino acid sequences of the various species of zona pellucida proteins suggest approximate unglycosylated molecular weights of 75 kD, 55 kD, and 45 kD for ZPA, ZPB, and ZPC, respectively. A more detailed analysis of both DNA sequence homology and deduced amino acid sequence homology is set out as Examples 13, 14, and 15.

It has surprisingly been found that administration of a specific class of zona pellucida protein to a host animal results in a specific immunocontraceptive effect and that selection of the appropriate ZP protein for administration allows induction of desired contraceptive results, in terms of permanent sterility or transient infertility. For example, vaccination of an animal with zona pellucida protein C induces antibody titers in that animal which recognize endogenous ZPC resulting in loss of oocytes from the animal's ovary, thereby causing permanent sterility. In contrast, vaccination of an animal with zona pellucida protein A, B or combinations thereof induces antibody titers which do not recognize ZPC, but recognize ZPA and/or ZPB. This results in cycling, infertile animals for the time period during which anti-ZPA and/or anti-ZPB antibody titers remain high. When such antibody titers fall, the infertility effect is diminished, and the animal regains fertility.

Vaccination with the purified, isolated, and characterized ZPA, ZPB, or ZPC proteins is seen to exert a specific effect on the immunized animal if an autoimmune response is triggered wherein the autoantibodies generated specifically recognize the immunized animals' own specific zona pellucida protein. This self-recognition for antibodies induced according to the present invention may be defined and characterized by the ability of serum antibodies to recognize at least one epitope present on a homologous species zona pellucida protein.

In the preferred method of the invention, an animal is immunized with a recombinant ZPA, ZPB, or ZPC or fragments thereof. The recombinant protein or peptide may be of homologous species or derived from a heterologous species zona pellucida which shares common epitopic determinants, with the proviso that such common epitopic determinants function to induce the desired autoimmune response.

The recombinant protein or peptide fragment may be chemically conjugated to immune enhancing agents such as Keyhole Limpet Hemocyanin (KLH), and Muramyl dipeptide (MDP), and the like, or alternatively may be provided in the form of a fusion protein, e.g., with foreign protein amino acids at the amino and/or carboxy terminus. Fully conventional methods for stimulating the production of antibodies upon administration of the proteins or fragments of this invention are well known; similarly, passive immunization techniques involving administration of antibodies per se, e.g., anti-ZPA antibodies, anti-ZPB antibodies, or anti-ZPC antibodies, to the zona pellucida proteins or fragments of this invention is also within the scope of the invention. For details, see Dean, PCT Application WO90/15624 whose disclosure is entirely incorporated by reference herein.

Thus, to induce permanent sterility in a dog, recombinant canine ZPC may be employed which is expressed as a bacterial fusion protein (or conjugated to immune enhancing agents) wherein active canine ZPC protein is conserved and available for interaction with antigen presenting cells. The expressed protein is then administered to a host dog and induces an autoimmune response in which generated antibodies recognize canine zona pellucida protein C. This autoimmune effect, which specifically recognizes dog ZPC protein or its aggregates, induces permanent sterility in the vaccinated dog, which sterility is associated with a loss of oocytes from the dog's ovary.

Alternately, a non-homologous species ZPC, such as recombinant porcine ZPC or peptides thereof which are cross-reactive with canine ZPC, can be administered to a dog to achieve similar sterilizing effects. The sterilizing effect, however, is only realized when antibodies capable of recognizing the host's own native zona pellucida are induced (or administered in the context of passive immunization).

In an alternative embodiment of the present invention, the administration of a host species' own A and/or B class zona pellucida protein, or a related A and/or B protein from another species which induce antibodies against the host's ZPA and/or ZPB proteins results in an infertility effect which is distinct from that produced by ZPC class antigens. The physiological effect of vaccination with the ZPA and ZPB proteins is a transient one. "Transient infertility" is herein defined as infertility which is maintained when antibodies against self-zona pellucida proteins are sustained in the host animal's circulation at a contraceptively effective concentration (e.g., at titers of approximately 1:250 in the dog) and which infertility is diminished when antibodies against self fall below a contraceptively effective lower limit. The reduction in antibodies against self-zona pellucida results in restoration of fertility without evidence of major physiological changes in the ovary. Typically, the reduction in antibody titers occur by natural processes in the mammalian host, but other methods of reducing antibody titers are within the scope of the invention.

Contraceptively effective antibody titers against self zona pellucida proteins A and B required to maintain infertility will vary with the species of vaccinated animal as well as with the species of recombinant ZPA or ZPB peptide administered, but may readily be determined, for example, by testing a panel of the desired animal species with varying doses of the specific antigen, measuring the induced titer of anti-self antibodies by known ELISA techniques, and correlating the titers with reproductive indicators, e.g., cycling, hormone levels, and the like. In general, antibody titers greater than 1:250 are contraceptively effective.

Based on amino acid sequence homologies, it is expected that all zona pellucida proteins of a particular class contain functional epitopes which are cross-reactive between mammalian species. However, absent characterization and identification of such functional cross-reactive epitopes, a preferred, selective contraceptive agent is a homologous species zona pellucida protein or antibody thereto.

The present invention will be more completely understood upon consideration of the following illustrative examples of the practice thereof wherein: Example 1 addresses the isolation of DNAs encoding porcine species ZPA, ZPB and ZPC; Example 2 relates to isolation of rabbit ZPC DNA; Example 3 relates to isolation of DNAs encoding canine ZPA and ZPC; Example 4 addresses isolation of feline DNAs encoding ZPA, ZPB and ZPC; Example 5 relates to cloning and isolation of DNAs encoding bovine species ZPA, ZPB and ZPC; Examples 6 and 7 describe immunocontraceptive treatment of dogs with naturally-derived porcine zona pellucida proteins; Example 8 relates to serochemical studies on animals treated in Examples 6 and 7; and Examples 9 and 10 address recombinant production of a canine ZPC fusion protein and its immunocontraceptive use in dogs. Example 11 relates to the isolation of DNAs encoding human ZPA and ZPB by methods described herein. Example 12 relates to the isolation and sequencing of DNAs encoding cynomolgus monkey ZPA, ZPB and ZPC. Examples 13–15 relate to the comparison of the DNA sequence and the deduced amino acid sequence of mammalian ZPA, ZPB, and ZPC, respectively. Example 16 relates to the immunization of cynomolgus monkey using HSPZ and fractionated HZPC. Example 17 relates to the mapping of mammalian zona pellucida protein epitopes. Example 18 describes the immunization of dogs using recombinant ZPC proteins. Example 19 relates to the vaccination of cows and cats with recombinant ZP proteins.

EXAMPLE 1

Isolation of DNA Sequences Encoding Porcine Zona Pellucida Proteins ZPA, ZPB, and ZPC A cDNA library in λgt11 was commercially prepared by Clone Tech, Palo Alto, Calif., from an ovary isolated from a 14 week old pig and was screened using an anti-ZP3β antibody obtained from E. C. Yurewicz and described in Keenan et al., Biol. Reprod., 44:150–156 (1991). Eight candidate clones were identified.

A degenerate DNA oligonucleotide probe (19 bps) was constructed to represent all possible sequences of a short portion of the N-terminus porcine ZP3β as described in Yurewicz et al., J. Biol. Chem., 262:564–571, (1987). The degenerate probe sequence is set out in SEQ ID NO. 28.

Southern analysis of the eight candidate clones isolated by expression screening with the degenerate DNA oligonucleotide probe resulted in hybridization with two of the eight candidates. The two clones recognized by the degenerate probe were then subcloned into the pBS KS plasmid (STRATAGENE Cloning Systems, La Jolla, Calif.) for sequence analysis using the sequence enzyme and the protocol described in the SEQUENASE® Manual (U.S. Biochemical, Cleveland, Ohio). One of the clones, B-8, having an insert size of approximately 1200 base pairs, included a sequence homologous to the N-terminal sequence of mouse ZP3, previously identified by Ringuette et al., Dev. Biol., 127:287–295, (1988). The remaining clone, B-6, had an insert size of approximately 1000 base pairs. Neither hybridizing clone contained the C-terminal portion of the gene, as suggested by the lack of homology to the mouse ZP3 gene in this region.

The 14-week porcine ovarian library was then rescreened by DNA hybridization. Approximately 150,000 PFUs were plated on agar plates with E. coli Y1090. After overnight incubation at 37° C., nylon membrane lifts of plaques were prepared and screened using the B6 and B8 clones derived above isolated by screening with the degenerate oligonucleotide probe set out in SEQ ID NO. 28.

Filters were prehybridized in a solution containing 5× saline, sodium phosphate, EDTA buffer (SSPE), 5× Denhardt's Reagent, 100 μg/ml salmon sperm DNA, 30% formamide and 0.5% SDS for three hours at 42° C. Approximately 50 ml of the prehybridization solution was used for 12 filters (132 mm). After prehybridization, 10 ng of freshly radiolabeled DNA probe in 30% formamide, 5× SSPE was added. The probes were heat denatured at 95° C. for 3–5 minutes and hybridization with the DNA probes continued overnight at 42° C. The hybridized filters were then washed twice with 100 ml of 5× SSPE at 55° C., for approximately one hour each wash. The filters were then rinsed with 250 ml of 5× SSPE at room temperature and allowed to air dry. The dried filters were exposed to x-ray film at −70° C. using intensifier screens for at least eight hours and the films were developed for visual analysis.

Among the additional clones isolated were two clones including the C-terminal portion of the porcine ZP3β gene. One clone, λ5-1, was subcloned into plasmid pBS KS and sequenced. This plasmid, termed pZ57, contained a ZP DNA insert having 1266 base pairs and appeared to encode the full length amino acid sequence of porcine ZP3β as compared with known mouse ZP3. Alignment of the deduced amino acid sequence of the clone with the known N-terminal amino acid sequence of ZP3β reported by Yurewicz et al., J. Biol. Chem., 262:564–571 (1987), and an internal peptide sequence of ZP3β corresponding to amino acids 255–274 as provided by E. C. Yurewicz confirmed the identity of this clone as encoding porcine ZP3β.

The DNA sequence of this clone, termed porcine ZPC, is set out in SEQ ID NO. 5 and its deduced amino acid sequence is set out in SEQ ID NO. 6.

The 14-week porcine ovarian cDNA library was further screened using rabbit zona pellucida rc 55 cDNA as a probe [described in Schwoebel et al., *J. Biol. Chem,* 266:7214–7219, (1991)].

One candidate clone of approximately 1700 base pairs, λ2-1, was isolated and was transferred into the sequencing plasmid pBS KS. The DNA sequence and deduced amino acid sequence of the porcine DNA insert was determined using the method described in the SEQUENASE® manual (US Biochemical Corporation, Cleveland, Ohio). The sequenced clone contained 1620 base pairs and included a full length copy of the porcine ZP3α gene as confirmed by alignment of the deduced amino acid sequence with portions of the known protein sequence of porcine ZP3α provided by E. C. Yurewicz between amino acids 206–222, 271–279, and 328–344. The DNA sequence of this clone, termed porcine ZPB, is set out in SEQ ID NO. 3. Its deduced amino acid set out in SEQ ID NO. 4.

The 14-week porcine ovarian library was further screened using the procedure described above and using a DNA probe encoding canine ZPA protein (as obtained in Example 3 below, SEQ ID NO. 9). A single clone, λ3-5 having approximately 1300 base pairs, was obtained representing the N-terminal 60% of the theoretical porcine ZPA gene as estimated by the size of the clone in relation to the ZP2 gene isolated from mouse by Liang et al., *Mol. Cell. Biol.* 10: 1507–1515 (1990), and rabbit by Dunbar, U.S. Pat. No. 4,996,297, and dog (see Example 3 below).

This clone was then used to rescreen the porcine ovarian library. Three additional clones were obtained, two small clones and one clone large enough to contain the full length sequence. The large candidate clone, λB, having approximately 2200 base pairs, was sequenced, and the data showed this ZPA clone to lack only approximately seven base pairs of the full length sequence including the ATG start codon when aligned with the mouse ZP2 gene and the canine ZPA gene described in Example 3. The DNA sequence of this clone, termed porcine ZPA, is set out in SEQ ID NO. 1. Its deduced amino acid sequence is set out in SEQ ID NO. 2.

This isolated porcine clone included sequences corresponding to published sequences of three identified porcine zona pellucida proteins, ZP1 (80 kD), ZP2 (62 kD) as disclosed in U.S. Pat. No. 4,996,297 to Dunbar and ZP4 (21 kD) as disclosed by Hasegawa et al., Abst. No. 382, *Meeting Soc. Study Reprod*. July, 1991. These results suggest that a singular clone encodes one zona pellucida protein which previously had been thought to exist as three separate proteins, i.e., ZP1, ZP2, and ZP4. This further suggests that only three major porcine zona pellucida genes encode three major zona pellucida proteins which here are termed ZPA, ZPB, and ZPC. ZPA includes those proteins previously identified as ZP1, ZP2, and ZP4. ZPB corresponds to ZP3α and ZPC corresponds to previously identified ZP3β. Yurewicz et al. *J. Biol. Chem.,* 262:564–571, (1987).

EXAMPLE 2

Isolation and Purification of DNA Sequences Encoding Rabbit ZPC Protein

Ovaries were removed from five week old rabbits and mRNA was prepared using the Fast Track™ mRNA isolation kit in accordance with the procedure described in the *Fast Track*™ instruction manual, version 3. 1, catalog No. K1593-02 (Invitrogen, San Diego, Calif.). A Lambda Librarian™ kit (Invitrogen, San Diego, Calif.) was used to prepare cDNA and to clone cDNAs into λgt10 according to the manufacturer's .instructions. Approximately 150,000 PFUs were plated on agar plates with *E. coli* Y1090. After overnight incubation at 37° C., nylon membrane lifts of colonies were prepared and screened with a porcine ZPC DNA probe using the screening procedures described for Example 1. The probe used was the porcine ZPC sequence as set out in SEQ ID NO. 5.

Two positive clones, λR4 and λR5, hybridized with the porcine ZPC DNA. The size of each of these clones as estimated in agarose gels was approximately 1300 base pairs. Both λR4 and λR5 were sequenced as described for Example 1. The sequences were identical except that λR5 contained four additional nucleotides at the 5' end. The determined DNA sequence was approximately 75% homologous to the DNA sequence encoding porcine ZPC.

The DNA sequence encoding rabbit ZPC protein is set out in SEQ ID NO. 7. Its deduced amino acid sequence is set out in SEQ ID NO. 8.

Rabbit ZPA and ZPB proteins have been previously identified by Dunbar in U.S. Pat. No. 4,996,297 as P2 and P3, respectively.

EXAMPLE 3

Isolation of DNA Sequences Encoding Canine Zona Pellucida Proteins ZPA and ZPC

A 16 week canine ovarian cDNA expression library was commercially prepared by Clone Tech, Palo Alto, Calif., in λgt11 generally following the methods described in Example 1. The canine ovarian cDNA library was screened using antibodies raised against heat solubilized canine zona pellucida. Heat solubilized canine zona pellucida (HSDZ) was prepared generally following the procedures described in Dunbar et al. *Biochemistry,* 19:356–365, (1980) except ganged razor blades were used to mince the ovaries.

Rabbits were immunized with 250 μg HSDZ and 250 μg MDP. Two additional boosts followed at approximately three week intervals. The resultant rabbit serum was used to screen the canine ovarian cDNA expression library. Seven candidate clones were obtained. Cross-hybridization experiments were performed by Southern blot analysis as follows. The largest clone, λ26-1, having approximately 1300 base pairs, was first used as a probe against all of the other clones in Southern blots. Three other clones were identified. The largest of the remaining clones, λ20-1 and λ7-1, having approximately 800 and 1000 base pairs respectively, were then used as probes in Southern blots. These probes identified no additional clones. This cross hybridization analysis of the seven candidate clones to each other indicated that four of these clones were related, e.g. four clones hybridized to λ26-1 while the remaining three λ20-1, λ7-1, and λ19-3 were independent.

The largest of the four related clones, λ26-1, was subcloned into pBS KS plasmid for sequence analysis according to the procedure described in Example 1. The analyzed sequence demonstrated the presence of a long open reading frame of 1278 base pairs encoding a protein of approximately 426 amino acids. Comparison of the deduced amino acid sequence of this clone with the sequences of known zona pellucida proteins, indicated this clone encoded a protein related to mouse ZP3 (ZPC) as reported by Ringuette et al., *Dev. Biol.* 127:287–295 (1988), hamster ZP3 as reported by Kinloch et al., *Dev. Biol.,* 142:414–421 (1990), human ZP3 as reported by Chamberlin et al., *Proc. Natl. Acad. Sci. USA* 87:6014–6018 (1990) and porcine ZPC protein (see Example 1). The DNA sequence of this clone, termed canine ZPC, is set out in SEQ ID NO. 11. Its deduced amino acid sequence is set out in SEQ ID NO. 12.

The remaining three independent candidate clones were subcloned into the pBS KS plasmid for sequence analysis as described above. The determined sequence of the 800 base pair clone, λ20-1, was compared with known ZP sequences by computer analysis as described above and was found to be related to the mouse ZP2 (ZPA) [Liang et al., *Mol. Cell. Biol.* 10:1507–1515 (1990)] and porcine ZPA (see Example 1).

The 800 base pair fragment from λ20-1, was then used as a hybridization probe to rescreen the canine cDNA library. Two additional candidate clones were identified, the larger of which, λ7A, having approximately 2800 base pairs, was subcloned into pBS KS plasmid for sequence analysis. Comparison of this sequence with known sequences encoding zona pellucida proteins suggested the candidate clone λ7A contained a full length ZPA sequence, but an incorrect N-terminal sequence, e.g., the clone contained an additional 600 base pairs as determined by alignment with known mouse ZP2 and rabbit ZPA sequences referenced in Example 1. The second candidate clone, λ9-2, having approximately 1000 base pairs, was then subcloned into the plasmid pBS KS and sequenced. The sequence of the second clone indicated the presence of a correct N-terminal sequence, but included only approximately the N-terminal 40% of the full length clone as determined by alignment with the mouse ZP2 and rabbit ZPA genes. Overlap of the two cDNA clones, however, provided the full length sequence.

The appropriate pieces of each clone were subcloned as follows to generate the correct full length zona pellucida clone containing a 2028 base pair open reading frame encoding a protein of approximately 676 amino acids. The λ7A DNA was digested with Eco RI to yield two insert fragments (2000 bps and 800 bps). These two fragments were each subcloned into pBS KS yielding pZ36 and pZ37, respectively. Plasmid pZ37 carried the C-terminal portion of this sequence. The λ9-2 DNA insert was removed from the λ vector and subcloned into pBS KS to yield pZ38. Plasmid pZ36 was digested with Hind III to remove approximately 1350 bps of the N-terminal portion of the λ7A gene fragment (about 850 bps of nonsense DNA and 500 bps of coding sequence). This digestion also removed one of the Eco RI insert ends and left a single Eco RI site. The pZ37 Eco RI insert was then moved into the single remaining Eco RI site in the modified pZ36 (pZ36 ΔI) to reestablish the relative DNA structure orientation that existed in the λ7A insert (1450/2800 bps). This combined plasmid was then opened with Hind III and the Hind III fragment from pZ38 carrying the N-terminal ZP DNA sequence was inserted to create plasmid pZ39 which is a pBS KS carrying the full length canine ZPA sequence. The DNA sequence of this canine ZPA gene is set out in SEQ ID NO. 9. Its deduced amino acid sequence set out in SEQ ID NO. 10.

EXAMPLE 4

Isolation of DNA Sequences Encoding Feline Zona Pellucida Proteins ZPA, ZPB, and ZPC Ovaries were isolated from five cats approximately three to four months in age. Messenger RNA was isolated from six ovaries using the Fast Track™ mRNA Isolation Kit (Invitrogen, San Diego, Calif., Catalog No. K1593-02) using the protocol provided with the kit. cDNA was prepared using the protocol and cloned into λgt10 as described in Example 2.

Approximately 150,000 plaque forming units (PFUs) were plated on agar plates with *E. coli* Y 1090. After overnight incubation at 37° C., nylon transfer membranes were used to prepare and screen plaque lifts. Plaques were screened using a mixture of DNA probes in equal proportions encoding porcine ZPA, ZPB, and ZPC proteins and using the hybridization procedure as described for Example 2. A total of 81 positive clones were identified. Twelve of these clones were plaque-purified. Southern analysis of these clones using porcine ZPA, ZPB, and ZPC DNAs individually as probes indicated that seven of these clones encoded ZPC proteins and one clone encoded a ZPA protein. Four of the clones contained inserts which could not be separated by Eco RI digestion.

Five of the ZPC clones were between 1200–1350 base pairs in length. One clone, λC-112, having approximately 1350 base pairs was subjected to sequence analysis as described above and its deduced amino acid sequence was found to be approximately 70% homologous to the canine ZPC protein obtained in Example 3. The DNA sequence of this feline ZPC clone is set out in SEQ ID NO. 17. Its deduced amino acid sequence is set out in SEQ ID NO. 18.

The single feline ZPA clone, λC-116, was sequenced and found to be approximately 2215 base pairs in length. The deduced amino acid sequence was approximately 75% homologous to the canine ZPA protein characterized in Example 5. The DNA sequence of this feline ZPA clone is set out in SEQ ID NO. 13. Its deduced amino acid sequence is set out in SEQ ID NO. 14.

The remaining 69 positive clones were rescreened using porcine ZPB DNA as a probe (SEQ ID NO. 3). Ten positive clones were obtained. The largest clone, λC-1, contained approximately 1.7 kilobases as determined by agarose gel electrophoresis. This clone was sequenced, and its deduced amino acid sequence was found to be approximately 80% homologous to the porcine ZPB protein described in Example 1. The DNA sequence of this feline ZPB clone is set out in SEQ ID NO. 15. Its deduced amino acid sequence is set out in SEQ ID NO. 16.

EXAMPLE 5

Isolation of DNA Sequences Encoding Bovine Zona Pellucida-Proteins ZPA, ZPB, and ZPC A cDNA library was constructed from a five month bovine ovary by the method described in Example 2. The bovine ovarian library was screened with DNA hybridization probes representing each of the classes of zona pellucida proteins using a mixture of equal proportions of porcine DNA probes encoding ZPA (SEQ ID NO. 1), ZPB (SEQ ID NO. 3), and ZPC (SEQ ID NO. 5) proteins, as described for Example 2 and using the procedures described for Example 1. Initial screening yielded three candidate clones. Southern analysis of these clones with individual porcine ZPA, ZPB, and ZPC DNA probes used in the initial screening indicated that one of the clones, λB2, having approximately 650 base pairs, encoded ZPA. A second clone, λB-1 having approximately 1000 base pairs encoded ZPB. A third clone, λB14, having approximately 1200 base pairs, encoded ZPC.

The bovine ovarian library was then rescreened with the mixed porcine ZP DNA probes. Two additional clones were obtained and identified by Southern analysis as encoding ZPC.

The Eco RI inserts of the ZPA, ZPB, and largest ZPC clone were subcloned and their DNA sequences analyzed. The sequences encoding these bovine ZPA, ZPB and ZPC fragments were set out in SEQ ID NOS. 19, 21, and 23, respectively. Their deduced amino acid sequences are set out in SEQ ID NOS. 20, 22, and 24, respectively.

EXAMPLE 6

Immunization of Dogs with Heat-Solubilized Fractionated Porcine Zona Pellucida Heat-solubilized, porcine zona pellucida (HSPZ) was prepared generally following the procedures described by Dunbar et al. *Biochemistry*, 19:356–365, (1980) but using a hand powered meat grinder instead of the Zonamatic described. Following isolation, the zona pellucida protein was solubilized in 0.1 M sodium carbonate buffer, pH 9.6, and was dialyzed extensively against 6M urea. The resultant solution, a volume of 2–3ml containing approximately 12 μg of HSPZ, was subjected to isoelectric-focusing in a BIO-RAD Rotofor isoelectric-focusing chamber as follows. An isoelectric gradient was established using 1% ampholytes having a pI range of 3–10. The zona pellucida protein was introduced into the mid-range chamber (pI 7.0) and allowed to focus for approximately four hours at 4° C. or until the voltage stabilized.

Twenty isoelectrically focused fractions were collected and analyzed by SDS PAGE and Western blot analysis for pig zona pellucida proteins. Acidic fractions having a pI range of approximately 3.5–5.5 and which contained the porcine zona pellucida proteins were combined. The fractions were dialyzed into 0.1M carbonate buffer, pH 9.6 and concentrated to approximately 3 mg/ml. This antigenic preparation was used to vaccinate animals as described below. Analysis of this antigenic preparation by two-dimensional gel electrophoresis indicated the presence of ZPA and ZPB protein. However, ZPC was not revealed to be present in this preparation.

The HSPZ antigenic preparation was added to a 50/50 water oil emulsion with incomplete Freund's adjuvant (Sigma, St. Louis, Mo.) containing 250 μg of MDP per dose. One ml of the 50/50 water oil emulsion contained 0.425 ml paraffin oil, 0.075 ml mannide monooleate, and 0.5 ml PBS containing 250 μg threonyl-MDP (SYNTEX Corporation) and the amount of HSPZ described in Table 3 below.

Four random breed dogs aged 10–12 weeks were immunized with HSPZ using the regimen described in Table 2.

TABLE 2

|  |  | mg HSPZ |
|---|---|---|
| Prime | Time 0 | 0.1 |
| Boost #1 | Week 4 | 1.0 |
| Boost #2 | Week 8 | 0.25 |
| Boost #3 | Week 12 | 0.2 |
| Boost #4 | Week 16 | 1.0 |
| Boost #5 | Week 36 | 1.0 |

The antisera produced by these animals was monitored via ELISA methodology. By week 17 antibody titers against self, e.g. against canine zona pellucida proteins, had reached a maximum (8–16K by ELISA) and thereafter began to drop.

At week 36, one animal was unilaterally ovariectomized and the removed ovary was sectioned and stained with periodic acid schiff stain (PAS) for histological examination. The ovary appeared normal, as evidenced by the presence of follicles in all stages of development. At week 52, two of the four test animals were observed to exhibit estrus behavior. The remaining two test animals exhibited estrus behavior at approximately one and a half years when the first two test animals experienced their second heat. All test animals were bred repeatedly with competent males and by artificial insemination, however, none became pregnant. During this same period, animals in various test regimens in which no self titers were obtained, as described in Example 10, became pregnant when presented with the same males or artificial insemination techniques.

Two weeks following the breeding sessions, e.g. at 54 weeks, the two early cycling animals were unilaterally ovariectomized and the removed ovaries were sectioned for histological examination. The ovaries appeared normal for this stage of follicular activity despite the functional infertility demonstrated.

EXAMPLE 7

Vaccination With Porcine ZPC Protein

A purified porcine ZPC protein (ZP3β) was obtained from E. Yurewicz, prepared as described in *J. Biol. Chem.*, 262:564–571, (1987).

Vaccines were prepared by adding 167 μg purified porcine ZPC protein (ZP3β) to a 50/50 water-oil emulsion with complete Freund's adjuvant (Sigma No. F5881, St. Louis Mo.), for the priming dose or with Incomplete Freund's Adjuvant (Sigma No. F5506, St. Louis, Mo.) containing MDP as described in Example 6 for the booster doses.

Five random breed dogs of approximately 10–12 weeks of age were injected with the ZPC vaccine preparation described above using the 5 regimen described in Table 3.

TABLE 3

|  |  | mg of ZPC |
|---|---|---|
| Prime | Time 0 | 0.167 |
| Boost | Week 3 | 0.167 |
| Boost | Week 6 | 0.167 |
| Boost | Week 28 | 0.167 |

Each animal's antibody titer versus self- zona proteins, e.g., versus canine zona pellucida proteins, was monitored by ELISA, using the method described in Dunbar, *Two Dimensional Gel Electrophoresis and Immunological Techniques,* 1987. ELISA microtiter plates were coated with HSDZ in antigen-coating buffer (0.1M sodium carbonate, pH 9.6). Biotinylated rabbit-antidog IgG was used as the second antibody. ABC reagent (Avidin-biotinylated peroxidase complex) and O-phenylene diamine dihydrochloride with a peroxide substrate was used for visualization. Only two animals produced antibodies versus self achieving peak self-antibody titers of 16K by week 4. The other three animals produced no self-antibody titers but achieved peak antibody titers of 4K against porcine zona pellucida protein. During the period of time between week 20 and week 36, all dogs were observed to exhibit estrous behavior. The animals were bred repeatedly with proven males. Only the two animals having antibody titers versus self zona pellucida proteins remained infertile. All other animals in the study became pregnant.

Two weeks after estrous and breeding the two infertile dogs exhibiting self-antibody titers were unilaterally ovariectomized and the removed ovaries were sectioned and stained with PAS for histological examination. The histological examination revealed abnormal morphology in the ovaries of the infertile dogs. No evidence of ongoing folliculogenesis was seen and the ovaries were depleted of oocyte-containing follicles. In addition, no primordial oocytes were seen.

EXAMPLE 8

Western Analysis of Antisera Produced by Vaccinated Animals

In an attempt to better understand the immune response and different physiological effects obtained in the two studies described in Examples 6 and 7, antisera produced in each test group was analyzed by Western Analysis against a variety of antigens including natural porcine ZPC, heat-solubilized dog zona pellucida (HSDZ), recombinant dog ZPA and ZPC, and recombinant pig ZPC. Western blots were probed with antiserum obtained from the test animals of Example 6, e.g., animals immunized with isoelectric focused, heat-solubilized porcine zona pellucida, and with antiserum obtained from the two test animals of Example 7 which contained antibodies against self-zona proteins.

The data demonstrate no recognition of recombinant porcine or canine ZPC by antisera from infertile, but cycling dogs immunized with heat solubilized porcine zona pellucida which contained no demonstrable ZPC by PAGE analysis, however, natural ZPC, HSDZ and recombinant canine ZPA were recognized. In contrast, antisera obtained from infertile dogs whose ovaries were depleted of oocytes recognized recombinant ZPC protein, i.e., the polypeptide backbone.

A key difference in the antibody recognition of antigen was that only the antisera obtained from dogs having ovaries devoid of oocytes appeared to recognize the recombinant dog ZPC antigen. Infertile dogs whose antisera strongly recognized natural ZPC, HSDZ, and recombinant dog ZPA demonstrated no recognition of recombinant dog ZPC.

Given that autoimmunity is essential for a contraceptive effect, these data suggest that infertility without histologically evident ovarian dysfunction can be obtained in dogs via an autoimmune response against dog ZPA antigens. In contrast, histologically confirmed ovarian dysfunction, i.e., loss of oocytes, which would result in permanent sterility, requires the generation of antibodies which specifically recognize homologous species ZPC protein.

EXAMPLE 9

Expression of Recombinant ZP Proteins

I. Construction of Expression Vectors

The plasmid vector pZ90 shown in FIG. 1 was constructed from fragments of the plasmids pUC9 (Vierra & Messing, Gene 19:259–268 (1982)) and pβgal2 (Queen, J. Mol. App. Gen. 2:1–10 (1983)). The single Pvu II restriction site present in pβgal2 was converted to a Sal I site using a Sal I polylinker adaptor purchased from New England Biolabs. The DNA sequences between the new Sal I site and a pre-existing Sal I site were excised by digestion with Sal I, religated and screened for the reduced size plasmid.

A Cla 1-Nde I fragment of the modified pβgal2 plasmid which carried the λCI repressor gene, the λpR promoter and the Lac Z gene (β-galactosidase) was inserted into pUC9 between its Acc I and Nde I restriction sites. The pUC9 plasmid carries the ampicillin resistance (Amp$^R$) gene and col EI replication origin (ori) needed to maintain the plasmid in E. coli cells. The combination plasmid was further modified to convert the Bam HI site 3' of the ATG initiation codon (ATG GAT CCN) to a Bgl II site 5' of the ATG initiation codon (AGATCTATG). This was accomplished by partially digesting the plasmid with Rsa I. One of the several digestion points was about 20 bps 5' of the Bam HI restriction site. When the partially digested plasmid was digested with Bam HI, some of the plasmids produced were nearly full length. A synthetic oligomer (GTACTAAGGAAGATCTATGGATCC) (SEQ ID NO. 29) was produced to replace the sequence that had been removed (GTACTAAGGAGGTTGTATGGATCC) (SEQ ID NO. 30). The net effect of this replacement was the substitution of 3 bps to create the Bgl II restriction site. A DNA fragment containing approximately 3000 base pairs of the Lac Z gene was then excised by restriction digestion with Bgl I and Ban II and was followed by insertion of a synthetic oligomer containing a Bam HI site. The plasmid was cut with Bgl I and Ban II, and then treated with nuclease S1 to create blunt ends. A Bam HI linker (New England Biolabs) was inserted at the blunt ends of the digested plasmid. Next a Pvu II restriction site between the λCI repressor gene and the ori sequence was converted to a Hind III site using a synthetic linker. The Pvu II restriction site was cut with Pvu II, and a Hind III linker (New England Biolabs) was ligated to the blunted ends. Because the remaining lac Z sequence was missing the first 8 codons of the natural sequence, these 8 codons were replaced by synthesizing a synthetic oligomer that began with a Bgl II site and encoded the lac Z wild type gene product (βgal) N-terminal sequence.

The synthetic oligomer was prepared by synthesizing four oligomers having the sequences set out in SEQ ID NO. 31 (oligomer 1), SEQ ID NO. 32 (oligomer 2), SEQ ID NO. 33 (oligomer 3), and SEQ ID NO. 34 (Oligomer 4). Oligomers 2 and 3 were phosphorylated by treating with kinase and ATP to add phosphate to the 5' end. Oligomers 1 and 2 were then hybridized to oligomers 3 and 4, respectively, by incubation at 100° C. followed by a slow cooling in 200 μM NaCl. The resultant oligomer had the sequence set out in SEQ ID NO. 35. The synthetic oligomer as set out in SEQ ID NO. 35 had Bgl II-Pvu II ends and was substituted for the Bgl II-Pvu II sequence of the plasmid by restriction digestion of the plasmid and ligation with the oligomer.

Figure 2:
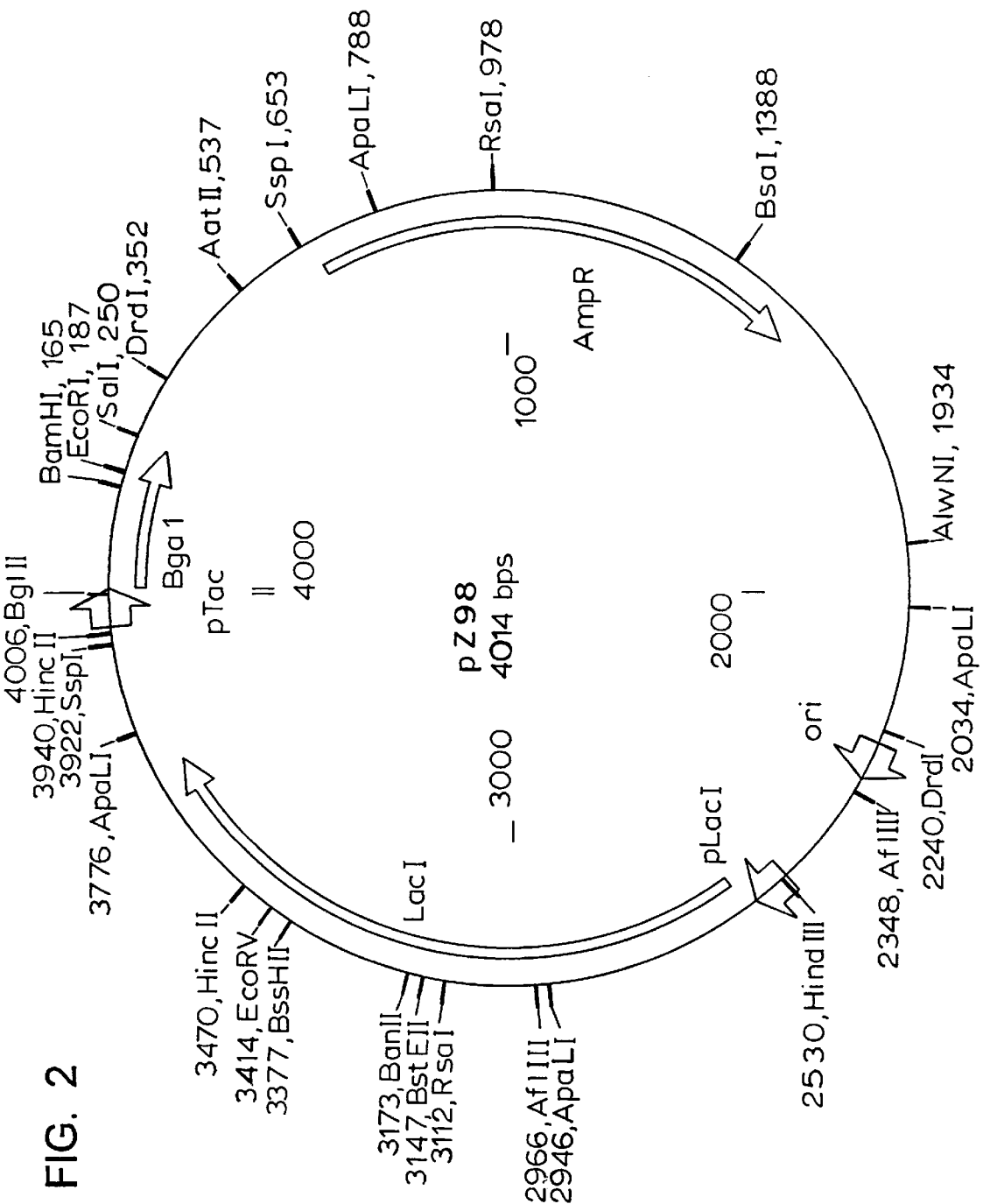
FIG. 2 is a diagrammatic representation of the plasmid vector pZ98.

The resultant plasmid was termed pZ90 and is shown in FIG. 1. The plasmid pZ90 can be used to express recombinant proteins by heat induction, using the heat labile λCI repressor. The heat-inducible repressor and promoter of pZ90 was next replaced with the chemically inducible promoter ptac (Amann et al., Gene 25:167–178 (1983)). The ptac promoter is controlled by the lac repressor, a product of the lac I gene (Farabaugh, Nature 279:765–769 (1978)). The Lac I gene was obtained from pMC9 (Miller et al., The EMBO Journal 3:3117–3121 (1984)) by use of PCR methodology as described by Innis and Gelfand, In: PCR Protocols: A Guide to Methods and Applications, Innis, M. A., Gelfand, D. H., Sninsky, J. J. and White, T. J. (eds)., pgs 1–12, Academic Press, Inc., San Diego, Calif. The primers used were complimentary to the Lac I promoter at one end and the Lac I gene termination codon at the opposite end. The N-terminal primer carried a Hind III site and the C-terminal primer carried a tac promoter sequence followed by a Bgl II site. The N-terminal primer had the sequence set out in SEQ ID NO. 36. The C-terminal primer had the sequence as set out in SEQ ID NO. 37 which includes a Dra 3 site having the sequence 5'-CACAATGTG-3'. The resulting lac I—ptac DNA fragment having Hind III and Bgl II restriction sites at its respective ends was then used to replace the Hind III—Bgl II fragment of pZ90 which carried the λCI repressor and λpR promotor. This replacement yielded the plasmid pZ98 shown in FIG. 2.

II. Insertion of Recombinant ZP DNA

DNA sequences encoding porcine ZPC were prepared by the PCR procedures described above (Innis & Gelfand) from the plasmid pZ57 prepared in Example 1, which contains the full length porcine ZPC sequence obtained from λgt11 clone 5-1 described for Example 1. During the PCR procedure the porcine ZPC gene was modified by using primers that did not include the leader sequence and the hydrophobic tail. The N-terminal primer used had the sequence set out in SEQ ID NO. 38 which. included an internal Bam HI restriction site having the sequence 5'-GGATCC-3'. The C-terminal primer used had the sequence as set in SEQ ID NO. 39 includes a Sal I restriction site having the sequence 5'-CTCGAG-3' and an internal Xho I restriction site having the sequence 5'-CTCGAG-3'. The modified ZPC gene contained base pairs 105 to 1154 encoding ZPC amino acids 1–350.

Figure 3:
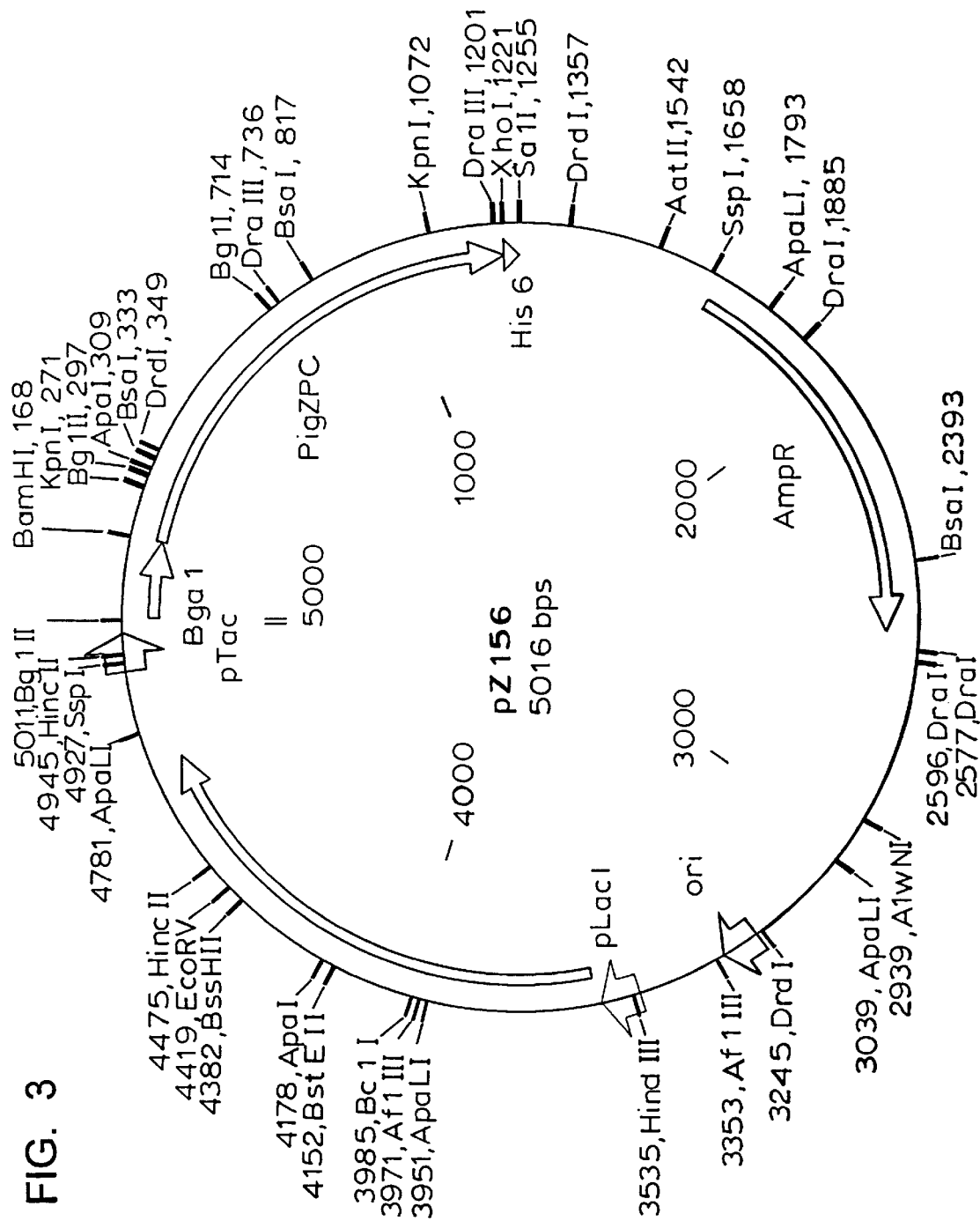
FIG. 3 is a diagrammatic representation of the plasmid vector pZ156.

To the 5' end of the modified porcine ZPC gene was added a Bam HI restriction site, and to the 3' end was added an Xho I site, a Hexa-CAT-codon sequence $(CAT)_6$, a termination codon, and a Sal I restriction site. This modified porcine ZPC gene was inserted into the Bam HI—Sal I restriction site of pZ98 to yield the porcine ZPC expression vector, plasmid pZ156 shown in FIG. 3. The $(CAT)_6$ sequence produces a C-terminal hexahistidine $(His_6)$ amino acid sequence in the recombinant fusion protein which permits purification of the fusion protein by immobilized metal in affinity chromatography.

In a similar manner as described above, the plasmid pZ156 when digested with Bam HI and Xho I, may be used to receive any other recombinant ZP gene or gene fragment for expression as a βgal fusion protein which can be purified by metal ion affinity chromatography.

III. Expression of Porcine ZPC Fusion Protein in *E. coli*

The expression vector pZ156 (FIG. 3) was transformed into *E. coli* strain Top 10F' (Invitrogen, San Diego, Calif.) by the procedure of Chung et al., *Proc. Natl. Acad. Sci. USA* 86: 2172–2175 (1989). The transformed *E. coli* cell line was termed Strain ZI 156, and was used to express recombinant porcine ZPC-βgal fusion protein.

Bacterial cultures of ZI 156 were grown in Luria Broth (LB) containing 100 μg/ml ampicillin at 30° C0 until the cell density reached an $OD^{600}$ of approximately 1.5. Isopropyl beta-D-thiogalactopyranoside (IPTG) (3ml of 100 mM solution/l media) was added to induce expression from the tac promoter, and the cells were further incubated at 30° C. for 2–3 hours. The cells were harvested by centrifugation, and the resulting cell pellet was frozen at −70° C.

The frozen cell pellets were suspended in 10 mM EDTA (1 g/2–2.5 ml) and twice sonicated at 50% power for 3 minutes, cooling in an ice bath between each sonication. The cell lysate was then centrifuged at 3300×g for one hour and the hard pellet was retained. This lysis procedure was repeated using the hard pellets.

In order to remove residual EDTA, the final hard cellular pellet was dispersed in a small volume of water by a brief burst of sonication, the suspension was centrifuged, and the supernatant discarded. The washed pellet was thoroughly resuspended in Buffer A, (6M guanidine hydrochloride (GuHCl), 100 mM Na $H_2PO_4$, 10 mM TRIS pH 8, at approximately 0.5 ml per original gram of cell pellet). The suspension was centrifuged at 10,000×g for 45 seconds and the supernatant was retained while the pellet was discarded.

The retained supernatant was loaded onto a Ni column (in Buffer A) and the column was washed with 10 column volumes of Buffer A. The column was next washed with 5 volumes each Buffers B–D, each containing 8M urea, 100 mM $NaH_2PO_4$, and 10 mM TRIS, and having successively reduced pH values of 8, 6.3, 5.9 for Buffers B, C, and D, respectively. The recombinant pZPC-βgal fusion protein eluted with Buffer E, at pH 4.5 as shown by screening by Western Blot analysis using rabbit anti-HSDZ and anti-HSPZ as probes. Further elution may be accomplished using Buffer F (pH 2.5) (8M $GuHCl_2$ 200 mM Acetic Acid).

The fusion protein obtained by this protocol was prepared in its final dose for injection into a host animal by adjusting the final volume to 0.5 ml in 8M urea, and adding it to 0.5 ml adjuvant as described above. Each dose was injected subcutaneously into a test animal.

EXAMPLE 10

Vaccination of Dogs with Recombinant ZPC-β gal Fusion Protein

Eleven mixed breed dogs approximately 5–6 months of age were randomly selected from test animals previously treated at approximately 2 months of age with heat solubilized porcine zona pellucida or chromatographically purified porcine ZP3β in combination with various biopolymers as adjuvants and drug releasing vehicles. Six weeks post first injection, i.e., three and a half months of age, all test animals had achieved antibody titers versus HSPZ in the range of 2–16K as determined by ELISA. However, none of the test animals achieved antibody titers against self-antigen, e. g., HSDZ.

At 5–6 months of age, five of the test animals were then injected with a loading dose of the porcine ZPC-β gal fusion protein prepared as described for Example 9. The recombinant ZPC-β gal fusion protein produced in Example 9 was adjusted to the desired dose in a final volume of 0.5 ml 8M urea and combined with 0.5 ml adjuvant. The adjuvant, N-acetyl-D-glucosaminyl-β(1,4)-N-acetyl muramyl-L-alanyl-D-isoglutamine (GMDP), 250 μg, was dispersed in 0.42 ml mineral oil, 0.157 ml L-121 block polymers, and 0.02 ml Tween 80. Each dose was injected subcutaneously into the five test animals. The remaining 6 animals were maintained as controls.

Following a total of four injections given at 2–3 week intervals, antibody titers versus self antigen, e.g., HSDZ, were obtained in all test animals, with peaks in the range of 2–8 K as measured by ELISA.

Some of the control animals began to cycle beginning at approximately 9 months of age, and by 11 months of age, 4 of 6 control animals had experienced their first estrus. In contrast, none of the 5 test animals which had received recombinant ZPC-β gal fusion protein had cycled during this same time period. However, although the first estrus was delayed for several months in the test animals, they eventually began to cycle. Two of the five vaccinated dogs became pregnant during their second estrus after immunization while a third dog became pregnant during its third estrus after immunization; however, the two remaining test animals remain infertile through three estrus cycles and nearly two years after vaccination.

EXAMPLE 11

Isolation of Human DNA Sequences Encoding Human Zona Pellucida Proteins ZPA and ZPB A human genomic DNA library purchased from Stratagene (catalog no. 946203) was used for the isolation of DNA sequences encoding human ZP proteins. The library consisted of 9–23 kb inserts of human DNA (from placenta tissue of a male Caucasian) cloned into the Lambda Fix™II vector (Stratagene). Approximately 40,000 pfus were plated on *E. coli* strain LE 392 (Stratagene, catalog no. 200266), as described in the Stratagene protocol, but replacing $MgSO_4$ with $MgCl_2$. After overnight incubation, nylon membrane lifts of the plaques were prepared and screened with $^{32}P$-labelled porcine ZPA cDNA (SEQ ID NO. 1) and with $^{32}P$-labelled porcine ZPB cDNA (SEQ ID NO. 3) as described in Example 2.

Three clones 1-1, 2-2, and 4-9 were shown to hybridize to the porcine ZPB cDNA (SEQ ID NO. 3). Clones 1-1 and 4-9 were deposited with the American Type Culture Collection, (ATCC) 12301 Parklawn Drive, Rockville, Md., on Jan. 27, 1993 under ATCC Accession Nos. 75406 and 75405, respectively. Human DNA inserts were isolated from these clones and analyzed by restriction endonuclease digestion with Eco RI and Southern blot analysis as described in Example 1. Table 4 shows the results of Eco RI digestion of these clones.

TABLE 4

HUMAN GENOMIC ZPB EcoRI INSERTS

| Fragment | 1—1 | 2—2 | 4—9 |
| --- | --- | --- | --- |
| A |  | 2.8 kb | 2.8 kb |
| B | 2.2 kb |  |  |
| C | 2.0 kb |  |  |
| D | 1.5 kb |  | 1.5 kb |
| E | 0.2 kb |  | 0.2 kb |
| F | 3.2 kb | 3.2 kb | 3.2 kb |
| G | 0.7 kb |  |  |

Southern blot analysis revealed four Eco RI fragments which were judged to carry ZPB coding sequences based on hybridization to the porcine ZPB cDNA (SEQ ID NO. 3). Clone 1-1 DNA included a 2.2 kb, 2.0 kb, and 1.5 kb Eco RI fragments which so hybridized. Clone 2-2 DNA included a 2.8 kb Eco RI hybridizing fragment. Clone 4-9 DNA included a 2.8 kb and a 1.5 kb Eco RI fragment which hybridized to the porcine ZPB cDNA probe. All inserts additionally included a 3.2 kb non-hybridizing Eco RI fragment; inserts from clones 1-1 and 4-9 both provided 0.2 kb non-hybridizing fragments; and clone 1-1 additionally provided a 0.7 kb non-hybridizing fragment.

Figure 4:
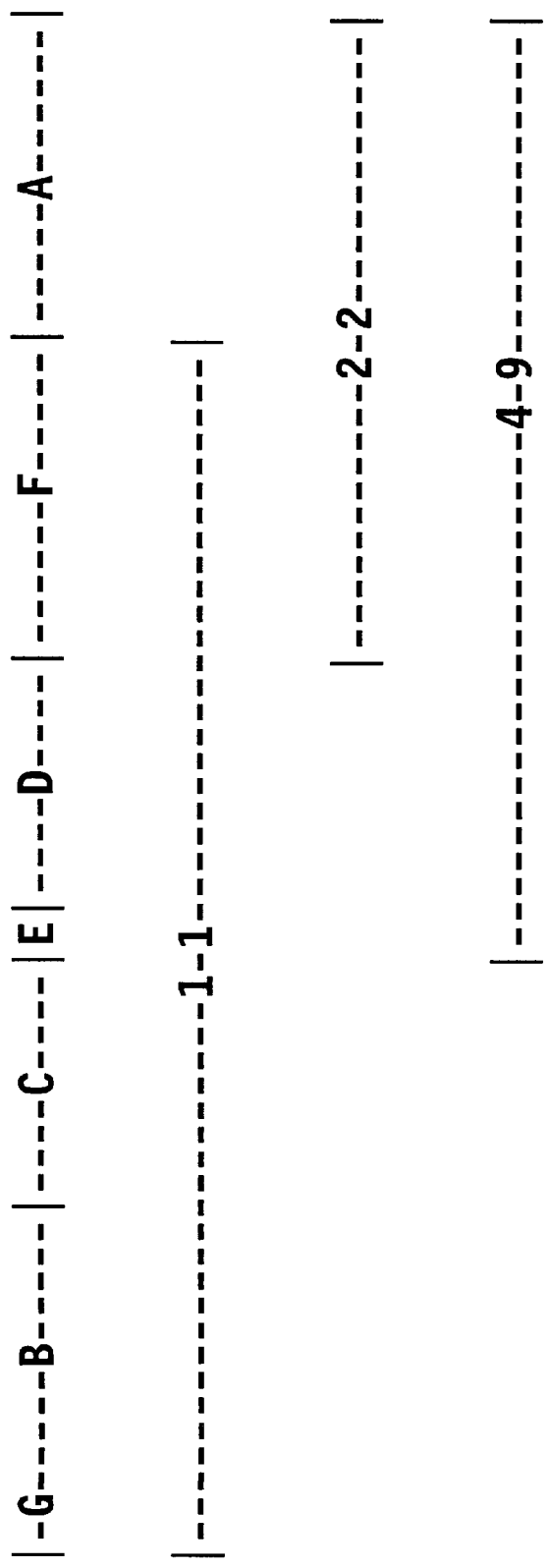
FIG. 4 is a diagrammatic representation of the alignment of the Eco R1 fragments encoding human ZPB.

Further restriction analysis revealed the fragment alignment shown in FIG. 4. Six of the fragments (A–F) were subcloned into pBSKS for sequence analysis, as described in Example 1. Preliminary sequence analysis confirmed the fragment alignment shown in FIG. 4, and suggested that the complete coding sequence of the human ZPB gene may be from clones 1-1 and 4-9. This was confirmed by nucleotide sequence analysis of the inserts, and comparison of the sequences with the feline ZPB sequence (SEQ ID NO. 15) and porcine ZPB sequence (SEQ ID NO. 3). The DNA sequence and deduced amino acid sequences for human ZPB are set out as SEQ ID NO. 40 and 41, respectively.

Clones hybridizing to the porcine ZPA cDNA (SEQ ID NO. 1) under the conditions described in Example 1 were also isolated. Two positive clones, A1 and A4 were identified. The clones were deposited with the American Type Culture Collection, 12301 Parklawn Drive, Rockville, Md. 20852, on Jan. 27, 1993 under ATCC Accession Nos. 75404 and 75403 respectively. Southern blot analysis revealed that these clones contain all or part of the human ZPA gene. DNA was isolated from these clones and was analyzed by Bgl II, Hind III, and Not I restriction endonuclease digestion and Southern blot analysis as described in Example 1. The size of the A1 clone DNA insert is approximately 11.6 kb, and that of the A4 clone is approximately 13.2 kb. Two of the Bgl II fragments which hybridized with the porcine ZPA cDNA (SEQ ID NO 1) were subcloned into pBSKS for sequence analysis, as described in Example 1. Sequence analysis revealed that A1 and A4 collectively contain the human ZPA gene as supported by comparison to sequences with the porcine ZPA cDNA (SEQ ID NO. 1) and the canine ZPA cDNA (SEQ ID NO. 11). The complete DNA sequence and the deduced amino acid sequence are set out as SEQ ID NOS. 42 and 43, respectively.

EXAMPLE 12

Isolation and Sequencing of DNA Encoding Cynomolgus Monkey ZPA, ZPB, and ZPC Cynomolgus monkey cDNA libraries were constructed in λgt10 as described below. Briefly, a set of ovaries were collected from two female cynomolgus monkeys aged 1.5 years and 2 years, and a second set from three females aged 3 years, 4 years, and 14 years of age. Messenger RNA was isolated using the Fast Track™ mRNA isolation kit following the manufacturer's instructions. The cDNA was prepared using the Lambda Librarian™ (Invitrogen, as described in Example 2) kit following the protocol provided with the kit. The cDNA was packaged into lambda phage beads using the Protoclone® (Promega, Madison, Wis.) λgt10 EcoRI arms plus the Packagene® (Promega) lambda DNA packaging system following the manufacturer's instructions. This procedure generally produced libraries with a titer of greater than $1\times10^6$ pfu/ml. The monkey cDNA library was then screened using porcine ZPA, ZPB, and ZPC probes isolated from the porcine cDNA as described in Example 1. Screening was accomplished by preparing duplicate plaque lifts using Nytran® nylon filters (0.2 µM pore size). The filters were prehybridized in a solution of 5× SSPE (43.83 g/l of NaCl, 6.9 g/l of $NaH_2PO_4$, $H_2O$, 1.85 g/l of EDTA, pH 7.4), 5× Denhardts Reagent (1 g/l of Ficoll [type 400], 1 g/l of polyvinylpyrrolidone and 1 g/l bovine serum albumin), 100 µg/ml sonicated, denatured salmon sperm testes DNA, 30% formamide, and 0.5% SDS, for 3 hrs. at 42° C. Radio-labelled probes were prepared using [$\alpha$-$^{32}P$]-dATP and the Prime-a-Gene° (Promega) labelling system. After prehybridization, 10 ng of freshly radio-labelled probe was heat denatured at 95° C. for 5 minutes in 50% formamide and 100 µg/ml sonicated, denatured salmon testes DNA, and was added to the filters. The hybridization was carried out at 42° C. for 15–24 hours. The hybridized filters were then washed twice with 100 ml of 5× SSPE at 55° C., for approximately one hour each wash. The filters were then rinsed in 250 ml of 5× SSPE at 55° C. and allowed to air dry. The dried filters were exposed to x-ray film (Kodak XAR5, Eastman Kodak, Rochester N.Y.) at –70° C. using two intensifying screens (Kodak X-OMATIC™) for at least eight hours. The film was then developed for visual analysis.

Exhaustive screening of the two cynomolgus monkey ovarian cDNA libraries using all of the porcine probes yielded a total of 12 candidate clones. Southern hybridization revealed that only one of these clones (λ CM 4-2) hybridized to the porcine ZPA probe. This clone contained an insert of 560 bp. Sequencing of the insert was performed using the Sequenase® Version 2 kit (U.S. Biochemicals, Cleveland, Ohio) according to the manufacturer's instructions. Sequencing revealed that the 560 bp insert was homologous to the 3' end of other mammalian ZPA genes. The 560 bp fragment represents just under 25% bp of the full-length sequence and contains an open reading frame of 492 bp which would encode a protein of 164 amino acids. The DNA sequence and the deduced amino acid sequence of the cynomolgus monkey ZPA cDNA is set out as SEQ ID NOS. 44 and 45, respectively.

Exhaustive screening of the cynomolgus monkey ovarian cDNA libraries with the porcine ZPB probe yielded a single ZPB candidate clone having an insert of 866 bp. Sequence analysis suggests that the insert includes the C-terminal 50% of the expected full-length sequence. The DNA sequence and deduced amino acid sequence of the monkey ZPB insert are set out as SEQ ID NOS. 46 and 47, respectively. Screening of monkey ovarian cDNA libraries with the porcine ZPC DNA probe yielded only partial ZPC clones, the largest (λ CM1-1) having an insert of approximately 1300 bp which contains just over 50% of the C-terminal portion of the full-length sequence based on comparison to known ZPC clones, (particularly the human ZPC clone). The clone contains an open reading frame of 672 bp which would encode a protein of 224 amino acids. The clone also contains stop codons immediately 5' to the coding sequence in all three reading frames. The DNA sequence and the deduced amino acid sequence of the cynomolgus monkey ZPC clones are set out as sequence ID NOS 48 and 49 respectively.

EXAMPLE 13

Comparison of ZPA DNA and Deduced Amino Acid Sequences

Table 5 shows a comparison of the DNA and deduced amino acid sequence of mammalian ZPAs.

sequences have the most similarity. The high degree of homology between the ZPA genes, as well as between the ZPB (see Example 14) and ZPC (Example 15) genes from a variety of mammalian species, implies a great deal of structural similarity in the ZP layers of these species. However, post-translational modification differences such as glycosylation and others, could represent a potential source of variation.

One protein processing site that all of these ZPA proteins have in common is a furin cleavage site (R-X-R/K-R; Hosaka et al. *J. Biol. Chem,* 266:12127 (1991)) near the C-terminal end of the protein. In fact, with only a few exceptions, all ZP proteins contain a furin processing site near the C-terminus This furin site could serve to cleave off a putative membrane anchor sequence which would allow the processed proteins to move toward the outer edge of the growing ZP layer.

The human ZPA gene contains an exon near the 3' end that is present in the cynomolgus monkey ZPA sequence, but not present in the ZPA genes from other species. This extra exon codes for an amino acid sequence that occurs after the furin processing site, which suggests that the C-terminal fragment generated by furin cleavage might still be important to the function of the ZP layer or to the oocyte in some way.

There are 20 conserved cysteine residues and one or two non-conserved cysteine residues in each of the full-length ZPA sequences. The non-conserved cysteine residues occur either in the N-terminal leader sequence region, or in the extreme C-terminal region of the sequence, where a large amount of the variation between the ZPA sequences occurs. The high degree of homology and the large number of conserved cysteine residues suggests that the tertiary structures of the ZPA proteins are similar.

It has been noted previously that there are regions of homology between the ZPA and ZPB class proteins (Schwoebel et al. *J. Biol. Chem.,* 266:7214 (1991); Lee et al. *J. Biol. Chem,* 268: 12412 (1993); Yurewicz et al. *Biochem. Biophys. Acta* 1174:211 (1993)). Comparison of the human ZPA genomic structure with the human ZPB genomic structure shows these regions to be confined to exons 12, 13, and

TABLE 5

ZPA HOMOLOGY

| | | | | | | PROTEIN HOMOLOGY | | |
|---|---|---|---|---|---|---|---|---|
| | Mouse | Rabbit | Pig | Cow | Dog | Cat | Monkey | Human |
| Mouse | — | 61.0% | 54.2% | 60.8% | 57.9% | 56.9% | 57.2% | 58.9% |
| Rabbit | 73.0% | — | 63.0% | 69.8% | 66.2% | 64.6% | 65.1% | 68.9% |
| Pig | 69.0% | 75.6% | — | 79.9% | 69.6% | 70.2% | 56.9% | 63.9% |
| Cow | 70.5% | 79.0% | 86.2% | — | 78.3% | 77.8% | 59.0% | 63.6% |
| Dog | 70.4% | 77.2% | 80.4% | 84.8% | — | 83.1% | 66.9% | 67.5% |
| Cat | 69.6% | 77.5% | 81.3% | 84.7% | 88.9% | — | 65.5% | 67.4% |
| Monkey | 56.7% | 59.6% | 56.6% | 57.0% | 59.2% | 58.4% | — | 95.8% |
| Human | 68.4% | 74.6% | 73.7% | 63.1% | 74.4% | 75.3% | 96.3% | — |
| DNA HOMOLOGY | | | | | | | | |

Data is presented as a cross-wise comparison of the ZPA protein and DNA sequences. The comparison of the protein sequences are shown in the upper right hand side of the table, above the diagonal dashed lines. The comparison of the DNA sequences are shown in the lower left hand side of the table, below the diagonal dashed lines. The ZPA DNA and deduced amino acid sequences are highly homologous between species. The homology is highest between members of the same order within the class *mammalia*. For example, the human and cynomolgus monkey (*primata*), the pig and cow (*ungulata*), and the cat and dog (*carnivora*) 14 of the human ZPA gene and exons 5, 6, and 7 of the human ZPB gene. This suggests that this homology might be due to a partial ancestral gene duplication. The ZPB proteins contain 21 conserved cysteine residues. The first 11 of these do not align with those in the ZPA proteins, but the last 10 match well. This extends the homology to approximately 270 amino acids, covering exons 11–16 of the ZPA gene and exons 4–9 of the ZPB gene, although the overall homology of the expanded region is slightly lower (approximately 43%). The remainder of the ZPA and ZPB genes show very little homology with each other, and the ZPC genes also show no extensive homology to the ZPA genes. In addition, the ZPA gene has no extensive sequence similarity to non-ZP nucleic acid and protein sequences in Genbank and the SwissProt data banks.

EXAMPLE 14

Comparison of ZPB DNA and of Deduced Amino Acid Sequences

Table 6 shows the comparison of the six known ZPB DNA and protein sequences (the bovine and cynomolgus cDNA fragments are only compared to the corresponding regions of the other full-length ZPB sequences).

TABLE 6

ZPB HOMOLOGY

|  | Rabbit | Bovine | Porcine | Feline | PROTEIN HOMOLOGY C. Monkey | Human |
|---|---|---|---|---|---|---|
| Rabbit | — | 75.3% | 65.3% | 60.1% | 70.2% | 65.2% |
| Bovine | 78.8% | — | 82.3% | 71.2% | 69.9% | 69.6% |
| Porcine | 74.2% | 86.2% | — | 63.7% | 63.6% | 63.1% |
| Feline | 69.5% | 78.7% | 72.9% | — | 70.3% | 64.6% |
| C. Monkey | 78.9% | 78.5% | 78.2% | 78.6% | — | 92.3% |
| Human | 74.3% | 80.8% | 73.3% | 74.2% | 95% | — |

DNA Homology

The data are presented as cross-wise comparison of the ZPB protein and DNA sequences. The comparison of the protein sequences are shown in the upper right hand side of the table, above the diagonal dashed lines. The comparison of the DNA sequences are shown in the lower left hand side of the table, below the diagonal dashed lines.

The data shows considerable ZPB homology among members of different mammalian species. As was the case with ZPA, this homology is most pronounced between members of the same order within the class *mammalia*. For example, the human and cynomolgus monkey sequences (*primata*) and the pig and cow sequences (*ungulata*) have the most homology to each other. With only a few exceptions (noted below), the ZPB sequences show no homology to other DNA or protein sequences in the GenBank or SwissProt databases. Hybridization experiments suggest that the ZPB transcripts are ovary specific.

Comparisons of the deduced amino acid sequences of the ZPB clones show more divergence within this genetic group than within the ZPA and ZPC groups. Comparison of the rabbit ZPB and porcine ZPB shows the sequences to be predominantly collinear (74% homologous) except that the rabbit has an additional upstream ATG codon which adds six codons to the rabbit sequence.

The feline ZPB sequence has two additional amino acid inserts, which total 38 additional codons, in the first quarter of the gene, compared to the porcine and rabbit sequences. Both inserts occur just after cysteine residues, which suggests that if the cysteines are involved in disulfide bridges, these regions might form unique epitopes. However, the feline gene is still 73% homologous to porcine gene and 70% homologous to the rabbit gene.

The human gene has a sequence homologous to the first of the inserts in the cat sequence, but not the second. However, there are consensus splice site donor and acceptor sequences adjacent to this extra region in the human sequence, which if used would leave the coding sequence in frame. Therefore, the sequence representing exon 2 could actually be two small exons (122 and 103 bp) separated by a small intron (84 bp). This would make the human sequence in this region identical to the pig sequence. The first extra region in the cat sequence is also flanked by in frame splice site donor and acceptor signals. If the extra region was removed from the cat sequence, it would differ from the pig sequence by only a single amino acid. However, the cat sequence was obtained from a cDNA clone made from an mRNA that appears to be fully processed. The second extra region in the cat sequence does not contain in frame splice site donor or acceptor signals, and therefore is probably not due to the presence of an unprocessed intron.

The cynomolgus monkey and human sequences have an additional seven codons at the C-terminus when compared to the other ZPB sequences. In the cynomolgus monkey, this is due to a two-base pair deletion, which causes a frameshift mutation which puts the termination codon used by the other species out of frame. The human sequence also contains this deletion, but in addition, there is also a base change that eliminates this termination codon.

There are 21 conserved cysteine residues in the ZPB proteins, the final 10 of which occur in a region that has homology to the ZPA proteins. This homology was noted previously (Schwoebel et al., supra; Lee et al. supra, 1993; Yurewicz et al. supra, 1993), but examination of the genomic structure of the human ZPA and ZPB genes allowed the homology to be extended to approximately 270 amino acids. This homology could be due to a partial ancestral gene duplication. In addition to the conserved cysteine residues, the pig ZPB protein contains one additional cysteine residue in the putative leader sequence, and the human sequence contains four additional cysteine residues. The first of these is in the putative leader sequence (in a different location than pig), the second is in the region containing the additional insert, and the last two are in the C-terminal extension caused by the mutated termination codon. These last two extra cysteine residues are conserved in the cynomolgus monkey sequence.

All of the ZP proteins contain a putative transmembrane domain near the C-terminus. However, the canonical furin proteolytic processing signal (R-X-R/K-R, Hosaka et al. supra, 1991), which occurs just prior to the transmembrane domain in all of the ZPA and ZPC proteins, is altered in the human (S-R-R-R), cynomolgus monkey (S-R-R-N) and rabbit (S-R-R-R) ZPB sequences. The significance of this is unknown, but it may indicate that these proteins are processed by a related system with specificity for di- or tribasic sequences, since the release of the putative transmembrane domain would be necessary for the ZPB protein to move as the ZP layer grows. There appears to be a great deal of proteolytic processing of the pig ZPA and ZPB (Yurewicz et al. supra,) proteins. There is no data concerning the post-translational modification of the ZPB proteins of cat, cow, cynomolgus monkey or human. The physiologic significance of this processing is unknown, but differential processing would present an avenue of variation among species of the highly conserved ZP proteins.

There is a question of whether humans actually transcribe the ZPB gene. Since the amount of human ovarian mRNA recovered was so small, there was not enough RNA to both construct a cDNA library and perform a Northern analysis. However, since cynomolgus monkey transcribes the ZPB gene, it is probable that the highly homologous human ZPB gene is also transcribed.

The apparent lack of a ZPB cDNA in the dog cDNA library is another puzzle. All of the libraries screened which contained any zona pellucida gene contained all three genes, except the dog. However, mRNA isolated from the ovary of a six-month old dog (the library was made from the ovary of a four-month old dog), includes a ZPB mRNA that comigrates with the porcine and cynomolgus monkey ZPB mRNA on a Northern blot. One possibility to explain the lack of a canine ZPB cDNA is that the transcriptional timing of the three ZP genes is spread out, and since the ovary used to make the library was young, the transcription of the ZPB gene occurs later than the ZPA and ZPC genes (Andersen and Simpson, 1973).

EXAMPLE 15

Comparison of ZPC DNA and Deduced Amino Acid Sequences

Table 7 shows the comparison of the DNA and deduced amino acid sequences from all of the ZPC cDNAs and genes.

ZPA and ZPB, cleavage by furin of the ZPC proteins would remove a putative membrane anchor sequence (Klein et al., 1985), which would allow the processed ZPC protein to move toward the outer layer of the expanding oocyte. Therefore, this sperm-binding site probably represents the C-terminus of the mature proteins. However, there is very little homology (even between hamster and mouse) in the regions of the ZPC proteins corresponding to this epitope. This might indicate that this region contributes to the species specificity of sperm-egg binding.

The variation that is seen at the C-terminus of the ZPC proteins occurs in the putative transmembrane region. This variation could indicate that this amino acid sequence is less important than the overall hydrophobicity of the amino acids in this region, similar to the lack of homology seen in leader sequences. However, it is also possible that this variation signifies a species-specific function for this region.

TABLE 7

ZPC HOMOLOGY

|  | Mouse | Hamster | Rabbit | Pig | Cow | Dog | Cat | Monkey | Human |
|---|---|---|---|---|---|---|---|---|---|
|  |  |  |  |  |  |  | PROTEIN HOMOLOGY | | |
| Mouse | — | 78.8% | 65.9% | 65.6% | 64.0% | 64.7% | 63.3% | 64.4% | 67.0% |
| Hamster | 84.7% | — | 65.9% | 65.6% | 63.5% | 65.1% | 63.6% | 68.2% | 68.0% |
| Rabbit | 70.1% | 71.3% | — | 68.2% | 68.5% | 65.3% | 64.1% | 59.4% | 68.5% |
| Pig | 71.5% | 72.0% | 74.6% | — | 83.6% | 75.7% | 72.8% | 69.2% | 73.7% |
| Cow | 70.5% | 71.4% | 74.5% | 86.5% | — | 74.5% | 72.8% | 67.4% | 71.1% |
| Dog | 70.1% | 71.9% | 71.5% | 79.8% | 80.3% | — | 79.2% | 66.5% | 70.1% |
| Cat | 70.9% | 71.6% | 73.0% | 79.3% | 80.0% | 84.3% | — | 71.1% | 70.5% |
| Monkey | 72.4% | 74.1% | 71.3% | 76.6% | 77.2% | 73.8% | 77.8% | — | 90.6% |
| Human | 74.1% | 75.0% | 76.2% | 80.0% | 79.6% | 77.7% | 78.8% | 94.4% | — |
| DNA HOMOLOGY | | | | | | | | | |

The data are presented as a cross-wise comparison of the ZPC protein and DNA sequences. The comparison of the protein sequences are shown in the upper right hand side of the table, above the diagonal dashed lines. The comparison of the DNA sequences are shown in the lower left hand side of the table, below the diagonal dashed lines.

ZPC proteins and DNA sequences show a higher degree of homology than the ZPA and ZPB DNAs and proteins. As was the case with ZPA and ZPB, the homology is most pronounced in members of the same order within the class *mammalia*; the human and cynomolgus monkey sequences (*primata*), the cat and dog sequences (*carnivore*), the pig and cow sequences (*ungulata*), and the mouse and hamster sequences (*rodenta*). The ZPC transcripts are ovary specific, based on Northern blot analysis and comparison to the sequences in the GenBank and SwissProt databases detects no significant non-ZP homology. Comparison of the deduced amino acid sequences of the known ZPC genes detects three regions that contain large numbers of non-consensus sequences. These regions are: the putative leader sequences and the first 20–25 amino acids of the mature protein; the region containing the peptide that was identified as a sperm-binding region in the mouse (Millar et al. *Science* 216:935–938 (1989)); and the C-terminal region of the proteins that might be removed from the mature protein at the furin processing site (see below).

The epitope identified as a putative sperm-binding site (Millar et al. supra, 1989) occurs immediately before a furin proteolytic cleavage site (Hosaka et al., 1991). The furin site (R-X-R/K-R) is highly conserved in all of the ZPC sequences. However, it should be noted that the canine ZPC sequence contains a second furin site, 19 amino acids upstream from the first furin site. Also as is the case with Each ZPC sequence contains 14 conserved cysteine residues, but each sequence also has one or two extra cysteine residues that are shared only with one or a few other sequences. These extra cysteine residues are near the N- or C-terminus of the proteins, where the greatest sequence variation exists. However, the large number of conserved cysteine residues probably indicates that the overall structure of the central core of all of these proteins is quite conserved.

EXAMPLE 16

Immunization of Cynomolgus Monkeys With HSPZ

A sexually mature cynomolgus monkey was immunized with HSPZ to test the ability of HSPZ to induce infertility. HSPZ was prepared as described in Example 6. HSPZ was mixed with the following GMDP/oil adjuvant. 50 μg GMDP (N-acetyl-D-glucosaminyl-(β1–4)-N-acetylmuramyl-D-isoglutamine) (CC. Biotech, Poway, Calif.); 42.1 of mineral oil, 15.8% pluronic VC-121 (block polymer polyols, BASF-Wyandotte, Parsippany, N.J.). The animal received a series of 4 subcutaneous injections of 1 mg of HSPZ in the GMDP/oil adjuvant beginning with a priming dose followed four weeks later by a booster dose, which was followed by two booster doses five weeks apart which were followed six weeks later by a final dose. This dosage regimen resulted in an anovulatory monkey having antibody titers against its cynomolgus monkey heat-solubilized zona pellucida prepared as described for HSPZ. The peak antibody titers to cynomolgus monkey HSPZ were 1:8000–1:16,000.

A fractionated preparation of HSPZ which is essentially native porcine ZPA and ZPB was prepared by isoelectric focusing, as described in Example 6 and was used to vaccinate cynomolgus monkeys using 1 mg of fractionated HSPZ in GMDP/oil injected subcutaneously according to the following schedule: a priming dose was given followed approximately 6 weeks later by a booster dose followed by a final booster dose 11 weeks after the previous booster dose. The immunized monkeys achieved peak antibody titers of 1:4,000–1:8,000 against monkey heat-solubilized zona pellucida while maintaining a regular ovulatory cycle. However, despite maintaining a regular ovulatory cycle, the monkeys remained infertile until their antibody titers to monkey heat-solubilized zona pellucida fell below 1:500 after which the animals became pregnant upon breeding.

Immunization of cynomolgus monkeys with recombinant baculovirus produced canine ZPC and porcine ZPC (prepared as described in Example 18) failed to induce infertility despite inducing antibody production against monkey heat-solubilized zona pellucida. One possible explanation for this is that the glycosylation pattern of ZP proteins produced in the baculovirus system may prevent recognition of the epitopes responsible for induction of infertility.

Bacterially produced porcine ZPA, ZPB, and ZPC described above administered to cynomolgus monkeys failed to induce detectable antibody titers against cynomolgus monkey heat-solubilized zona pellucida even though antibody titers against the presented antigens were produced.

EXAMPLE 17

Mapping of Mammalian Zona Pellucida Protein Epitopes

A Pin Technology™ Epitope Scanning Kit purchased from Chiron Mimotopes U.S., Emeryville, Calif. (Catalog No. PT-02-20000A) was used for mapping epitopes in Zona Pellucida proteins. The procedures described in the kit manual were followed, with the exception of modifications in the ELISA testing procedure (described below).

Briefly, Pin Technology software was installed in a United Business Machines 486/33 computer according to the manufacturer's instructions. The protein sequence was entered into the computer program, the desired peptide length, and degree of overlap between peptides were selected, and a protocol containing the daily requirements of activated protected amino acid derivatives and their location in the coupling tray wells was printed. Prior to use, the pins were first washed once with dimethylformamide (DMF), and then with methanol three times, each wash lasting for two minutes. The pin block was air dried and the pins were deprotected by agitation in a 20% mixture of piperidine in DMF at room temperature for 30 minutes. The pins were washed again as described above, except that the washes were for 5 minutes each, and the pin block was then air dried. The required amino acid derivative solutions were prepared and dispensed into the wells of the synthesis tray according to the protocol for the current cycle. The dried mimotope pins were washed once more in a DMF bath for 5 minutes and then positioned appropriately in the wells of the synthesis tray. The assembly was then sealed in a plastic bag and incubated at 30° C. for approximately 22 hours. On the following day, the pin block was removed from the coupling tray and subjected to the same cycle of washing, deprotection, and coupling steps as outlined above; however, using the amino acid derivatives and their tray location appropriate to the next cycle. The foregoing cycle of washing, deprotection, washing, and coupling was repeated until the peptide sequences were completed.

After coupling the terminal amino acids of the peptides, the pin block was washed, air dried, deprotected, washed and air dried as before. The terminal amino groups of the peptides were then acetylated by immersion of the pins in a mixture containing 5 parts DMF, 2 parts acetic anhydride, and 1 part triethylamine, by volume, dispensed in the wells of a polypropylene coupling tray, and incubating at 30° C. for 90 minutes. The pin block was removed, subjected to another washing sequence as before, and air dried.

Side chain deprotection of the peptides was performed by agitating the pin block in a mixture containing 95 parts trifluoroacetic acid, 2.5 parts anisole, and 2.5 parts ethanedithiol, by volume, at room temperature for 4 hours. The pin block was then air dried for approximately 10 minutes, sonicated in a bath containing 0.1% hydrochloric acid in a mixture containing equal parts of methanol and deionized water, by volume, for 15 minutes, and finally air dried.

Prior to ELISA testing, the pins were subjected to a disruption procedure involving sonication in a bath consisting of a mixture containing 39 parts sodium dihydrogen orthophosphate, 25 parts sodium dodecyl sulfate, 0.1 part 2-mercaptoethanol, and 2500 parts deionized water, by weight, adjusted to pH 7.2 with 50% sodium hydroxide solution. The sonication was performed at 55 to 60° C. for approximately 45 minutes. The pin block was then washed by immersion with gentle agitation in three sequential baths of deionized water at 60 degrees for three minutes each. Finally, the pin block was immersed in gently boiling methanol for approximately 4 minutes and then air dried.

Preparation of Antisera

Antisera directed against zona pellucida proteins was prepared by immunizing the appropriate animals with the appropriate zona pellucida protein using procedures well known in the art and described in E. Harlow and D. Lane in Antibodies, A Laboratory Manual, Chapter 5,. Cold Spring Harbor Laboratory, 1988 which is incorporated herein by reference. Biotinylated antisera was prepared by a modification of the procedure described in Harlow supra (page 314). Briefly, to a solution containing between 1 and 3 mg per ml of the selected antibody IgG fraction in phosphate buffer with saline (PBS) at pH 7.2 was added a solution containing 25 to 250 micrograms biotinamidocaproate, N-hydroxysuccinimide ester (Sigma, Cat No. B2643) in dimethyl sulfoxide at a concentration of 10 mg/ml. The mixture was mixed well and then incubated at room temperature for 4 hours. One molar ammonium chloride solution in the amount corresponding to 20 microliters per 250 micrograms biotin ester was added, and the resulting mixture was incubated at room temperature for 10 minutes. Unreacted biotin ester was then removed by extensive diafiltration with PBS using a Centricon-30 (TM) microconcentrator devices (Amicon Division, W. R. Grace & Co., Inc., Beverly Mass.). The dilution factor for the resulting conjugate was determined by ELISA titration against the appropriate native protein.

ELISA Testing

A modification of the procedure described in the Epitope Scanning Kit manual was employed.

After disruption, the mimotope pins were blocked by incubation with "supercocktail" (10 g ovalbumin, 10 g bovine serum albumin, and 1 ml Tween 20 detergent per liter of PBS) at room temperature for 1 hour. This was followed by incubation at room temperature for 2 hours with appropriately diluted biotinylated antisera. The pins were washed 4 times with PBS containing 0.5% Tween 20 (PBST) at room temperature for 10 minutes each time, with agitation.

The pins were then incubated at room temperature for 1 hour with the secondary antibody, horseradish peroxidase-streptavidin conjugate (Zymed Laboratories, Inc., South San Francisco, Calif.) diluted 1:2500 with PBST. They were washed again as described above.

Substrate buffer was prepared by combining 200 ml 1.0 M. disodium hydrogen orthophosphate solution with 160 ml 1.0 M. citric acid solution, diluting the mixture with 1640 ml deionized water, and adjusting to pH 4.0 using either citric acid or sodium hydroxide solutions. Substrate solution was prepared by dissolving 10 mg 2,2'-azino-bis(3-ethylbenzthiazoline-6-sulfonic acid) diammonium salt in 20 ml substrate buffer and adding 6 microliters 30% hydrogen peroxide. The mimotope pins were incubated at room temperature with this solution, using microtiter plates containing 150 microliters per well. When color development appeared to be appropriate for measurement by an ELISA plate reader, the pin block was removed and the plate was read at a wavelength of 450 nm. The pin block was then disrupted by the procedure described above.

The data were entered into the Pin Technology™ computer program, which performed statistical analysis and evaluation and furnished a print-out of the results identifying the strongest binding epitopes. Briefly, the 25% of the wells having the lowest optical density readings were assumed to represent background in each experiment. The mean value and the standard deviation of these readings were calculated. Significant recognition of peptides by antisera was attributed to the pins corresponding to those wells showing absorbance readings greater than the sum of the background mean and three standard deviations from the mean.

Human ZPA epitopes were examined for reactivity with mouse anti-human ZP antiserum prepared as described above. Peptides of 15 amino acids in length were synthesized beginning with amino acid number 1 as illustrated in SEQ ID NO. 43. Successive peptides having a 7-amino acid overlap with the preceding peptide of the series were synthesized. The following peptides were shown to bind mouse anti-human ZP antiserum: 1–15, 9–23, 25–39, 33–47, 65–79, 81–95, 89–103, 97–111, 105–119, 113–127, 121–135, 129–143, 145–159, 153–167, 161–175, 193–207, 209–223, 217–231, 225–239, 241–255, 249–263, 273–287, 281–295, 289–303, 305–319, 313–327, 321–335, 329–343, 337–351, 345–359, 385–399, 393–407, 401–415, 409–423, 417–431, 425–439, 441–455, 449–463, 457–471, 481–495, 489–503, 497–511, 505–519, 513–527, 521–535, 537–551, 545–559, 561–575, 569–583, 577–591, 585–599, 601–615, 609–623, 617–631, 625–639, 633–647, 641–655, 665–679, 697–711, 705–719, 713–727, 721–735, and 729–743.

Similarly, human ZPB epitopes were mapped using mouse anti-human ZP antiserum. In these experiments, 15 amino acid peptides were synthesized beginning with amino acid number 1 as set out in SEQ ID NO. 41. The overlap between successive peptides in this case was 9 amino acids. The following peptides were shown to bind mouse anti-human ZP antiserum: 7–21, 25–39, 31–45, 49–63, 67–81, 73–87, 79–93, 91–105, 103–117, 121–135, 193–207, 205–219, 211–225, 217–231, 223–237, 229–243, 253–267, 259–273, 265–279, 283–297, 289–303, 295–309, 301–315, 307–321, 313–327, 319–333, 343–357, 349–363, 355–369, 367–381, 373–387, 379–393, 385–399, 403–417, 409–423, 415–429, 421–435, 433–447, 439–453, 445–459, 451–465, 481–495, 487–501, 499–513, 505–519, 511–525, 523–537, 529–543, and 547–561.

Human ZPC epitopes were mapped using mouse anti-human ZP antiserum. In these experiments, the 15 amino acid peptides were synthesized beginning with amino acid number 1 as set out in Chamberlin et al., *Proc. Nat'l Acad. Sci. USA* 87:6014–6018 (1990) which is incorporated herein by reference see SEQ ID NOS. 60 and 61). The overlap between successive peptides was 10 amino acids. The following peptides were shown to bind mouse anti-human ZP antiserum: 21–35, 51–65, 116–130, 146–160, 151–165, 181–195, 241–255, 251–265, 271–285, 296–310, 321–335, 401–415, and 411–425.

Canine ZPC epitopes were mapped using rabbit anti-canine ZP antiserum. In these experiments, the 15 amino acid peptides were synthesized beginning at amino acid number 1 set out in SEQ ID NO. 10. The overlap between successive peptides was 5 amino acids. The following peptides were shown to bind rabbit anti-canine ZP antiserum: 51–65, 61–75, 81–95, 131–145, 181–195, and 301–315.

Feline ZPC epitopes were mapped using rabbit anti-feline ZP antiserum. In these experiments, the 15 amino acid peptides were synthesized beginning at amino acid number 1 as set out in SEQ ID NO. 18. The overlap between successive peptides was 5 amino acids. The following peptides were shown to bind rabbit anti-feline ZP: 36–50, 46–60, 56–70, 76–90, 96–110, 106–120, 116–130, 126–140, 136–150, 146–160, 156–170, 186–200, 196–210, 246–260, 266–280, 276–290, 286–300, 296–310, 316–330, 326–340, 336–350, 346–360, 376–390, 396–410, and 406–420.

Bovine ZPC epitopes were mapped using rabbit anti-bovine ZP antiserum. In these experiments, the overlapping 15 amino acid peptides were synthesized beginning at amino acid number 1 as set out in SEQ ID NO. 24. The overlap between peptides was 10 amino acids. The following peptides were shown to be reactive with rabbit anti-bovine ZP antiserum: 1–15, 31–45, 51–65, 56–70, 61–75, 76–90, 106–120, 111–125, 116–130, 121–135, 131–145, 136–150, 141–155, 146–160, 151–165, 161–175, 181–195, 186–200, 191–205, 196–210, 201–215, 206–220, 216–230, 226–240, 241–255, 246–260, 261–275, 266–280, 271–285, 276–290, 291–305, 296–310, 301–315, 316–330, 321–335, 326–340, 331–345, 336–350, 341–355, 356–370, 361–375, 376–390, 381–395, 386–400, 396–410, 401–415, and 406–420.

EXAMPLE 18

Immunization of Dogs with Recombinant ZPC Proteins

Dogs were immunized with various preparations of recombinant canine ZPC. The plasmid pZ169 bacterial expression vector (FIG. 5) was constructed as follows. The parent vector pZ98 (described in Example 9) was digested with the restriction enzymes PvuI and Bam HI, and the large fragment was gel purified. Into this vector was ligated a fragment created by annealing the following oligonucleotides:
5'CGCCCTTCCCAGCAACTGCACCATCAC-CACCATGG 3' (SEQ ID NO. 50); and
5'GATCCCCATGGTGGTGGTGATGGTG-CAGTTGCTGGGAAGGGCGAT 3' (SEQ ID NO. 51).
These oligonucleotides create a fragment with PvuI and BamHI ends, and codes for the hexapeptide sequence His6. This intermediate vector was digested with the restriction enzymes BamHI and EcoRI, and the large fragment was gel purified. Into this vector was ligated a fragment created by annealing the following oligonucleotides:
5'GATCCCTCGAGCCACCATCACCACCATCATG 3' (SEQ ID NO. 52); and
5'AATTCATGATGGTGGTGATGGTGGCTCGAGG 3' (SEQ ID NO. 53).

These oligonucleotides create a fragment with BamHI and EcoRI ends and an XhoI site just downstream of the BamHI site, and which codes for the hexapeptide sequence His$_6$. This new vector was named pZ88, and contains unique BamHI and XhoI cloning sites between two His6 sequences. To create pZ169, the pZ88 vector was digested with the restriction enzymes BamHI and XhoI, and the large fragment was gel purified. Into this vector was ligated a fragment generated by performing a PCR (polymerase chain reaction) of the canine ZPC cDNA using the following oligonucleotides:

5'CCCGGATCCGCAGACCATCTGGCCAACTGAG 3' (SEQ ID NO. 54); and
5'GCGCTCGAGGGCATATGGCTGCCAGTGTG 3' (SEQ ID NO. 55).

Figure 5:
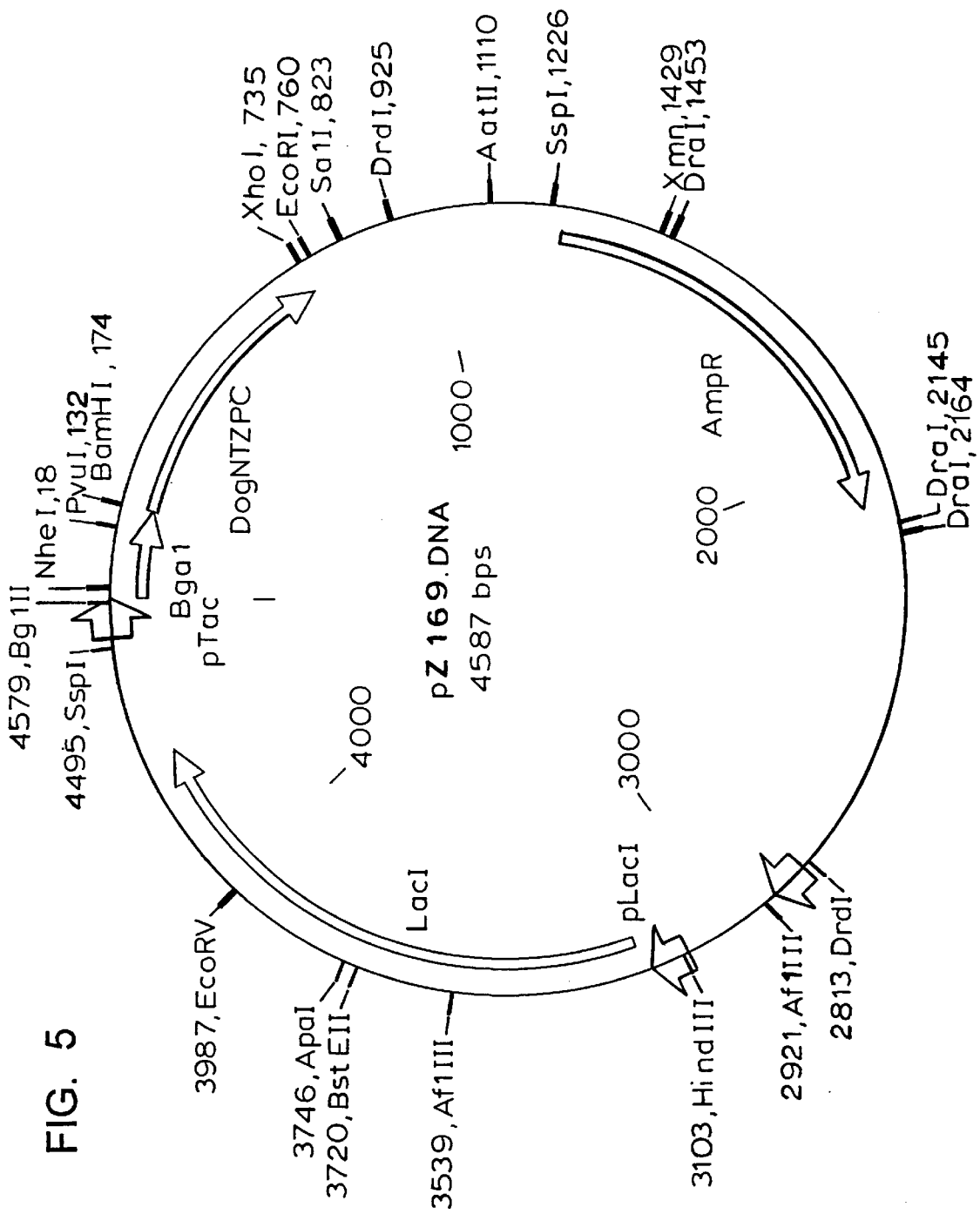
FIG. 5 is a diagrammatic representation of the plasmid vector pZ169.

This PCR creates a fragment containing amino acids 23–207 of the canine ZPC sequence, with BamHI and XhoI ends. This new vector is named pZ169, (FIG. 5) and produces a protein containing amino acids 1–56 of the *E. coli* β-galactosidase sequence, His$_6$, amino acids 23–207 of the canine ZPC sequence, His$_6$, and amino acids 1006–1023 of the *E. coli* β-galactosidase sequence. This protein is referred to as N-terminal canine ZPC. In FIG. 5, pTAC refers to the tac promoter described above; AmpR refers to an ampicillin resistance marker, ori is an *E. coli* origin of replication sequences and pLacI is the lacI promoter which drives expression of the lacI gene.

Recombinant canine ZPC was produced and purified as described in Example 9. A baculovirus expression vector pZ145 was constructed as follows. The parent vector pBlueBac2 (purchased from Invitrogen Corporation, San Diego, Calif.) was digested with the restriction enzymes NheI and BamHI, and the large fragment was gel purified. Into this vector was ligated a fragment generated by a PCR of the porcine ZPC cDNA using the following oligonucleotide:

5'CGCGCTAGCAGATCTATGGCGC-CGAGCTGGAGGTTC 3' (SEQ ID NO. 56); and
5'CGCGGATCCTATTAATGGTGGTGATG-GTGGTGACTAGTGGACCCTTCCA 3' (SEQ ID NO. 57).

This PCR creates a fragment with NheI and BamHI ends, and contains amino acids 27–350 of the porcine ZPC sequence followed by an SpeI site and the hexapeptide His$_6$. This new vector is named pZ147. To create the pZ145 vector, pZ147 is digested with NheI and SpeI and the large fragment is gel purified (this removes the pig ZPC sequence). Into this vector was ligated a fragment generated by a PCR of the canine ZPC cDNA using the following oligonucleotides:

5'CCCGCTAGCAGATCTATGGGGCTGAGC-TATGGAATTTTC 3' (SEQ ID NO. 58); and
5'CGCACTAGTTGACCCCTCTATACCATGATCACTA 3' (SEQ ID NO. 59).

Figure 6:
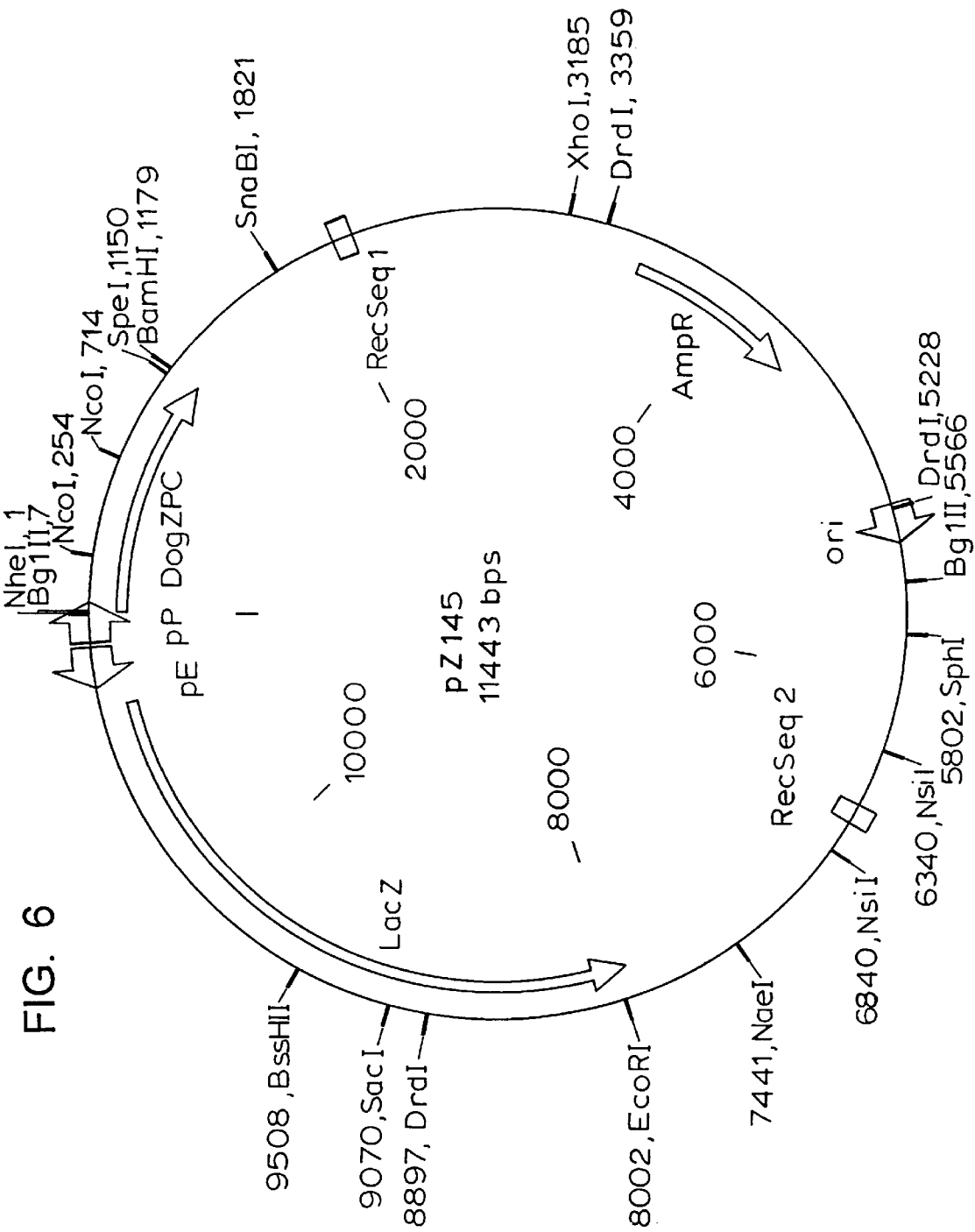
FIG. 6 is a diagrammatic representation of the plasmid vector pZ145.

This PCR creates a fragment with NheI and SpeI ends, and contains amino acids 1–379 of the canine sequence. Transformants of this ligation were screened for the presence of the inserted NheI/SpeI fragment in the correct orientation (since the NheI and SpeI sticky ends are identical). This new vector is named pZ145, (FIG. 6) and produces a protein containing amino acids 1–379 of the DZPC sequence followed by His$_6$. This protein is referred to as baculo-canine ZPC. In FIG. 6, pP represents the baculovirus polyhedrin promoter, AmpR represents an ampicillin resistance marker, LacZ represents the gene for β-galactosidase, pE is a constituitive promoter which drives the expression of LacZ and ori is the *E. coli* origin of replication.

Recombinant baculovirus derived canine ZPC was produced by co-transfecting insect SF9 cells with pZ145 and *Autographica californica* multiply enveloped nuclear polyhedrosis virus (AcMNPV) using methods well known in the art as described in the MAXBAC™ kit purchased from Invitrogen, San Diego, Calif. Recombinant canine ZPC produced in SF9 cells was prepared from cotransfected SF9 cells as follows. Cotransfected cells were harvested and pelleted by centrifugation and recombinant canine ZPC was purified as was described in Example 9 for purification from a cell pellet. Recombinant canine ZPC may also be isolated from the culture medium and purified on a Ni-column as described in Example 9.

Other expression vectors which are capable of expressing zona pellucida encoding nucleotide sequences under the control of a variety of regulatory sequences are within the scope of the present invention and are readily constructed using methods well known in the art.

Recombinant zona pellucida proteins may also be modified to increase their potential antigenicity by a variety of methods well known in the art. For example, a recombinant dog ZPC was modified by palmitylation was prepared as follows. Approximately 1 mg of recombinant ZPC produced using the plasmid pZ169 as described above was brought to a final concentration of 8M urea (total volume 0.2–0.3 mls.). A palmitylation solution (Pl$_2$O/TEA) was then prepared by adding palmitic anhydride to triethylamine to give a final concentration of palmitic anhydride of 20 mg/ml of triethylamine.

Approximately 10 µl of Pl$_2$O/TEA solution was added to 1 mg of recombinant canine ZPC in 8M urea (described above). The mixture was allowed to stand at room temperature for a least two hours after which the preparation was ready for mixture with GMDP/oil adjuvant.

Chitosan modification is another useful modification of canine ZPC for the practice of the present invention. Briefly, 1.5 ml of sterile mineral oil was added to 1.5 ml of recombinant canine ZPC solution prepared as described above using the plasmid pZ169 (2 mg/ml ZPC, 3 mg total is 8M urea) was mixed with 5 drops of Arlacel A (mannide monooleate, Sigma, St, Louis, Mo.). Subsequently, 0.75 ml of Chitosan (2% wt/vol. is 0.5M sodium acetate, pH 5.0) was added, and the mixture was sonicated for 10–20 seconds, followed by the addition of 0.045 ml of 50% NaOH and another round of sonication for 10–20 seconds. Finally, 10 µl of 10 mg/ml GMDP/8M urea was added.

A group of three dogs was immunized five times each at one-month intervals with subcutaneous injections of 1 mg doses of the N-terminal canine ZPC modified by the addition of chitosan prepared as described above. Immunized dogs developed antibody titers of 1:8000–1:16000 against heat solubilized dog zona pellucida (self-titers) using methods described above. The estrus cycle of the dogs showing self-titers was anovulatory and prolonged (4–6 weeks instead of the normal 10-day to 14-day cycle for normal dogs). Of the three immunized dogs, two have experienced their first estrus; one of the two dogs exhibited estrus six months after the first immunization and was bred and found to be infertile. The second of the two dogs experienced estrus and remained infertile nine months after the first immunization. The third dog has yet to experience estrus more than nine months after immunization.

Another group of four dogs were immunized three times at one-month intervals using 1 mg doses of palmitylated canine ZPC (prepared as described above) in GMDP/oil adjuvant administered subcutaneously. These animals achieved self-titers (against heat solubilized dog zona pellucida) of 1:4000–1:8000. Nearly seven months after immunization, two of the four dogs experienced estrus and remain infertile. The remaining two dogs have yet to experience estrus.

Another set of dogs was immunized 3 times at one-month intervals, using subcutaneous injections of 1 mg of recombinant canine ZPC produced using pZ166, (a plasmid similar to pZ169 but containing a DNA sequence encoding amino acids 23–379 of the canine ZPC protein) in GMDP/ oil adjuvant. These animals failed to develop self-titers and became pregnant after breeding. Similarly, dogs immunized with canine ZPC fragments produced using the baculovirus system failed to induce infertility.

EXAMPLE 19

Vaccination of Cows and Cats with

Recombinant Zona Pellucida Proteins Preliminary studies were undertaken to assess the ability of recombinant zona pellucida proteins to induce infertility in cows and cats.

Cows were injected with 3 or more doses (in GMDP (250 µg) oil adjuvant) of 1 mg of a variety of recombinantly derived ZPC proteins from canine and porcine sources including canine ZPC produced using the plasmid pZ169 as shown in FIG. 5. Recombinant proteins were administered in an unmodified form and in palmitylated and chitosan modified forms. None of the ZP protein preparations induced self-titers or infertility in the vaccinated cows.

Further studies are underway using different recombinant preparations of zona pellucida proteins and differing dosage regimens in attempts to induce self-titers and infertility in cows.

Similarly, cats were vaccinated with the following recombinant zona pellucida proteins: a mixture of recombinant feline ZPA, ZPB, and ZPC; porcine ZPC produced using pZ156 as described above and shown in FIG. 3; and canine ZPC produced using the plasmid pZ169 described above and shown in FIG. 5. Cats vaccinated using these ZP protein preparations produced antibody to the vaccine proteins, but produced no self-titers and were consequently fertile. Studies are ongoing to determine the effects of modifying the recombinant zona pellucida proteins in attempts to stimulate the production of self-titers and to induce infertility.

Studies are also ongoing to select other recombinantly derived zona pellucida protein fragments for testing as possible immunocontraceptives.

Numerous modifications in variations in the practice of the invention as illustrated in the above examples are expected to occur to those of ordinary skill in the art. Consequently, the illustrative examples are not intended to limit the scope of the invention as set out in the appended claims.

We claim:

1. A recombinant ZPC polypeptide selected from the group consisting of porcine ZPC as set out in SEQ ID NO. 6; rabbit ZPC as set out in SEQ ID NO. 8; canine ZPC as set out in SEQ ID NO. 12; feline ZPC as set out in SEQ ID NO. 18; and bovine ZPC as set out in SEQ ID NO. 24 or immunologically active fragments thereof.

2. A fusion protein comprising a ZPC polypeptide of claim 1, wherein said ZPC polypeptide is conjugated with a compound selected from the group consisting of keyhole limpet hemocyanin, muramyl dipeptide, histidine-tag, β-gal, and palmitic acid, and wherein said fusion protein remains effective to stimulate production of antibodies in a mammal that recognize a ZPA polypeptide of said mammal.

3. The ZPC polypeptide of claim 1 wherein said ZPC is feline ZPC and wherein said fragment is selected from the group consisting of fragments corresponding to amino acid numbers 36–50, 46–60, 56–70, 76–90, 96–110, 106–120, 116–130, 126–140, 136–150, 146–160, 156–170, 186–200, 196–210, 246–260, 266–280, 276–290, 286–300, 296–310, 316–330, 326–340, 336–350, 346–360, 376–390, 396–410, and 406–420 according to SEQ ID NO. 18.

4. The ZPC polypeptide of claim 1 wherein said ZPC is canine ZPC and wherein said fragment is selected from the group consisting of fragments corresponding to amino acid numbers 51–65, 61–75, 81–95, 131–145, 181–195, and 301–315 according to SEQ ID NO. 12.

5. The ZPC polypeptide of claim 1 wherein said ZPC is bovine ZPC and wherein said fragment is selected from the group consisting of fragments corresponding to amino acid numbers 1–15, 31–45, 51–65, 56–70, 61–75, 76–90, 106–120, 111–125, 116–130, 121–135, 131–145, 136–150, 141–155, 146–160, 151–165, 161–175, 181–195, 186–200, 191–205, 196–210, 201–215, 206–220, 216–230, 226–240, 241–255, 246–260, 261–275, 266–280, 271–285, 276–290, 291–305, 296–310, 301–315, 316–330, 321–335, 326–340, 331–345, 336–350, 341–355, 356–370, 361–375, 376–390, 381–395, 386–400, 396–410, 401–415, and 406–420 according to SEQ ID NO. 24.

6. A recombinant ZPC polypeptide comprising cynomolgus monkey ZPC as set out in SEQ ID. 49.

7. A fusion protein comprising a ZPC polypeptide of claim 6, wherein said ZPC polypeptide is conjugated with a compound selected from the group consisting of keyhole limpet hemocyanin, muramyl dipeptide, histidine-tag, β-gal, and palmitic acid, and wherein said fusion protein remains effective to stimulate production of antibodies in a mammal that recognize a ZPA polypeptide of said mammal.

8. A composition comprising, a recombinant ZPC polypeptide selected from the group consisting of porcine ZPC as set out in SEQ ID NO. 6; rabbit ZPC as set out in SEQ ID NO. 8; canine ZPC as set out in SEQ ID NO. 12; feline ZPC as set out in SEQ ID NO. 18; and bovine ZPC as set out in SEQ ID NO. 24 or immunologically active fragments thereof and a carrier, diluent and/or adjuvant.

9. The composition of claim 8 wherein said ZPC polypeptide comprises a fusion protein, wherein said ZPC polypeptide is conjugated with a compound selected from the group consisting of keyhole limpet hemocyanin, muramyl dipeptide, histidine-tag, β-gal, and palmitic acid, and wherein said fusion protein remains effective to stimulate production of antibodies in a mammal that recognize a ZPA polypeptide of said mammal.

10. The composition of claim 8 wherein said ZPC polypeptide is associated with chitosan, and wherein the modified ZPC polypeptide remains effective to stimulate production in a mammal of antibodies that recognize a ZPC polypeptide of said mammal.

11. The composition of claim 8 wherein said ZPC is feline ZPC and wherein said fragment is selected from the group consisting of fragments corresponding to amino acid numbers 36–50, 46–60, 56–70, 76–90, 96–110, 106–120, 116–130, 126–140, 136–150, 146–160, 156–170, 186–200, 196–210, 246–260, 266–280, 276–290, 286–300, 296–310, 316–330, 326–340, 336–350, 346–360, 376–390, 396–410, and 406–420 according to SEQ ID NO. 18.

12. The composition of claim 8 wherein said ZPC is canine ZPC and wherein said fragment is selected from the group consisting of fragments corresponding to amino acid numbers 51–65, 61–75, 81–95, 131–145, 181–195, and 301–315 according to SEQ ID NO. 12.

13. The composition of claim 8 wherein said ZPC is bovine ZPC and wherein said fragment is selected from the group consisting of fragments corresponding to amino acid numbers 1–15, 31–45, 51–65, 56–70, 61–75, 76–90, 106–120, 111–125, 116–130, 121–135, 131–145, 136–150, 141–155, 146–160, 151–165, 161–175, 181–195, 186–200, 191–205, 196–210, 201–215, 206–220, 216–230, 226–240, 241–255, 246–260, 261–275, 266–280, 271–285, 276–290, 291–305, 296–310, 301–315, 316–330, 321–335, 326–340, 331–345, 336–350, 341–355, 356–370, 361–375, 376–390, 381–395, 386–400, 396–410, 401–415, and 406–420 according to SEQ ID NO. 24.

14. A composition comprising, a recombinant cynomolgus monkey ZPC polypeptide as set out in SEQ ID. 49 and a carrier, diluent and/or adjuvant.

15. The composition of claim 14 wherein said ZPC polypeptide comprises a fusion protein, wherein said ZPC polypeptide is conjugated with a compound selected from the group consisting of keyhole limpet hemocyanin, muramyl dipeptide, histidine-tag, β-gal, and palmitic acid, and wherein said fusion protein remains effective to stimulate production of antibodies in a mammal that recognize a ZPA polypeptide of said mammal.

16. The composition of claim 14 wherein said ZPC polypeptide is associated with chitosan, and wherein the modified ZPC polypeptide remains effective to stimulate production in a mammal of antibodies that recognize a ZPC polypeptide of said mammal.

\* \* \* \* \*

SEQUENCE LISTING (1) GENERAL INFORMATION:

(iii) NUMBER OF SEQUENCES: 61

(2) INFORMATION FOR SEQ ID NO:1:

(i) SEQUENCE CHARACTERISTICS:
      (A) LENGTH: 2214 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Sus scrofa
      (D) DEVELOPMENTAL STAGE: Juvenile
      (E) HAPLOTYPE: Diploidy
      (F) TISSUE TYPE: Ovary
      (G) CELL TYPE: Oocyte (ix) FEATURE:
      (A) NAME/KEY: sig_peptide
      (B) LOCATION: 12..119

(ix) FEATURE:
      (A) NAME/KEY: mat_peptide
      (B) LOCATION: 120..2153

(ix) FEATURE:
      (A) NAME/KEY: CDS
      (B) LOCATION: 12..2153

(xi) SEQUENCE DESCRIPTION: SEQ ID NO:1:

```
GAATTCCGGG C AGG CAC AGA GGA GAC AGT GGG AGA CCC TTA AGC TGG CTC      50
             Arg His Arg Gly Asp Ser Gly Arg Pro Leu Ser Trp Leu
             -36 -35                -30                -25

AGT GCA AGC TGG AGG TCA CTT CTT CTA TTT TTC CCC CTT GTG ACT TCA       98
```

-continued

```
          Ser Ala Ser Trp Arg Ser Leu Leu Phe Phe Pro Leu Val Thr Ser
                  -20              -15                  -10

GTG AAC TCC ATA GGT GTC AAT CAG TTG GTG AAT ACT GCC TTC CCA GGT      146
Val Asn Ser Ile Gly Val Asn Gln Leu Val Asn Thr Ala Phe Pro Gly
        -5                   1                   5

ATT GTC ACT TGC CAT GAA AAT AGA ATG GTA GTG GAA TTT CCA AGA ATT      194
Ile Val Thr Cys His Glu Asn Arg Met Val Val Glu Phe Pro Arg Ile
 10              15                  20                  25

CTT GGC ACT AAG ATA CAG TAC ACC TCT GTG GTG GAC CCT CTT GGT CTT      242
Leu Gly Thr Lys Ile Gln Tyr Thr Ser Val Val Asp Pro Leu Gly Leu
             30                  35                  40

GAA ATG ATG AAC TGT ACT TAT GTT CTG GAC CCA GAA AAC CTC ACC CTG      290
Glu Met Met Asn Cys Thr Tyr Val Leu Asp Pro Glu Asn Leu Thr Leu
                 45                  50                  55

AAG GCC CCA TAT GAA GCC TGT ACC AAA AGA GTG CGT GGC CAT CAC CAA      338
Lys Ala Pro Tyr Glu Ala Cys Thr Lys Arg Val Arg Gly His His Gln
             60                  65                  70

ATG ACC ATC AGA CTC ATA GAT GAC AAT GCT GCT TTA AGA CAA GAG GCT      386
Met Thr Ile Arg Leu Ile Asp Asp Asn Ala Ala Leu Arg Gln Glu Ala
 75                  80                  85

CTC ATG TAT CAC ATC AGC TGT CCT GTT ATG GGA GCA GAA GGC CCT GAT      434
Leu Met Tyr His Ile Ser Cys Pro Val Met Gly Ala Glu Gly Pro Asp
 90                  95                 100                 105

CAG CAT TCG GGA TCC ACA ATC TGC ATG AAA GAT TTC ATG TCT TTT ACC      482
Gln His Ser Gly Ser Thr Ile Cys Met Lys Asp Phe Met Ser Phe Thr
             110                 115                 120

TTT AAC TTT TTT CCC GGG ATG GCT GAC GAA AAT GTG AAA CGT GAG GAT      530
Phe Asn Phe Phe Pro Gly Met Ala Asp Glu Asn Val Lys Arg Glu Asp
             125                 130                 135

TCG AAG CAG CGC ATG GGA TGG AGC CTT GTA GTT GGT GAC GGT GAA AGA      578
Ser Lys Gln Arg Met Gly Trp Ser Leu Val Val Gly Asp Gly Glu Arg
             140                 145                 150

GCC CGA ACT CTG ACC TTT CAG GAG GCC ATG ACC CAA GGA TAT AAT TTC      626
Ala Arg Thr Leu Thr Phe Gln Glu Ala Met Thr Gln Gly Tyr Asn Phe
 155                 160                 165

CTG ATA GAG AAC CAG AAG ATG AAC ATC CAA GTG TCA TTC CAT GCC ACT      674
Leu Ile Glu Asn Gln Lys Met Asn Ile Gln Val Ser Phe His Ala Thr
 170                 175                 180                 185

GGA GTG ACT CGC TAC TCG CAA GGT AAC AGT CAT CTC TAC ATG GTA CCT      722
Gly Val Thr Arg Tyr Ser Gln Gly Asn Ser His Leu Tyr Met Val Pro
             190                 195                 200

CTG AAG CTT AAA CAT GTA TCT CAT GGG CAG TCT CTC ATC TTA GCA TCA      770
Leu Lys Leu Lys His Val Ser His Gly Gln Ser Leu Ile Leu Ala Ser
             205                 210                 215

CAA CTC ATC TGT GTG GCA GAT CCT GTG ACC TGT AAT GCC ACA CAC GTG      818
Gln Leu Ile Cys Val Ala Asp Pro Val Thr Cys Asn Ala Thr His Val
             220                 225                 230

ACT CTT GCC ATA CCA GAG TTT CCT GGG AAG CTA AAA TCC GTG AAC TTG      866
Thr Leu Ala Ile Pro Glu Phe Pro Gly Lys Leu Lys Ser Val Asn Leu
 235                 240                 245

GGA AGT GGG AAT ATT GCT GTG AGC CAG CTG CAC AAA CAC GGG ATT GAA      914
Gly Ser Gly Asn Ile Ala Val Ser Gln Leu His Lys His Gly Ile Glu
 250                 255                 260                 265

ATG GAA ACA ACA AAC GGC CTG AGG TTG CAT TTC AAC CAA ACT CTT CTC      962
Met Glu Thr Thr Asn Gly Leu Arg Leu His Phe Asn Gln Thr Leu Leu
             270                 275                 280

AAA ACA AAT GTC TCT GAA AAA TGC CTA CCA CAT CAG TTG TAC TTA TCT     1010
Lys Thr Asn Val Ser Glu Lys Cys Leu Pro His Gln Leu Tyr Leu Ser
             285                 290                 295

TCA CTC AAG CTG ACT TTT CAC AGT CAA CTA GAG GCA GTA TCC ATG GTG     1058
```

```
Ser Leu Lys Leu Thr Phe His Ser Gln Leu Glu Ala Val Ser Met Val
        300                 305                 310

ATT TAT CCT GAG TGT CTC TGT GAG TCA ACA GTC TCT TTA GTT TCA GAG      1106
Ile Tyr Pro Glu Cys Leu Cys Glu Ser Thr Val Ser Leu Val Ser Glu
        315                 320                 325

GAG CTA TGC ACT CAG GAT GGG TTT ATG GAC GTC AAG GTC CAC AGC CAC      1154
Glu Leu Cys Thr Gln Asp Gly Phe Met Asp Val Lys Val His Ser His
330                 335                 340                 345

CAA ACA AAA CCA GCT CTC AAC TTG GAT ACC CTC AGG GTG GGA GAC TCA      1202
Gln Thr Lys Pro Ala Leu Asn Leu Asp Thr Leu Arg Val Gly Asp Ser
                350                 355                 360

TCC TGC CAG CCA ACC TTT AAA GCT CCA GCT CAG GGG CTG GTA CAG TTT      1250
Ser Cys Gln Pro Thr Phe Lys Ala Pro Ala Gln Gly Leu Val Gln Phe
            365                 370                 375

CGC ATA CCC CTG AAT GGA TGT GGA ACA AGA CAT AAG TTC AAG AAT GAC      1298
Arg Ile Pro Leu Asn Gly Cys Gly Thr Arg His Lys Phe Lys Asn Asp
        380                 385                 390

AAA GTC ATC TAT GAA AAT GAA ATA CAT GCT CTC TGG GCA GAT CCT CCA      1346
Lys Val Ile Tyr Glu Asn Glu Ile His Ala Leu Trp Ala Asp Pro Pro
395                 400                 405

AGC GCC GTT TCC AGA GAT AGT GAG TTC AGA ATG ACA GTG AGG TGC TCT      1394
Ser Ala Val Ser Arg Asp Ser Glu Phe Arg Met Thr Val Arg Cys Ser
410                 415                 420                 425

TAC AGC AGC AGC AAC ATG CTA ATA AAT ACC AAT GTT GAA AGT CTT CCT      1442
Tyr Ser Ser Ser Asn Met Leu Ile Asn Thr Asn Val Glu Ser Leu Pro
                430                 435                 440

TCT CCA GAG GCC TCA GTG AAG CCA GGT CCA CTT ACC CTG ACT CTG CAA      1490
Ser Pro Glu Ala Ser Val Lys Pro Gly Pro Leu Thr Leu Thr Leu Gln
            445                 450                 455

ACC TAC CCA GAT AAC GCC TAC CTG CAG CCT TAT GGG GAC AAG GAG TAC      1538
Thr Tyr Pro Asp Asn Ala Tyr Leu Gln Pro Tyr Gly Asp Lys Glu Tyr
        460                 465                 470

CCT GTG GTG AAA TAT CTC CGC CAA CCA ATT TAC CTA GAA GTG AGA ATC      1586
Pro Val Val Lys Tyr Leu Arg Gln Pro Ile Tyr Leu Glu Val Arg Ile
475                 480                 485

CTC AAC AGG ACT GAC CCC AAC ATC AAG CTG GTC TTG GAT GAC TGC TGG      1634
Leu Asn Arg Thr Asp Pro Asn Ile Lys Leu Val Leu Asp Asp Cys Trp
490                 495                 500                 505

GCA ACA TCC ACA GAG GAC CCA GCC TCT CTC CCC CAG TGG AAT GTT GTC      1682
Ala Thr Ser Thr Glu Asp Pro Ala Ser Leu Pro Gln Trp Asn Val Val
                510                 515                 520

ATG GAT GGC TGT GAA TAC AAC CTG GAC AAC CAC AGA ACC ACC TTC CAT      1730
Met Asp Gly Cys Glu Tyr Asn Leu Asp Asn His Arg Thr Thr Phe His
            525                 530                 535

CCG GTG GGC TCC TCC GTG ACC TAT CCT AAC CAC CAT CAG AGG TTT GAT      1778
Pro Val Gly Ser Ser Val Thr Tyr Pro Asn His His Gln Arg Phe Asp
        540                 545                 550

GTG AAG ACC TTT GCC TTT GTG TCA GGG GCC CAA GGG GTC TCT CAA CTG      1826
Val Lys Thr Phe Ala Phe Val Ser Gly Ala Gln Gly Val Ser Gln Leu
555                 560                 565

GTC TAC TTC CAC TGC AGT GTC TTC ATC TGC AAT CAA CTC TCT CCC ACC      1874
Val Tyr Phe His Cys Ser Val Phe Ile Cys Asn Gln Leu Ser Pro Thr
570                 575                 580                 585

TTC TCT CTG TGT TCT GTG ACT TGC CAT GGG CCA TCT AGG AGC CGG CGA      1922
Phe Ser Leu Cys Ser Val Thr Cys His Gly Pro Ser Arg Ser Arg Arg
                590                 595                 600

GCT ACA GGG ACC ACT GAG GAA GAG AAA ATG ATA GTG AGT CTC CCG GGC      1970
Ala Thr Gly Thr Thr Glu Glu Glu Lys Met Ile Val Ser Leu Pro Gly
            605                 610                 615

CCC ATC CTG CTG TTG TCA GAT GGC TCT TCA CTC AGA GAT GCT GTG AAC      2018
```

-continued

```
Pro Ile Leu Leu Leu Ser Asp Gly Ser Ser Leu Arg Asp Ala Val Asn
         620                 625                 630

TCT AAA GGA TCC AGA ACC AAC GGA TAT GTT GCT TTT AAA ACT ATG GTT    2066
Ser Lys Gly Ser Arg Thr Asn Gly Tyr Val Ala Phe Lys Thr Met Val
         635                 640                 645

GCT ATG GTT GCT TCA GCA GGC ATC GTG GCA ACT CTA GGC CTC ATC AGC    2114
Ala Met Val Ala Ser Ala Gly Ile Val Ala Thr Leu Gly Leu Ile Ser
650                 655                 660                 665

TAC CTG CAC AAA AAA AGA ATC ATG ATG TTA AAT CAC TAATTTGGAT         2160
Tyr Leu His Lys Lys Arg Ile Met Met Leu Asn His
                 670                 675

TTTCAAATAA AAGTGGAAGT AAGCCTCTTC TAAAAAAAAA AAAAACCGGA ATTC        2214

(2) INFORMATION FOR SEQ ID NO:2:

(i) SEQUENCE CHARACTERISTICS:
        (A) LENGTH: 713 amino acids
        (B) TYPE: amino acid
        (D) TOPOLOGY: linear (ii) MOLECULE TYPE: protein (xi) SEQUENCE DESCRIPTION: SEQ ID NO:2:

Arg His Arg Gly Asp Ser Gly Arg Pro Leu Ser Trp Leu Ser Ala Ser
-36 -35              -30                 -25

Trp Arg Ser Leu Leu Leu Phe Phe Pro Leu Val Thr Ser Val Asn Ser
-20              -15                 -10                  -5

Ile Gly Val Asn Gln Leu Val Asn Thr Ala Phe Pro Gly Ile Val Thr
                  1                  5                 10

Cys His Glu Asn Arg Met Val Val Glu Phe Pro Arg Ile Leu Gly Thr
             15                 20                 25

Lys Ile Gln Tyr Thr Ser Val Val Asp Pro Leu Gly Leu Glu Met Met
         30                 35                 40

Asn Cys Thr Tyr Val Leu Asp Pro Glu Asn Leu Thr Leu Lys Ala Pro
45                 50                 55                 60

Tyr Glu Ala Cys Thr Lys Arg Val Arg Gly His His Gln Met Thr Ile
                 65                 70                 75

Arg Leu Ile Asp Asp Asn Ala Ala Leu Arg Gln Glu Ala Leu Met Tyr
             80                 85                 90

His Ile Ser Cys Pro Val Met Gly Ala Glu Gly Pro Asp Gln His Ser
         95                100                105

Gly Ser Thr Ile Cys Met Lys Asp Phe Met Ser Phe Thr Phe Asn Phe
110                115                120

Phe Pro Gly Met Ala Asp Glu Asn Val Lys Arg Glu Asp Ser Lys Gln
125                130                135                140

Arg Met Gly Trp Ser Leu Val Val Gly Asp Gly Glu Arg Ala Arg Thr
                145                150                155

Leu Thr Phe Gln Glu Ala Met Thr Gln Gly Tyr Asn Phe Leu Ile Glu
             160                165                170

Asn Gln Lys Met Asn Ile Gln Val Ser Phe His Ala Thr Gly Val Thr
         175                180                185

Arg Tyr Ser Gln Gly Asn Ser His Leu Tyr Met Val Pro Leu Lys Leu
     190                195                200

Lys His Val Ser His Gly Gln Ser Leu Ile Leu Ala Ser Gln Leu Ile
205                210                215                220

Cys Val Ala Asp Pro Val Thr Cys Asn Ala Thr His Val Thr Leu Ala
                225                230                235
```

-continued

```
Ile Pro Glu Phe Pro Gly Lys Leu Lys Ser Val Asn Leu Gly Ser Gly
            240                 245                 250

Asn Ile Ala Val Ser Gln Leu His Lys His Gly Ile Glu Met Glu Thr
        255                 260                 265

Thr Asn Gly Leu Arg Leu His Phe Asn Gln Thr Leu Leu Lys Thr Asn
    270                 275                 280

Val Ser Glu Lys Cys Leu Pro His Gln Leu Tyr Leu Ser Ser Leu Lys
285                 290                 295                 300

Leu Thr Phe His Ser Gln Leu Glu Ala Val Ser Met Val Ile Tyr Pro
                305                 310                 315

Glu Cys Leu Cys Glu Ser Thr Val Ser Leu Val Ser Glu Glu Leu Cys
            320                 325                 330

Thr Gln Asp Gly Phe Met Asp Val Lys Val His Ser His Gln Thr Lys
        335                 340                 345

Pro Ala Leu Asn Leu Asp Thr Leu Arg Val Gly Asp Ser Ser Cys Gln
350                 355                 360

Pro Thr Phe Lys Ala Pro Ala Gln Gly Leu Val Gln Phe Arg Ile Pro
365                 370                 375                 380

Leu Asn Gly Cys Gly Thr Arg His Lys Phe Lys Asn Asp Lys Val Ile
                385                 390                 395

Tyr Glu Asn Glu Ile His Ala Leu Trp Ala Asp Pro Ser Ala Val
            400                 405                 410

Ser Arg Asp Ser Glu Phe Arg Met Thr Val Arg Cys Ser Tyr Ser Ser
        415                 420                 425

Ser Asn Met Leu Ile Asn Thr Asn Val Glu Ser Leu Pro Ser Pro Glu
    430                 435                 440

Ala Ser Val Lys Pro Gly Pro Leu Thr Leu Thr Leu Gln Thr Tyr Pro
445                 450                 455                 460

Asp Asn Ala Tyr Leu Gln Pro Tyr Gly Asp Lys Glu Tyr Pro Val Val
                465                 470                 475

Lys Tyr Leu Arg Gln Pro Ile Tyr Leu Glu Val Arg Ile Leu Asn Arg
            480                 485                 490

Thr Asp Pro Asn Ile Lys Leu Val Leu Asp Asp Cys Trp Ala Thr Ser
        495                 500                 505

Thr Glu Asp Pro Ala Ser Leu Pro Gln Trp Asn Val Val Met Asp Gly
    510                 515                 520

Cys Glu Tyr Asn Leu Asp Asn His Arg Thr Thr Phe His Pro Val Gly
525                 530                 535                 540

Ser Ser Val Thr Tyr Pro Asn His His Gln Arg Phe Asp Val Lys Thr
                545                 550                 555

Phe Ala Phe Val Ser Gly Ala Gln Gly Val Ser Gln Leu Val Tyr Phe
            560                 565                 570

His Cys Ser Val Phe Ile Cys Asn Gln Leu Ser Pro Thr Phe Ser Leu
        575                 580                 585

Cys Ser Val Thr Cys His Gly Pro Ser Arg Ser Arg Arg Ala Thr Gly
    590                 595                 600

Thr Thr Glu Glu Glu Lys Met Ile Val Ser Leu Pro Gly Pro Ile Leu
605                 610                 615                 620

Leu Leu Ser Asp Gly Ser Ser Leu Arg Asp Ala Val Asn Ser Lys Gly
                625                 630                 635

Ser Arg Thr Asn Gly Tyr Val Ala Phe Lys Thr Met Val Ala Met Val
            640                 645                 650

Ala Ser Ala Gly Ile Val Ala Thr Leu Gly Leu Ile Ser Tyr Leu His
        655                 660                 665
```

```
Lys Lys Arg Ile Met Met Leu Asn His
    670             675
```

(2) INFORMATION FOR SEQ ID NO:3:

(i) SEQUENCE CHARACTERISTICS:
        (A) LENGTH: 1699 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Sus scrofa
        (D) DEVELOPMENTAL STAGE: Juvenile
        (E) HAPLOTYPE: Diploidy
        (F) TISSUE TYPE: Ovary
        (G) CELL TYPE: Oocyte (ix) FEATURE:
        (A) NAME/KEY: sig_peptide
        (B) LOCATION: 38..445

(ix) FEATURE:
        (A) NAME/KEY: mat_peptide
        (B) LOCATION: 446..1648

(ix) FEATURE:
        (A) NAME/KEY: CDS
        (B) LOCATION: 38..1648

(xi) SEQUENCE DESCRIPTION: SEQ ID NO:3:

```
GAATTCCGGG TGGAAGTACC TGTTCTCCGC AGGCGCT ATG TGG TTG CGG CCG TCC           55
                                        Met Trp Leu Arg Pro Ser
                                        -136-135

ATC TGG CTC TGC TTT CCG CTG TGT CTT GCT CTG CCA GGC CAG TCT CAG          103
Ile Trp Leu Cys Phe Pro Leu Cys Leu Ala Leu Pro Gly Gln Ser Gln
-130            -125            -120            -115

CCC AAA GCA GCA GAT GAC CTT GGT GGC CTC TAC TGT GGG CCA AGC AGC          151
Pro Lys Ala Ala Asp Asp Leu Gly Gly Leu Tyr Cys Gly Pro Ser Ser
            -110            -105            -100

TTT CAT TTC TCC ATA AAT CTT CTC AGC CAG GAC ACA GCA ACT CCT CCT          199
Phe His Phe Ser Ile Asn Leu Leu Ser Gln Asp Thr Ala Thr Pro Pro
        -95             -90             -85

GCA CTG GTG GTT TGG GAC AGG CGC GGG CGG CTG CAC AAG CTG CAG AAT          247
Ala Leu Val Val Trp Asp Arg Arg Gly Arg Leu His Lys Leu Gln Asn
    -80             -75             -70

GAC TCT GGC TGT GGC ACG TGG GTC CAC AAG GGC CCA GGC AGC TCC ATG          295
Asp Ser Gly Cys Gly Thr Trp Val His Lys Gly Pro Gly Ser Ser Met
-65             -60             -55

GGA GTG GAA GCA TCC TAC AGA GGC TGC TAT GTG ACT GAG TGG GAC TCT          343
Gly Val Glu Ala Ser Tyr Arg Gly Cys Tyr Val Thr Glu Trp Asp Ser
-50             -45             -40             -35

CAC TAC CTC ATG CCC ATT GGA CTT GAA GAA GCA GAT GCA GGT GGA CAC          391
His Tyr Leu Met Pro Ile Gly Leu Glu Glu Ala Asp Ala Gly Gly His
            -30             -25             -20

AGA ACA GTC ACA GAG ACG AAA CTG TTT AAG TGC CCT GTG GAT TTC CTA          439
Arg Thr Val Thr Glu Thr Lys Leu Phe Lys Cys Pro Val Asp Phe Leu
        -15             -10             -5

GCT CTT GAT GTT CCA ACC ATT GGC CTT TGT GAT GCT GTC CCA GTG TGG          487
Ala Leu Asp Val Pro Thr Ile Gly Leu Cys Asp Ala Val Pro Val Trp
        1               5               10
```

-continued

| | | | | | | | | | | | | | | | | |
|---|---|---|---|---|---|---|---|---|---|---|---|---|---|---|---|---|
| GAC | CGA | TTG | CCA | TGT | GCT | CCT | CCA | CCC | ATC | ACT | CAA | GGA | GAA | TGC | AAG | 535 |
| Asp | Arg | Leu | Pro | Cys | Ala | Pro | Pro | Pro | Ile | Thr | Gln | Gly | Glu | Cys | Lys | |
| 15 | | | | 20 | | | | | 25 | | | | | 30 | | |

| | | | | | | | | | | | | | | | | |
|---|---|---|---|---|---|---|---|---|---|---|---|---|---|---|---|---|
| CAG | CTT | GGC | TGC | TGC | TAC | AAC | TCG | GAA | GAG | GTC | CCT | TCT | TGT | TAC | TAT | 583 |
| Gln | Leu | Gly | Cys | Cys | Tyr | Asn | Ser | Glu | Glu | Val | Pro | Ser | Cys | Tyr | Tyr | |
| | | | 35 | | | | | 40 | | | | | 45 | | | |

| | | | | | | | | | | | | | | | | |
|---|---|---|---|---|---|---|---|---|---|---|---|---|---|---|---|---|
| GGA | AAC | ACA | GTG | ACC | TCA | CGC | TGT | ACC | CAA | GAT | GGC | CAC | TTC | TCC | ATC | 631 |
| Gly | Asn | Thr | Val | Thr | Ser | Arg | Cys | Thr | Gln | Asp | Gly | His | Phe | Ser | Ile | |
| | | | 50 | | | | | 55 | | | | | 60 | | | |

| | | | | | | | | | | | | | | | | |
|---|---|---|---|---|---|---|---|---|---|---|---|---|---|---|---|---|
| GCT | GTG | TCT | CGC | AAT | GTG | ACC | TCA | CCT | CCA | CTG | CTC | TGG | GAT | TCT | GTG | 679 |
| Ala | Val | Ser | Arg | Asn | Val | Thr | Ser | Pro | Pro | Leu | Leu | Trp | Asp | Ser | Val | |
| | | 65 | | | | | 70 | | | | | 75 | | | | |

| | | | | | | | | | | | | | | | | |
|---|---|---|---|---|---|---|---|---|---|---|---|---|---|---|---|---|
| CAC | CTG | GCC | TTC | AGA | AAT | GAC | AGT | GAA | TGT | AAA | CCT | GTG | ATG | GAA | ACA | 727 |
| His | Leu | Ala | Phe | Arg | Asn | Asp | Ser | Glu | Cys | Lys | Pro | Val | Met | Glu | Thr | |
| | | 80 | | | | | 85 | | | | | 90 | | | | |

| | | | | | | | | | | | | | | | | |
|---|---|---|---|---|---|---|---|---|---|---|---|---|---|---|---|---|
| CAC | ACT | TTT | GTC | CTC | TTC | CGG | TTT | CCA | TTT | AGT | TCC | TGT | GGG | ACT | GCA | 775 |
| His | Thr | Phe | Val | Leu | Phe | Arg | Phe | Pro | Phe | Ser | Ser | Cys | Gly | Thr | Ala | |
| 95 | | | | | 100 | | | | | 105 | | | | | 110 | |

| | | | | | | | | | | | | | | | | |
|---|---|---|---|---|---|---|---|---|---|---|---|---|---|---|---|---|
| AAA | CGG | GTA | ACT | GGG | AAC | CAG | GCG | GTA | TAT | GAA | AAT | GAG | CTG | GTA | GCA | 823 |
| Lys | Arg | Val | Thr | Gly | Asn | Gln | Ala | Val | Tyr | Glu | Asn | Glu | Leu | Val | Ala | |
| | | | | 115 | | | | | 120 | | | | | 125 | | |

| | | | | | | | | | | | | | | | | |
|---|---|---|---|---|---|---|---|---|---|---|---|---|---|---|---|---|
| GCT | CGG | GAT | GTG | AGG | ACT | TGG | AGC | CAT | GGT | TCT | ATT | ACC | CGA | GAC | AGC | 871 |
| Ala | Arg | Asp | Val | Arg | Thr | Trp | Ser | His | Gly | Ser | Ile | Thr | Arg | Asp | Ser | |
| | | | 130 | | | | | 135 | | | | | 140 | | | |

| | | | | | | | | | | | | | | | | |
|---|---|---|---|---|---|---|---|---|---|---|---|---|---|---|---|---|
| ATC | TTC | AGG | CTT | CGA | GTC | AGT | TGT | ATC | TAC | TCT | GTA | AGT | AGC | AGT | GCT | 919 |
| Ile | Phe | Arg | Leu | Arg | Val | Ser | Cys | Ile | Tyr | Ser | Val | Ser | Ser | Ser | Ala | |
| | | | | 145 | | | | | 150 | | | | | 155 | | |

| | | | | | | | | | | | | | | | | |
|---|---|---|---|---|---|---|---|---|---|---|---|---|---|---|---|---|
| CTC | CCA | GTT | AAC | ATC | CAG | GTT | TTC | ACT | CTC | CCA | CCA | CCG | CTT | CCG | GAG | 967 |
| Leu | Pro | Val | Asn | Ile | Gln | Val | Phe | Thr | Leu | Pro | Pro | Pro | Leu | Pro | Glu | |
| | 160 | | | | | 165 | | | | | 170 | | | | | |

| | | | | | | | | | | | | | | | | |
|---|---|---|---|---|---|---|---|---|---|---|---|---|---|---|---|---|
| ACC | CAC | CCT | GGA | CCT | CTT | ACT | CTG | GAG | CTT | CAG | ATT | GCC | AAA | GAT | GAA | 1015 |
| Thr | His | Pro | Gly | Pro | Leu | Thr | Leu | Glu | Leu | Gln | Ile | Ala | Lys | Asp | Glu | |
| 175 | | | | | 180 | | | | | 185 | | | | | 190 | |

| | | | | | | | | | | | | | | | | |
|---|---|---|---|---|---|---|---|---|---|---|---|---|---|---|---|---|
| CGC | TAT | GGC | TCC | TAC | TAC | AAT | GCT | AGT | GAC | TAC | CCG | GTG | GTG | AAA | TTG | 1063 |
| Arg | Tyr | Gly | Ser | Tyr | Tyr | Asn | Ala | Ser | Asp | Tyr | Pro | Val | Val | Lys | Leu | |
| | | | | 195 | | | | | 200 | | | | | 205 | | |

| | | | | | | | | | | | | | | | | |
|---|---|---|---|---|---|---|---|---|---|---|---|---|---|---|---|---|
| CTT | CGG | GAG | CCC | ATC | TAT | GTG | GAG | GTC | TCT | ATC | CGT | CAC | CGA | ACA | GAC | 1111 |
| Leu | Arg | Glu | Pro | Ile | Tyr | Val | Glu | Val | Ser | Ile | Arg | His | Arg | Thr | Asp | |
| | | | | 210 | | | | | 215 | | | | | 220 | | |

| | | | | | | | | | | | | | | | | |
|---|---|---|---|---|---|---|---|---|---|---|---|---|---|---|---|---|
| CCC | AGT | CTC | GGG | CTG | CAC | CTG | CAC | CAG | TGC | TGG | GCC | ACA | CCC | GGC | ATG | 1159 |
| Pro | Ser | Leu | Gly | Leu | His | Leu | His | Gln | Cys | Trp | Ala | Thr | Pro | Gly | Met | |
| | | 225 | | | | | 230 | | | | | 235 | | | | |

| | | | | | | | | | | | | | | | | |
|---|---|---|---|---|---|---|---|---|---|---|---|---|---|---|---|---|
| AGC | CCC | CTG | CTC | CAG | CCA | CAG | TGG | CCC | ATG | CTA | GTC | AAT | GGA | TGC | CCC | 1207 |
| Ser | Pro | Leu | Leu | Gln | Pro | Gln | Trp | Pro | Met | Leu | Val | Asn | Gly | Cys | Pro | |
| | | 240 | | | | | 245 | | | | | 250 | | | | |

| | | | | | | | | | | | | | | | | |
|---|---|---|---|---|---|---|---|---|---|---|---|---|---|---|---|---|
| TAC | ACT | GGA | GAC | AAC | TAC | CAG | ACC | AAA | CTG | ATC | CCT | GTC | CAG | AAA | GCC | 1255 |
| Tyr | Thr | Gly | Asp | Asn | Tyr | Gln | Thr | Lys | Leu | Ile | Pro | Val | Gln | Lys | Ala | |
| 255 | | | | | 260 | | | | | 265 | | | | | 270 | |

| | | | | | | | | | | | | | | | | |
|---|---|---|---|---|---|---|---|---|---|---|---|---|---|---|---|---|
| TCA | AAC | CTG | CTA | TTT | CCT | TCT | CAC | TAC | CAG | CGT | TTC | AGT | GTT | TCC | ACC | 1303 |
| Ser | Asn | Leu | Leu | Phe | Pro | Ser | His | Tyr | Gln | Arg | Phe | Ser | Val | Ser | Thr | |
| | | | | 275 | | | | | 280 | | | | | 285 | | |

| | | | | | | | | | | | | | | | | |
|---|---|---|---|---|---|---|---|---|---|---|---|---|---|---|---|---|
| TTC | AGT | TTT | GTG | GAC | TCT | GTG | GCA | AAG | CAG | GCA | CTC | AAG | GGA | CCG | GTG | 1351 |
| Phe | Ser | Phe | Val | Asp | Ser | Val | Ala | Lys | Gln | Ala | Leu | Lys | Gly | Pro | Val | |
| | | | 290 | | | | | 295 | | | | | 300 | | | |

| | | | | | | | | | | | | | | | | |
|---|---|---|---|---|---|---|---|---|---|---|---|---|---|---|---|---|
| TAT | CTG | CAT | TGT | ACT | GCA | TCG | GTC | TGC | AAG | CCT | GCA | GGG | GCA | CCG | ATC | 1399 |
| Tyr | Leu | His | Cys | Thr | Ala | Ser | Val | Cys | Lys | Pro | Ala | Gly | Ala | Pro | Ile | |
| | | | 305 | | | | | 310 | | | | | 315 | | | |

| | | | | | | | | | | | | | | | | |
|---|---|---|---|---|---|---|---|---|---|---|---|---|---|---|---|---|
| TGT | GTG | ACA | ACC | TGT | CCT | GCT | GCC | AGA | CGA | AGA | AGA | AGT | TCT | GAC | ATC | 1447 |
| Cys | Val | Thr | Thr | Cys | Pro | Ala | Ala | Arg | Arg | Arg | Arg | Ser | Ser | Asp | Ile | |
| | | 320 | | | | | 325 | | | | | 330 | | | | |

```
CAT TTT CAG AAT GGC ACT GCT AGC ATT TCT AGC AAG GGT CCC ATG ATT        1495
His Phe Gln Asn Gly Thr Ala Ser Ile Ser Ser Lys Gly Pro Met Ile
335                 340                 345                 350

CTA CTC CAA GCC ACT CGG GAC TCT TCA GAA AGG CTC CAT AAA TAC TCA        1543
Leu Leu Gln Ala Thr Arg Asp Ser Ser Glu Arg Leu His Lys Tyr Ser
                355                 360                 365

AGG CCT CCT GTA GAC TCC CAT GCT CTG TGG GTG GCT GGC CTC TTG GGA        1591
Arg Pro Pro Val Asp Ser His Ala Leu Trp Val Ala Gly Leu Leu Gly
            370                 375                 380

AGC TTA ATT ATT GGA GCC TTG TTA GTG TCC TAC CTG GTC TTC AGG AAA        1639
Ser Leu Ile Ile Gly Ala Leu Leu Val Ser Tyr Leu Val Phe Arg Lys
        385                 390                 395

TGG AGA TGAGTTACTC AGACCAAATG TGTCAATAAA ACCAATAAAA CAAAACCGGA         1695
Trp Arg
    400

ATTC                                                                   1699
```

(2) INFORMATION FOR SEQ ID NO:4:

(i) SEQUENCE CHARACTERISTICS:
        (A) LENGTH: 536 amino acids
        (B) TYPE: amino acid
        (D) TOPOLOGY: linear (ii) MOLECULE TYPE: protein (xi) SEQUENCE DESCRIPTION: SEQ ID NO:4:

```
Met Trp Leu Arg Pro Ser Ile Trp Leu Cys Phe Pro Leu Cys Leu Ala
-136 -135           -130                -125

Leu Pro Gly Gln Ser Gln Pro Lys Ala Ala Asp Asp Leu Gly Gly Leu
-120            -115                -110                -105

Tyr Cys Gly Pro Ser Ser Phe His Phe Ser Ile Asn Leu Leu Ser Gln
                -100                -95                 -90

Asp Thr Ala Thr Pro Pro Ala Leu Val Val Trp Asp Arg Arg Gly Arg
            -85                 -80                 -75

Leu His Lys Leu Gln Asn Asp Ser Gly Cys Gly Thr Trp Val His Lys
        -70                 -65                 -60

Gly Pro Gly Ser Ser Met Gly Val Glu Ala Ser Tyr Arg Gly Cys Tyr
    -55                 -50                 -45

Val Thr Glu Trp Asp Ser His Tyr Leu Met Pro Ile Gly Leu Glu Glu
-40                 -35                 -30                 -25

Ala Asp Ala Gly Gly His Arg Thr Val Thr Glu Thr Lys Leu Phe Lys
                -20                 -15                 -10

Cys Pro Val Asp Phe Leu Ala Leu Asp Val Pro Thr Ile Gly Leu Cys
                -5                  1                   5

Asp Ala Val Pro Val Trp Asp Arg Leu Pro Cys Ala Pro Pro Ile
        10                  15                  20

Thr Gln Gly Glu Cys Lys Gln Leu Gly Cys Cys Tyr Asn Ser Glu Glu
25                  30                  35                  40

Val Pro Ser Cys Tyr Tyr Gly Asn Thr Val Thr Ser Arg Cys Thr Gln
                45                  50                  55

Asp Gly His Phe Ser Ile Ala Val Ser Arg Asn Val Thr Ser Pro Pro
            60                  65                  70

Leu Leu Trp Asp Ser Val His Leu Ala Phe Arg Asn Asp Ser Glu Cys
        75                  80                  85

Lys Pro Val Met Glu Thr His Thr Phe Val Leu Phe Arg Phe Pro Phe
    90                  95                  100

Ser Ser Cys Gly Thr Ala Lys Arg Val Thr Gly Asn Gln Ala Val Tyr
```

```
                   105                 110                 115                 120
Glu Asn Glu Leu Val Ala Ala Arg Asp Val Arg Thr Trp Ser His Gly
                    125                 130                 135

Ser Ile Thr Arg Asp Ser Ile Phe Arg Leu Arg Val Ser Cys Ile Tyr
            140                 145                 150

Ser Val Ser Ser Ala Leu Pro Val Asn Ile Gln Val Phe Thr Leu
        155                 160                 165

Pro Pro Leu Pro Glu Thr His Pro Gly Pro Leu Thr Leu Glu Leu
170                 175                 180

Gln Ile Ala Lys Asp Glu Arg Tyr Gly Ser Tyr Asn Ala Ser Asp
185                 190                 195                 200

Tyr Pro Val Val Lys Leu Leu Arg Glu Pro Ile Tyr Val Glu Val Ser
                205                 210                 215

Ile Arg His Arg Thr Asp Pro Ser Leu Gly Leu His Leu His Gln Cys
                220                 225                 230

Trp Ala Thr Pro Gly Met Ser Pro Leu Leu Gln Pro Gln Trp Pro Met
            235                 240                 245

Leu Val Asn Gly Cys Pro Tyr Thr Gly Asp Asn Tyr Gln Thr Lys Leu
        250                 255                 260

Ile Pro Val Gln Lys Ala Ser Asn Leu Leu Phe Pro Ser His Tyr Gln
265                 270                 275                 280

Arg Phe Ser Val Ser Thr Phe Ser Phe Val Asp Ser Val Ala Lys Gln
                285                 290                 295

Ala Leu Lys Gly Pro Val Tyr Leu His Cys Thr Ala Ser Val Cys Lys
                300                 305                 310

Pro Ala Gly Ala Pro Ile Cys Val Thr Thr Cys Pro Ala Ala Arg Arg
            315                 320                 325

Arg Arg Ser Ser Asp Ile His Phe Gln Asn Gly Thr Ala Ser Ile Ser
        330                 335                 340

Ser Lys Gly Pro Met Ile Leu Leu Gln Ala Thr Arg Asp Ser Ser Glu
345                 350                 355                 360

Arg Leu His Lys Tyr Ser Arg Pro Pro Val Asp Ser His Ala Leu Trp
                365                 370                 375

Val Ala Gly Leu Leu Gly Ser Leu Ile Ile Gly Ala Leu Leu Val Ser
                380                 385                 390

Tyr Leu Val Phe Arg Lys Trp Arg
        395                 400

(2) INFORMATION FOR SEQ ID NO:5:

(i) SEQUENCE CHARACTERISTICS:
        (A) LENGTH: 1326 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Sus scrofa
         (D) DEVELOPMENTAL STAGE: Juvenile
         (E) HAPLOTYPE: Diploidy
         (F) TISSUE TYPE: Ovary
         (G) CELL TYPE: Oocyte (ix) FEATURE:
         (A) NAME/KEY: sig_peptide
```

-continued (B) LOCATION: 25..105

(ix) FEATURE:
    (A) NAME/KEY: mat_peptide
    (B) LOCATION: 106..1290

(ix) FEATURE:
    (A) NAME/KEY: CDS
    (B) LOCATION: 25..1290

(xi) SEQUENCE DESCRIPTION: SEQ ID NO:5:

```
GAATTCCGGG GCCTTGTGAG TGCC ATG GCG CCG AGC TGG AGG TTC TTC GTC                51
                          Met Ala Pro Ser Trp Arg Phe Phe Val
                          -27     -25                     -20

TGC TTT CTG CTC TGG GGA GGT ACA GAG CTA TGC AGC CCG CAG CCC GTC                99
Cys Phe Leu Leu Trp Gly Gly Thr Glu Leu Cys Ser Pro Gln Pro Val
            -15                 -10                 -5

TGG CAG GAC GAA GGC CAG CGC TTG AGG CCC TCA AAG CCA CCC ACC GTA               147
Trp Gln Asp Glu Gly Gln Arg Leu Arg Pro Ser Lys Pro Pro Thr Val
        1               5                   10

ATG GTG GAG TGT CAG GAG GCC CAG CTG GTG GTC ATT GTC AGC AAA GAC               195
Met Val Glu Cys Gln Glu Ala Gln Leu Val Val Ile Val Ser Lys Asp
15              20                  25                  30

CTT TTC GGT ACC GGG AAG CTC ATC AGG CCT GCA GAT CTC AGC CTG GGC               243
Leu Phe Gly Thr Gly Lys Leu Ile Arg Pro Ala Asp Leu Ser Leu Gly
                35                  40                  45

CCT GCA AAG TGT GAG CCG CTG GTC TCT CAG GAC ACG GAC GCA GTG GTC               291
Pro Ala Lys Cys Glu Pro Leu Val Ser Gln Asp Thr Asp Ala Val Val
50              55                  60

AGG TTT GAG GTT GGG CTG CAC GAG TGT GGC AGC AGC TTG CAG GTG ACT               339
Arg Phe Glu Val Gly Leu His Glu Cys Gly Ser Ser Leu Gln Val Thr
            65                  70                  75

GAT GAT GCT CTG GTG TAC AGC ACC TTC CTG CGC CAT GAC CCC CGC CCT               387
Asp Asp Ala Leu Val Tyr Ser Thr Phe Leu Arg His Asp Pro Arg Pro
80              85                  90

GCA GGA AAC CTG TCC ATC CTG AGG ACG AAC CGT GCG GAG GTC CCC ATC               435
Ala Gly Asn Leu Ser Ile Leu Arg Thr Asn Arg Ala Glu Val Pro Ile
95              100                 105                 110

GAG TGT CAC TAC CCC AGG CAG GGC AAC GTG AGC AGC TGG GCC ATC CTG               483
Glu Cys His Tyr Pro Arg Gln Gly Asn Val Ser Ser Trp Ala Ile Leu
            115                 120                 125

CCC ACC TGG GTG CCC TTC AGG ACC ACG GTG TTC TCC GAG GAG AAG CTG               531
Pro Thr Trp Val Pro Phe Arg Thr Thr Val Phe Ser Glu Glu Lys Leu
            130                 135                 140

GTG TTC TCT CTG CGC CTG ATG GAG GAA AAC TGG AGT GCC GAG AAG ATG               579
Val Phe Ser Leu Arg Leu Met Glu Glu Asn Trp Ser Ala Glu Lys Met
            145                 150                 155

ACG CCC ACC TTC CAG CTG GGG GAC AGA GCC CAC CTC CAG GCC CAA GTC               627
Thr Pro Thr Phe Gln Leu Gly Asp Arg Ala His Leu Gln Ala Gln Val
160             165                 170

CAC ACC GGC AGC CAC GTG CCA CTG AGG CTG TTT GTG GAC CAC TGT GTG               675
His Thr Gly Ser His Val Pro Leu Arg Leu Phe Val Asp His Cys Val
175             180                 185                 190

GCC ACG CTG ACG CCG GAC TGG AAC ACC TCC CCC TCT CAC ACC ATC GTG               723
Ala Thr Leu Thr Pro Asp Trp Asn Thr Ser Pro Ser His Thr Ile Val
                195                 200                 205

GAC TTC CAC GGC TGT CTC GTG GAC GGT CTC ACT GAG GCC TCA TCT GCT               771
Asp Phe His Gly Cys Leu Val Asp Gly Leu Thr Glu Ala Ser Ser Ala
            210                 215                 220

TTC AAA GCA CCT AGA CCT GGA CCA GAG ACG CTC CAG TTC ACC GTG GAT               819
Phe Lys Ala Pro Arg Pro Gly Pro Glu Thr Leu Gln Phe Thr Val Asp
            225                 230                 235
```

```
GTG TTC CAT TTT GCT AAT GAT TCC AGA AAC ACG ATC TAC ATC ACC TGC        867
Val Phe His Phe Ala Asn Asp Ser Arg Asn Thr Ile Tyr Ile Thr Cys
240                 245                 250

CAT CTG AAG GTC ACT CCG GCT GAC CGA GTC CCG GAC CAA CTC AAC AAA        915
His Leu Lys Val Thr Pro Ala Asp Arg Val Pro Asp Gln Leu Asn Lys
255                 260                 265                 270

GCC TGT TCC TTC AGC AAG TCC TCC AAC AGG TGG TCC CCG GTG GAA GGG        963
Ala Cys Ser Phe Ser Lys Ser Ser Asn Arg Trp Ser Pro Val Glu Gly
                275                 280                 285

CCT GCT GTT ATC TGT CGT TGC TGT CAC AAG GGG CAG TGT GGT ACC CCA       1011
Pro Ala Val Ile Cys Arg Cys Cys His Lys Gly Gln Cys Gly Thr Pro
                290                 295                 300

AGC CTT TCC AGG AAG CTG TCT ATG CCG AAG AGA CAG TCT GCT CCC CGC       1059
Ser Leu Ser Arg Lys Leu Ser Met Pro Lys Arg Gln Ser Ala Pro Arg
    305                 310                 315

AGT CGC AGG CAC GTG ACA GAT GAA GCA GAT GTC ACA GTG GGG CCT CTG       1107
Ser Arg Arg His Val Thr Asp Glu Ala Asp Val Thr Val Gly Pro Leu
320                 325                 330

ATC TTC CTG GGC AAG ACG AGT GAC CAC GGT GTG GAA GGG TCC ACC TCC       1155
Ile Phe Leu Gly Lys Thr Ser Asp His Gly Val Glu Gly Ser Thr Ser
335                 340                 345                 350

TCC CCC ACC TCG GTG ATG GTG GGC TTG GGC CTG GCC ACC GTG GTG ACC       1203
Ser Pro Thr Ser Val Met Val Gly Leu Gly Leu Ala Thr Val Val Thr
                355                 360                 365

TTG ACT CTG GCT ACC ATT GTC CTG GGT GTG CCC AGG AGG CGT CGG GCT       1251
Leu Thr Leu Ala Thr Ile Val Leu Gly Val Pro Arg Arg Arg Arg Ala
                370                 375                 380

GCT GCC CAC CTT GTG TGC CCC GTG TCT GCT TCC CAA TAAAAGGAGA            1297
Ala Ala His Leu Val Cys Pro Val Ser Ala Ser Gln
                385                 390

AACATGAAAA AAAAAAAAAA CCGGAATTC                                       1326
```

(2) INFORMATION FOR SEQ ID NO:6:

(i) SEQUENCE CHARACTERISTICS:
       (A) LENGTH: 421 amino acids
       (B) TYPE: amino acid
       (D) TOPOLOGY: linear (ii) MOLECULE TYPE: protein (xi) SEQUENCE DESCRIPTION: SEQ ID NO:6:

```
Met Ala Pro Ser Trp Arg Phe Phe Val Cys Phe Leu Leu Trp Gly Gly
-27         -25                 -20                 -15

Thr Glu Leu Cys Ser Pro Gln Pro Val Trp Gln Asp Glu Gly Gln Arg
    -10                  -5                   1                   5

Leu Arg Pro Ser Lys Pro Pro Thr Val Met Val Glu Cys Gln Glu Ala
                10                  15                  20

Gln Leu Val Val Ile Val Ser Lys Asp Leu Phe Gly Thr Gly Lys Leu
                25                  30                  35

Ile Arg Pro Ala Asp Leu Ser Leu Gly Pro Ala Lys Cys Glu Pro Leu
                40                  45                  50

Val Ser Gln Asp Thr Asp Ala Val Arg Phe Glu Val Gly Leu His
    55                  60                  65

Glu Cys Gly Ser Ser Leu Gln Val Thr Asp Asp Ala Leu Val Tyr Ser
70                  75                  80                  85

Thr Phe Leu Arg His Asp Pro Arg Pro Ala Gly Asn Leu Ser Ile Leu
                90                  95                  100

Arg Thr Asn Arg Ala Glu Val Pro Ile Glu Cys His Tyr Pro Arg Gln
                105                 110                 115
```

-continued

```
Gly Asn Val Ser Ser Trp Ala Ile Leu Pro Thr Trp Val Pro Phe Arg
        120                 125                 130

Thr Thr Val Phe Ser Glu Glu Lys Leu Val Phe Ser Leu Arg Leu Met
        135                 140                 145

Glu Glu Asn Trp Ser Ala Glu Lys Met Thr Pro Thr Phe Gln Leu Gly
150                 155                 160                 165

Asp Arg Ala His Leu Gln Ala Gln Val His Thr Gly Ser His Val Pro
                170                 175                 180

Leu Arg Leu Phe Val Asp His Cys Val Ala Thr Leu Thr Pro Asp Trp
                185                 190                 195

Asn Thr Ser Pro Ser His Thr Ile Val Asp Phe His Gly Cys Leu Val
                200                 205                 210

Asp Gly Leu Thr Glu Ala Ser Ser Ala Phe Lys Ala Pro Arg Pro Gly
                215                 220                 225

Pro Glu Thr Leu Gln Phe Thr Val Asp Val Phe His Phe Ala Asn Asp
230                 235                 240                 245

Ser Arg Asn Thr Ile Tyr Ile Thr Cys His Leu Lys Val Thr Pro Ala
                250                 255                 260

Asp Arg Val Pro Asp Gln Leu Asn Lys Ala Cys Ser Phe Ser Lys Ser
                265                 270                 275

Ser Asn Arg Trp Ser Pro Val Glu Gly Pro Ala Val Ile Cys Arg Cys
                280                 285                 290

Cys His Lys Gly Gln Cys Gly Thr Pro Ser Leu Ser Arg Lys Leu Ser
                295                 300                 305

Met Pro Lys Arg Gln Ser Ala Pro Arg Ser Arg Arg His Val Thr Asp
310                 315                 320                 325

Glu Ala Asp Val Thr Val Gly Pro Leu Ile Phe Leu Gly Lys Thr Ser
                330                 335                 340

Asp His Gly Val Glu Gly Ser Ser Ser Pro Thr Ser Val Met Val
                345                 350                 355

Gly Leu Gly Leu Ala Thr Val Val Thr Leu Thr Leu Ala Thr Ile Val
                360                 365                 370

Leu Gly Val Pro Arg Arg Arg Ala Ala Ala His Leu Val Cys Pro
                375                 380                 385

Val Ser Ala Ser Gln
390
```

(2) INFORMATION FOR SEQ ID NO:7:

(i) SEQUENCE CHARACTERISTICS:
        (A) LENGTH: 1338 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Oryctolagus cuniculus
        (D) DEVELOPMENTAL STAGE: Juvenile
        (E) HAPLOTYPE: Diploidy
        (F) TISSUE TYPE: Ovary
        (G) CELL TYPE: Oocyte (ix) FEATURE:
        (A) NAME/KEY: CDS
        (B) LOCATION: 17..1261

(xi) SEQUENCE DESCRIPTION: SEQ ID NO:7:

```
GAATTCGCGG CCGGCC TAC GGG CTC TTC GTT TGC CTA CTG CTC TGG GGA                49
               Tyr Gly Leu Phe Val Cys Leu Leu Leu Trp Gly
                1               5                   10

GGC TCG GAG CTG TGC TGC CCC CAG CCG CTC TGG TTC TGG CAG GGC GGG             97
Gly Ser Glu Leu Cys Cys Pro Gln Pro Leu Trp Phe Trp Gln Gly Gly
            15                  20                  25

ACC CGC CAG CCC GCG CCC TCC GTG ACG CCC GTG GTG GTG GAG TGT CTG            145
Thr Arg Gln Pro Ala Pro Ser Val Thr Pro Val Val Val Glu Cys Leu
        30                  35                  40

GAG GCC CGG CTC GTG GTC ACG GTC AGC AGG GAC CTT TTT GGC ACC GGG            193
Glu Ala Arg Leu Val Val Thr Val Ser Arg Asp Leu Phe Gly Thr Gly
    45                  50                  55

AAG CTC ATC CAG GAG GCC GAC CTC AGC CTG GGC CCC GAG GGC TGC GAG            241
Lys Leu Ile Gln Glu Ala Asp Leu Ser Leu Gly Pro Glu Gly Cys Glu
60                  65                  70                  75

CCC CAG GCC TCC ACG GAC GCC GTG GTC AGG TTC GAG GTC GGG CTG CAT            289
Pro Gln Ala Ser Thr Asp Ala Val Val Arg Phe Glu Val Gly Leu His
                80                  85                  90

GAA TGT GGT AAC AGC GTG CAG GTG ACT GAC GAC TCC CTG GTG TAC AGC            337
Glu Cys Gly Asn Ser Val Gln Val Thr Asp Asp Ser Leu Val Tyr Ser
            95                  100                 105

TCC TTC CTG CTC CAC GAC CCC CGC CCC GCG GGA AAC CTG TCC ATC CTC            385
Ser Phe Leu Leu His Asp Pro Arg Pro Ala Gly Asn Leu Ser Ile Leu
        110                 115                 120

AGG ACC AAC CGC GCC GAG GTC CCC ATC GAG TGC CGC TAC CCC AGG CAG            433
Arg Thr Asn Arg Ala Glu Val Pro Ile Glu Cys Arg Tyr Pro Arg Gln
    125                 130                 135

GGC AAC GTG AGC AGC CGG GCG ATC CTG CCG ACC TGG GTG CCC TTC TGG            481
Gly Asn Val Ser Ser Arg Ala Ile Leu Pro Thr Trp Val Pro Phe Trp
140                 145                 150                 155

ACC ACG GTA CTG TCA GAG GAG AGG CTG GTG TTC TCC CTG CGC CTC ATG            529
Thr Thr Val Leu Ser Glu Glu Arg Leu Val Phe Ser Leu Arg Leu Met
                160                 165                 170

GAG GAG AAC TGG AGC CGA GAA AAG ATG TCC CCC ACC TTC CAC CTG GGC            577
Glu Glu Asn Trp Ser Arg Glu Lys Met Ser Pro Thr Phe His Leu Gly
            175                 180                 185

GAC ACG GCC CAC CTG CAG GCA GAG GTC CGC ACG GGC AGC CAC CCG CCC            625
Asp Thr Ala His Leu Gln Ala Glu Val Arg Thr Gly Ser His Pro Pro
        190                 195                 200

CTG CTG CTG TTC GTG GAT CGC TGC GTG GCC ACC CCG ACA CGG GAC CAG            673
Leu Leu Leu Phe Val Asp Arg Cys Val Ala Thr Pro Thr Arg Asp Gln
    205                 210                 215

AGC GGC TCC CCC TAT CAC ACC ATC GTG GAC TTG CAC GGC TGT CTT GTG            721
Ser Gly Ser Pro Tyr His Thr Ile Val Asp Leu His Gly Cys Leu Val
220                 225                 230                 235

GAT GGC CTC TCC GAT GGG GCT TCC AAG TTC AAA GCC CCC AGG CCG AAG            769
Asp Gly Leu Ser Asp Gly Ala Ser Lys Phe Lys Ala Pro Arg Pro Lys
                240                 245                 250

CCG GAC GTG CTC CAG TTC ATG GTG GCC GTG TTC CAC TTC GCT AAT GAC            817
Pro Asp Val Leu Gln Phe Met Val Ala Val Phe His Phe Ala Asn Asp
            255                 260                 265

TCC AGG CAC ACG GTC TAC ATC ACG TGT CAC CTG AGG GTC ATT CCT GCC            865
Ser Arg His Thr Val Tyr Ile Thr Cys His Leu Arg Val Ile Pro Ala
        270                 275                 280

CAG CAA GCC CCG GAC CGG CTC AAC AAG GCT TGT TCT TTC AAC CAG TCC            913
Gln Gln Ala Pro Asp Arg Leu Asn Lys Ala Cys Ser Phe Asn Gln Ser
    285                 290                 295

TCC AGC AGC TGG GCC CCG GTG GAA GGC AGT GCA GAC ATC TGT GAG TGT            961
```

```
Ser Ser Ser Trp Ala Pro Val Glu Gly Ser Ala Asp Ile Cys Glu Cys
300                 305                 310                 315

TGC GGC AAC GGT GAC TGT GAC CTC ATC GCA GGC TCC CCC ATG AAC CAG        1009
Cys Gly Asn Gly Asp Cys Asp Leu Ile Ala Gly Ser Pro Met Asn Gln
                320                 325                 330

AAC CAT GCT GCC CGG TCC TCT CTG CGA AGC CGC AGG CAC GTG ACG GAA        1057
Asn His Ala Ala Arg Ser Ser Leu Arg Ser Arg Arg His Val Thr Glu
            335                 340                 345

GAA GCA GAC GTC ACC GTG GGC CCG CTG ATC TTC CTG GGG AAG GCT GGT        1105
Glu Ala Asp Val Thr Val Gly Pro Leu Ile Phe Leu Gly Lys Ala Gly
        350                 355                 360

GAC CCT GCC GGC ACA GAG GGG CTG GCC TCT GCT GCG CAG GCG ACC CTG        1153
Asp Pro Ala Gly Thr Glu Gly Leu Ala Ser Ala Ala Gln Ala Thr Leu
    365                 370                 375

GTG CTG GGC CTT CGC ATG GCC ACC ATT GTG TTC CTG GCT GTG GCT GCT        1201
Val Leu Gly Leu Arg Met Ala Thr Ile Val Phe Leu Ala Val Ala Ala
380                 385                 390                 395

GTG GTC CTG GGC CTC ACC AGG GGG CGC CAC GCT GCT TCC CAC CCC AGG        1249
Val Val Leu Gly Leu Thr Arg Gly Arg His Ala Ala Ser His Pro Arg
                400                 405                 410

TCT GCT TCC CAA TAAAAAATCA TGACTTCAAA AAAAAAAAAA AAAAAAAAA             1301
Ser Ala Ser Gln
            415

AAAAAAAAAA AAAAAAAAAA AAAGCGGCCG CGAATTC                               1338

(2) INFORMATION FOR SEQ ID NO:8:

(i) SEQUENCE CHARACTERISTICS:
        (A) LENGTH: 415 amino acids
        (B) TYPE: amino acid
        (D) TOPOLOGY: linear (ii) MOLECULE TYPE: protein (xi) SEQUENCE DESCRIPTION: SEQ ID NO:8:

Tyr Gly Leu Phe Val Cys Leu Leu Trp Gly Gly Ser Glu Leu Cys
 1               5                  10                  15

Cys Pro Gln Pro Leu Trp Phe Trp Gln Gly Thr Arg Gln Pro Ala
                20                  25                  30

Pro Ser Val Thr Pro Val Val Glu Cys Leu Glu Ala Arg Leu Val
            35                  40                  45

Val Thr Val Ser Arg Asp Leu Phe Gly Thr Gly Lys Leu Ile Gln Glu
        50                  55                  60

Ala Asp Leu Ser Leu Gly Pro Glu Gly Cys Glu Pro Gln Ala Ser Thr
65                  70                  75                  80

Asp Ala Val Val Arg Phe Glu Val Gly Leu His Glu Cys Gly Asn Ser
                85                  90                  95

Val Gln Val Thr Asp Asp Ser Leu Val Tyr Ser Ser Phe Leu Leu His
            100                 105                 110

Asp Pro Arg Pro Ala Gly Asn Leu Ser Ile Leu Arg Thr Asn Arg Ala
        115                 120                 125

Glu Val Pro Ile Glu Cys Arg Tyr Pro Arg Gln Gly Asn Val Ser Ser
    130                 135                 140

Arg Ala Ile Leu Pro Thr Trp Val Pro Phe Trp Thr Thr Val Leu Ser
145                 150                 155                 160

Glu Glu Arg Leu Val Phe Ser Leu Arg Leu Met Glu Glu Asn Trp Ser
                165                 170                 175

Arg Glu Lys Met Ser Pro Thr Phe His Leu Gly Asp Thr Ala His Leu
            180                 185                 190
```

```
Gln Ala Glu Val Arg Thr Gly Ser His Pro Pro Leu Leu Leu Phe Val
        195                 200                 205

Asp Arg Cys Val Ala Thr Pro Thr Arg Asp Gln Ser Gly Ser Pro Tyr
210                 215                 220

His Thr Ile Val Asp Leu His Gly Cys Leu Val Asp Gly Leu Ser Asp
225                 230                 235                 240

Gly Ala Ser Lys Phe Lys Ala Pro Arg Pro Lys Pro Asp Val Leu Gln
                245                 250                 255

Phe Met Val Ala Val Phe His Phe Ala Asn Asp Ser Arg His Thr Val
            260                 265                 270

Tyr Ile Thr Cys His Leu Arg Val Ile Pro Ala Gln Gln Ala Pro Asp
                275                 280                 285

Arg Leu Asn Lys Ala Cys Ser Phe Asn Gln Ser Ser Ser Trp Ala
290                 295                 300

Pro Val Glu Gly Ser Ala Asp Ile Cys Glu Cys Cys Gly Asn Gly Asp
305                 310                 315                 320

Cys Asp Leu Ile Ala Gly Ser Pro Met Asn Gln Asn His Ala Ala Arg
                325                 330                 335

Ser Ser Leu Arg Ser Arg Arg His Val Thr Glu Glu Ala Asp Val Thr
                340                 345                 350

Val Gly Pro Leu Ile Phe Leu Gly Lys Ala Gly Asp Pro Ala Gly Thr
                355                 360                 365

Glu Gly Leu Ala Ser Ala Ala Gln Ala Thr Leu Val Leu Gly Leu Arg
370                 375                 380

Met Ala Thr Ile Val Phe Leu Ala Val Ala Val Val Leu Gly Leu
385                 390                 395                 400

Thr Arg Gly Arg His Ala Ala Ser His Pro Arg Ser Ala Ser Gln
                405                 410                 415

(2) INFORMATION FOR SEQ ID NO:9:

(i) SEQUENCE CHARACTERISTICS:
        (A) LENGTH: 2381 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Canis familiaris
        (D) DEVELOPMENTAL STAGE: Juvenile
        (E) HAPLOTYPE: Diploidy
        (F) TISSUE TYPE: Ovary
        (G) CELL TYPE: Oocyte (ix) FEATURE:
        (A) NAME/KEY: CDS
        (B) LOCATION: 206..2353

(xi) SEQUENCE DESCRIPTION: SEQ ID NO:9:

GAATTCCGGG AGCCCTGAAG GAAGCCGCAA GAACCCTGCC CGCACCTCCG CGACCTCAAG      60

ATGTCCACTC CACTGGAAGA CGGAGAATAC TGGATTGACC CCAACCAAGG ATGCAACCTG     120

ATGCCATCAA GGTTTTCTGC AACATGGAGA CAGGTGAGAC CTGCGTATAC CCACCTACCT     180

GGCTGATTTG GTGGTACGTT TGGCC ATG GCA TGC AAA CAG AAA GGA GAC AGT        232
                            Met Ala Cys Lys Gln Lys Gly Asp Ser
                             1               5
```

```
GGG AGT CCC TCA AGC AGG TTT AGT GCA GAT TGG AGC ACC TAC AGG TCA        280
Gly Ser Pro Ser Ser Arg Phe Ser Ala Asp Trp Ser Thr Tyr Arg Ser
 10              15                  20                  25

CTT TCT TTA TTC TTC ATC CTT GTG ACT TCA GTG AAC TCA GTA GGT GTT        328
Leu Ser Leu Phe Phe Ile Leu Val Thr Ser Val Asn Ser Val Gly Val
                 30                  35                  40

ATG CAG TTG GTG AAT CCC ATC TTC CCA GGT ACT GTC ATT TGC CAT GAA        376
Met Gln Leu Val Asn Pro Ile Phe Pro Gly Thr Val Ile Cys His Glu
                     45                  50                  55

AAT AAA ATG ACA GTG GAA TTT CCA AGG GAT CTT GGC ACC AAA AAA TGG        424
Asn Lys Met Thr Val Glu Phe Pro Arg Asp Leu Gly Thr Lys Lys Trp
             60                  65                  70

CAT GCA TCT GTG GTG GAT CCA TTT AGT TTT GAA TTG TTG AAC TGT ACT        472
His Ala Ser Val Val Asp Pro Phe Ser Phe Glu Leu Leu Asn Cys Thr
         75                  80                  85

TCT ATC CTG GAC CCA GAA AAG CTC ACC CTG AAG GCC CCA TAT GAG ACC        520
Ser Ile Leu Asp Pro Glu Lys Leu Thr Leu Lys Ala Pro Tyr Glu Thr
 90                  95                 100                 105

TGT AGC AGG AGA GTG CTT GGC CAG CAT CAG ATG GCC ATC AGA CTC ACG        568
Cys Ser Arg Arg Val Leu Gly Gln His Gln Met Ala Ile Arg Leu Thr
                110                 115                 120

GAC AAC AAT GCT GCT TCA AGA CAT AAG GCT TTC ATG TAT CAG ATC AGC        616
Asp Asn Asn Ala Ala Ser Arg His Lys Ala Phe Met Tyr Gln Ile Ser
            125                 130                 135

TGT CCA GTT ATG CAA ACA GAA GAA ACC CAT GAG CAT GCA GGA TCC ACA        664
Cys Pro Val Met Gln Thr Glu Glu Thr His Glu His Ala Gly Ser Thr
                140                 145                 150

ATC TGC ACA AAA GAT TCC ATG TCT TTT ACC TTT AAC ATT ATT CCT GGC        712
Ile Cys Thr Lys Asp Ser Met Ser Phe Thr Phe Asn Ile Ile Pro Gly
155                 160                 165

ATG GCT GAT GAA AAT ACG AAT CCC AGT GGT GGG AAA TGG ATG ATG GAG        760
Met Ala Asp Glu Asn Thr Asn Pro Ser Gly Gly Lys Trp Met Met Glu
170                 175                 180                 185

GTT GAT GAT GCA AAA GCT CAA AAT CTG ACT CTT CGG GAG GCC TTG ATG        808
Val Asp Asp Ala Lys Ala Gln Asn Leu Thr Leu Arg Glu Ala Leu Met
                190                 195                 200

CAA GGA TAT AAT TTC CTG TTT GAT AGC CAC AGG CTC AGT GTC CAA GTG        856
Gln Gly Tyr Asn Phe Leu Phe Asp Ser His Arg Leu Ser Val Gln Val
            205                 210                 215

TCA TTC AAT GCC ACT GGA GTC ACT CAC TAC ATG CAA GGT AAC AGT CAC        904
Ser Phe Asn Ala Thr Gly Val Thr His Tyr Met Gln Gly Asn Ser His
        220                 225                 230

CTC TAC ACA GTG CCT CTG AAG CTT ATA CAC ACA TCT CCT GGG CAG AAG        952
Leu Tyr Thr Val Pro Leu Lys Leu Ile His Thr Ser Pro Gly Gln Lys
    235                 240                 245

ATC ATC TTA ACA ACA CGA GTA CTT TGT ATG TCA GAT CCC GTG ACC TGT       1000
Ile Ile Leu Thr Thr Arg Val Leu Cys Met Ser Asp Pro Val Thr Cys
250                 255                 260                 265

AAC GCC ACA CAC ATG ACC CTC ACC ATA CCA GAG TTT CCT GGG AAA CTA       1048
Asn Ala Thr His Met Thr Leu Thr Ile Pro Glu Phe Pro Gly Lys Leu
                270                 275                 280

CAG TCT GTG AGA TTT GAA AAC ACG AAC TTT CGT GTA AGC CAG CTG CAC       1096
Gln Ser Val Arg Phe Glu Asn Thr Asn Phe Arg Val Ser Gln Leu His
            285                 290                 295

AAC CAT GGG ATT GAT AAA GAA GAA TTA AAC GGC TTG AGG TTA CAC TTC       1144
Asn His Gly Ile Asp Lys Glu Glu Leu Asn Gly Leu Arg Leu His Phe
        300                 305                 310

AGC AAA TCT CTT CTC AAA ATG AAC TCC TCT GAA AAA TGC CTA CTC TAT       1192
Ser Lys Ser Leu Leu Lys Met Asn Ser Ser Glu Lys Cys Leu Leu Tyr
    315                 320                 325
```

```
CAG TTC TAC TTA GCA TCT CTC AAG CTG ACC TTT GCC TTT GAA CGG GAC        1240
Gln Phe Tyr Leu Ala Ser Leu Lys Leu Thr Phe Ala Phe Glu Arg Asp
330                 335                 340                 345

ACG GTT TCC ACA GTG GTT TAT CCT GAG TGT GTT TGT GAG CCA CCA GTT        1288
Thr Val Ser Thr Val Val Tyr Pro Glu Cys Val Cys Glu Pro Pro Val
                350                 355                 360

ACT ATA GTT ACA GGT GAC CTG TGT ACC CAG GAT GGG TTT ATG GAT GTC        1336
Thr Ile Val Thr Gly Asp Leu Cys Thr Gln Asp Gly Phe Met Asp Val
            365                 370                 375

AAG GTC TAC AGC CAC CAA ACA AAA CCA GCT CTA AAC TTG GAT ACC CTC        1384
Lys Val Tyr Ser His Gln Thr Lys Pro Ala Leu Asn Leu Asp Thr Leu
        380                 385                 390

AGA GTG GGA GAC TCC TCC TGC CAA CCT ACT TTC AAG GCT CCA TCA CAA        1432
Arg Val Gly Asp Ser Ser Cys Gln Pro Thr Phe Lys Ala Pro Ser Gln
    395                 400                 405

GGG TTG ACA CTG TTT CAC ATC CCC CTA AAT GGA TGT GGA ACA AGA CTT        1480
Gly Leu Thr Leu Phe His Ile Pro Leu Asn Gly Cys Gly Thr Arg Leu
410                 415                 420                 425

AAG TTC AAA GGT GAC ACA GTC ATC TAT GAA AAT GAA ATA CAT GCT CTC        1528
Lys Phe Lys Gly Asp Thr Val Ile Tyr Glu Asn Glu Ile His Ala Leu
                430                 435                 440

TGG ACA GAT CTC CCT CCA AGC ACA ATT TCC AGA GAT AGT GAA TTC AGA        1576
Trp Thr Asp Leu Pro Pro Ser Thr Ile Ser Arg Asp Ser Glu Phe Arg
            445                 450                 455

ATG ACT GTG AAG TGC CAT TAC AGC AGA GAT GAC CTG CTG ATA AAT ACC        1624
Met Thr Val Lys Cys His Tyr Ser Arg Asp Asp Leu Leu Ile Asn Thr
        460                 465                 470

AAT GTC CAA AGT CTT CCT CCT CCC GTG GCC TCA GTG AGG CCT GGT CCA        1672
Asn Val Gln Ser Leu Pro Pro Pro Val Ala Ser Val Arg Pro Gly Pro
    475                 480                 485

CTT GCC TTA ATC CTG CAA ACC TAC CCA GAT AAA TCC TAT TTG CGA CCC        1720
Leu Ala Leu Ile Leu Gln Thr Tyr Pro Asp Lys Ser Tyr Leu Arg Pro
490                 495                 500                 505

TAT GGG GAT AAG GAG TAT CCT GTG GTG AGA TAC CTC CGC CAA CCA ATT        1768
Tyr Gly Asp Lys Glu Tyr Pro Val Val Arg Tyr Leu Arg Gln Pro Ile
                510                 515                 520

TAC CTG GAA GTG AAA GTC CTA AAT AGG GCT GAC CCC AAC ATC AAG CTG        1816
Tyr Leu Glu Val Lys Val Leu Asn Arg Ala Asp Pro Asn Ile Lys Leu
            525                 530                 535

GTC TTA GAT GAT TGC TGG GCA ACA CCC ACC ATG GAC CCA GCC TCA CTC        1864
Val Leu Asp Asp Cys Trp Ala Thr Pro Thr Met Asp Pro Ala Ser Leu
        540                 545                 550

CCC CAG TGG AAT ATT GTC ATG GAT GGC TGT GAA TAC AAT CTG GAC AAC        1912
Pro Gln Trp Asn Ile Val Met Asp Gly Cys Glu Tyr Asn Leu Asp Asn
    555                 560                 565

TAC AGA ACG ACC TTC CAT CCA GTT GGC TCC TCT GTG ACC TAC CCT ACT        1960
Tyr Arg Thr Thr Phe His Pro Val Gly Ser Ser Val Thr Tyr Pro Thr
570                 575                 580                 585

CAC TAT CAG AGG TTT GAT GTG AAG ACC TTT GCC TTT ATA TCA GAG GCC        2008
His Tyr Gln Arg Phe Asp Val Lys Thr Phe Ala Phe Ile Ser Glu Ala
                590                 595                 600

CAA GTG CTT TCT AGC CTG GTC TAC TTC CAC TGC ACC GCA TTA ATC TGC        2056
Gln Val Leu Ser Ser Leu Val Tyr Phe His Cys Thr Ala Leu Ile Cys
            605                 610                 615

AAT CGA CTG TCT CCT GAC TCC CCT CTG TGT TCT GTG ACT TGC CCT GTA        2104
Asn Arg Leu Ser Pro Asp Ser Pro Leu Cys Ser Val Thr Cys Pro Val
        620                 625                 630

TCA TCC AGG CAC AGG CGA GCC ACA GGC AGT ACT GAA GAA GAG AAG ATG        2152
Ser Ser Arg His Arg Arg Ala Thr Gly Ser Thr Glu Glu Glu Lys Met
    635                 640                 645
```

```
ATA GTA AGT CTC CCG GGA CCC ATC CTC CTG TTG GCA GAC AGC TCT TCA    2200
Ile Val Ser Leu Pro Gly Pro Ile Leu Leu Leu Ala Asp Ser Ser Ser
650                 655                 660                 665

CTC AGA GAT GGT GTG GAC TCA AAA GGG CAC AGG GCT GCT GGA TAT GTT    2248
Leu Arg Asp Gly Val Asp Ser Lys Gly His Arg Ala Ala Gly Tyr Val
                670                 675                 680

GCT TTT AAA ACT GTA GTG GCT GTG GCT GCC TTA GCA GGC CTT GTG GCT    2296
Ala Phe Lys Thr Val Val Ala Val Ala Ala Leu Ala Gly Leu Val Ala
            685                 690                 695

GCT CTA GGT CTC ATC ATC TAC CTG CGT AAG AAA AGA ACC ATG GTG TTA    2344
Ala Leu Gly Leu Ile Ile Tyr Leu Arg Lys Lys Arg Thr Met Val Leu
        700                 705                 710

AAT CAC TAAGGATTTT CAAATAAAGT GTCCGGAATT C                         2381
Asn His
    715
```

(2) INFORMATION FOR SEQ ID NO:10:

(i) SEQUENCE CHARACTERISTICS:
        (A) LENGTH: 715 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ala Cys Lys Gln Lys Gly Asp Ser Gly Ser Pro Ser Ser Arg Phe
 1               5                  10                  15

Ser Ala Asp Trp Ser Thr Tyr Arg Ser Leu Ser Leu Phe Phe Ile Leu
                20                  25                  30

Val Thr Ser Val Asn Ser Val Gly Val Met Gln Leu Val Asn Pro Ile
            35                  40                  45

Phe Pro Gly Thr Val Ile Cys His Glu Asn Lys Met Thr Val Glu Phe
        50                  55                  60

Pro Arg Asp Leu Gly Thr Lys Lys Trp His Ala Ser Val Val Asp Pro
65                  70                  75                  80

Phe Ser Phe Glu Leu Leu Asn Cys Thr Ser Ile Leu Asp Pro Glu Lys
                85                  90                  95

Leu Thr Leu Lys Ala Pro Tyr Glu Thr Cys Ser Arg Arg Val Leu Gly
            100                 105                 110

Gln His Gln Met Ala Ile Arg Leu Thr Asp Asn Asn Ala Ala Ser Arg
        115                 120                 125

His Lys Ala Phe Met Tyr Gln Ile Ser Cys Pro Val Met Gln Thr Glu
    130                 135                 140

Glu Thr His Glu His Ala Gly Ser Thr Ile Cys Thr Lys Asp Ser Met
145                 150                 155                 160

Ser Phe Thr Phe Asn Ile Ile Pro Gly Met Ala Asp Glu Asn Thr Asn
                165                 170                 175

Pro Ser Gly Gly Lys Trp Met Met Glu Val Asp Asp Ala Lys Ala Gln
            180                 185                 190

Asn Leu Thr Leu Arg Glu Ala Leu Met Gln Gly Tyr Asn Phe Leu Phe
        195                 200                 205

Asp Ser His Arg Leu Ser Val Gln Val Ser Phe Asn Ala Thr Gly Val
    210                 215                 220

Thr His Tyr Met Gln Gly Asn Ser His Leu Tyr Thr Val Pro Leu Lys
225                 230                 235                 240

Leu Ile His Thr Ser Pro Gly Gln Lys Ile Ile Leu Thr Thr Arg Val
                245                 250                 255
```

```
Leu Cys Met Ser Asp Pro Val Thr Cys Asn Ala Thr His Met Thr Leu
            260                 265                 270

Thr Ile Pro Glu Phe Pro Gly Lys Leu Gln Ser Val Arg Phe Glu Asn
            275                 280                 285

Thr Asn Phe Arg Val Ser Gln Leu His Asn His Gly Ile Asp Lys Glu
            290                 295                 300

Glu Leu Asn Gly Leu Arg Leu His Phe Ser Lys Ser Leu Leu Lys Met
305                 310                 315                 320

Asn Ser Ser Glu Lys Cys Leu Leu Tyr Gln Phe Tyr Leu Ala Ser Leu
                    325                 330                 335

Lys Leu Thr Phe Ala Phe Glu Arg Asp Thr Val Ser Thr Val Val Tyr
            340                 345                 350

Pro Glu Cys Val Cys Glu Pro Val Thr Ile Val Thr Gly Asp Leu
            355                 360                 365

Cys Thr Gln Asp Gly Phe Met Asp Val Lys Val Tyr Ser His Gln Thr
            370                 375                 380

Lys Pro Ala Leu Asn Leu Asp Thr Leu Arg Val Gly Asp Ser Ser Cys
385                 390                 395                 400

Gln Pro Thr Phe Lys Ala Pro Ser Gln Gly Leu Thr Leu Phe His Ile
                    405                 410                 415

Pro Leu Asn Gly Cys Gly Thr Arg Leu Lys Phe Lys Gly Asp Thr Val
            420                 425                 430

Ile Tyr Glu Asn Glu Ile His Ala Leu Trp Thr Asp Leu Pro Pro Ser
            435                 440                 445

Thr Ile Ser Arg Asp Ser Glu Phe Arg Met Thr Val Lys Cys His Tyr
            450                 455                 460

Ser Arg Asp Asp Leu Leu Ile Asn Thr Asn Val Gln Ser Leu Pro Pro
465                 470                 475                 480

Pro Val Ala Ser Val Arg Pro Gly Pro Leu Ala Leu Ile Leu Gln Thr
                    485                 490                 495

Tyr Pro Asp Lys Ser Tyr Leu Arg Pro Tyr Gly Asp Lys Glu Tyr Pro
            500                 505                 510

Val Val Arg Tyr Leu Arg Gln Pro Ile Tyr Leu Glu Val Lys Val Leu
            515                 520                 525

Asn Arg Ala Asp Pro Asn Ile Lys Leu Val Leu Asp Asp Cys Trp Ala
530                 535                 540

Thr Pro Thr Met Asp Pro Ala Ser Leu Pro Gln Trp Asn Ile Val Met
545                 550                 555                 560

Asp Gly Cys Glu Tyr Asn Leu Asp Asn Tyr Arg Thr Thr Phe His Pro
                    565                 570                 575

Val Gly Ser Ser Val Thr Tyr Pro Thr His Tyr Gln Arg Phe Asp Val
            580                 585                 590

Lys Thr Phe Ala Phe Ile Ser Glu Ala Gln Val Leu Ser Ser Leu Val
            595                 600                 605

Tyr Phe His Cys Thr Ala Leu Ile Cys Asn Arg Leu Ser Pro Asp Ser
            610                 615                 620

Pro Leu Cys Ser Val Thr Cys Pro Val Ser Ser Arg His Arg Arg Ala
625                 630                 635                 640

Thr Gly Ser Thr Glu Glu Lys Met Ile Val Ser Leu Pro Gly Pro
                    645                 650                 655

Ile Leu Leu Leu Ala Asp Ser Ser Leu Arg Asp Gly Val Asp Ser
            660                 665                 670

Lys Gly His Arg Ala Ala Gly Tyr Val Ala Phe Lys Thr Val Val Ala
```

```
                    675                 680                 685
Val Ala Ala Leu Ala Gly Leu Val Ala Ala Leu Gly Leu Ile Ile Tyr
    690                 695                 700

Leu Arg Lys Lys Arg Thr Met Val Leu Asn His
705                 710                 715
```

(2) INFORMATION FOR SEQ ID NO:11:

(i) SEQUENCE CHARACTERISTICS:
        (A) LENGTH: 1325 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Canis familiaris
        (D) DEVELOPMENTAL STAGE: Juvenile
        (E) HAPLOTYPE: Diploidy
        (F) TISSUE TYPE: Ovary
        (G) CELL TYPE: Oocyte (ix) FEATURE:
        (A) NAME/KEY: CDS
        (B) LOCATION: 13..1293

(xi) SEQUENCE DESCRIPTION: SEQ ID NO:11:

```
GAATTCCGGG CT ATG GGG CTG AGC TAT GGA ATT TTC ATC TGT TTT CTG        48
              Met Gly Leu Ser Tyr Gly Ile Phe Ile Cys Phe Leu
                1               5                  10

CTC CTG GGA GGC ATG GAG CTG TGC TGC CCC CAG ACC ATC TGG CCA ACT       96
Leu Leu Gly Gly Met Glu Leu Cys Cys Pro Gln Thr Ile Trp Pro Thr
            15                  20                  25

GAG ACC TAC TAC CCA TTG ACA TCT AGG CCC CCA GTA ATG GTG GAC TGT      144
Glu Thr Tyr Tyr Pro Leu Thr Ser Arg Pro Pro Val Met Val Asp Cys
    30                  35                  40

CTG GAG TCC CAG CTG GTG GTC ACT GTC AGC AAA GAC CTT TTT GGT ACT      192
Leu Glu Ser Gln Leu Val Val Thr Val Ser Lys Asp Leu Phe Gly Thr
45                  50                  55                  60

GGG AAG CTC ATC AGG CCA GCA GAC CTC ACC CTG GGT CCA GAG AAC TGT      240
Gly Lys Leu Ile Arg Pro Ala Asp Leu Thr Leu Gly Pro Glu Asn Cys
                65                  70                  75

GAG CCC CTG GTC TCC ATG GAC ACG GAT GAT GTG GTC AGG TTT GAG GTT      288
Glu Pro Leu Val Ser Met Asp Thr Asp Asp Val Val Arg Phe Glu Val
            80                  85                  90

GGG CTG CAC GAG TGT GGC AGC AGG GTG CAG GTG ACT GAC AAT GCT CTG      336
Gly Leu His Glu Cys Gly Ser Arg Val Gln Val Thr Asp Asn Ala Leu
    95                  100                 105

GTG TAC AGC ACC TTC CTG ATC CAC AGC CCC CGC CCT GCG GGC AAC CTG      384
Val Tyr Ser Thr Phe Leu Ile His Ser Pro Arg Pro Ala Gly Asn Leu
110                 115                 120

TCC ATC CTG AGA ACT AAT CGT GCC GAG GTT CCC ATC GAG TGC CAC TAC      432
Ser Ile Leu Arg Thr Asn Arg Ala Glu Val Pro Ile Glu Cys His Tyr
125                 130                 135                 140

CCC AGG CAC AGC AAT GTG AGC AGC CAG GCC ATC CTG CCC ACT TGG GTG      480
Pro Arg His Ser Asn Val Ser Ser Gln Ala Ile Leu Pro Thr Trp Val
                145                 150                 155

CCC TTC AGG ACC ACA ATG CTC TTC GAG GAG AAG CTA GTT TTC TCT CTC      528
Pro Phe Arg Thr Thr Met Leu Phe Glu Glu Lys Leu Val Phe Ser Leu
            160                 165                 170
```

```
CGC CTA ATG GAG GAG GAC TGG GGC TCC GAG AAG CAA TCC CCC ACA TTC        576
Arg Leu Met Glu Glu Asp Trp Gly Ser Glu Lys Gln Ser Pro Thr Phe
        175                 180                 185

CAG CTG GGA GAC ATA GCC CAC CTC CAG GCT GAA GTC CAC ACT GGC AGC        624
Gln Leu Gly Asp Ile Ala His Leu Gln Ala Glu Val His Thr Gly Ser
        190                 195                 200

CAT ATG CCA CTG CGA CTT TTT GTG GAC CAC TGT GTG GCC ACG CTG ACA        672
His Met Pro Leu Arg Leu Phe Val Asp His Cys Val Ala Thr Leu Thr
205                 210                 215                 220

CCA GAT CGG AAT GCC TTC CTT CAT CAC AAA ATT GTG GAC TTC CAT GGC        720
Pro Asp Arg Asn Ala Phe Leu His His Lys Ile Val Asp Phe His Gly
                225                 230                 235

TGT CTT GTG GAT GGT CTC TAC AAT TCC TCT TCA GCC TTC AAA GCC CCC        768
Cys Leu Val Asp Gly Leu Tyr Asn Ser Ser Ser Ala Phe Lys Ala Pro
            240                 245                 250

AGA CCC AGG CCA GAG ACT CTT CAG TTC ACA GTG GAT GTT TTC CAC TTT        816
Arg Pro Arg Pro Glu Thr Leu Gln Phe Thr Val Asp Val Phe His Phe
        255                 260                 265

GCT AAG GAC TCA AGA AAC ACG ATC TAT ATC ACC TGC CAT CTG AAG GTC        864
Ala Lys Asp Ser Arg Asn Thr Ile Tyr Ile Thr Cys His Leu Lys Val
        270                 275                 280

ACT CCG GCT GAC CGA GTC CCA GAC CAG CTA AAC AAA GCT TGT TCC TTC        912
Thr Pro Ala Asp Arg Val Pro Asp Gln Leu Asn Lys Ala Cys Ser Phe
285                 290                 295                 300

ATC AAG TCT ACC AAG AGG TGG TAC CCT GTA GAA GGC TCG GCT GAT ATT        960
Ile Lys Ser Thr Lys Arg Trp Tyr Pro Val Glu Gly Ser Ala Asp Ile
                305                 310                 315

TGT CGC TGT TGT AAC AAA GGC AGC TGT GGC CTT CCA GGC CGG TCC AGG       1008
Cys Arg Cys Cys Asn Lys Gly Ser Cys Gly Leu Pro Gly Arg Ser Arg
            320                 325                 330

AGG CTG TCC CAC CTA GAG AGA GGG TGG CGC AAG TCT GTT TCC CAC ACT       1056
Arg Leu Ser His Leu Glu Arg Gly Trp Arg Lys Ser Val Ser His Thr
        335                 340                 345

AGA AAT CGC AGG CAC GTG ACT GAA GAA GCA GAG ATC ACC GTG GGG CCT       1104
Arg Asn Arg Arg His Val Thr Glu Glu Ala Glu Ile Thr Val Gly Pro
350                 355                 360

CTG ATC TTC CTG GGA AAG GCT AGT GAT CAT GGT ATA GAG GGG TCA ACC       1152
Leu Ile Phe Leu Gly Lys Ala Ser Asp His Gly Ile Glu Gly Ser Thr
365                 370                 375                 380

TCT CCT CAC ACC TCT GTG ATG TTG GGC TTA GGC CTG GCC ACG GTG GTA       1200
Ser Pro His Thr Ser Val Met Leu Gly Leu Gly Leu Ala Thr Val Val
                385                 390                 395

TCC CTG ACT CTA GCT ACC ATT GTC CTG GTC CTT GCC AAG AGG CAT CGT       1248
Ser Leu Thr Leu Ala Thr Ile Val Leu Val Leu Ala Lys Arg His Arg
            400                 405                 410

ACT GCT TCC CAC CCT GTG ATA TGC CCT GCA TCT GTC TCC CAA TAAAAGAATA   1300
Thr Ala Ser His Pro Val Ile Cys Pro Ala Ser Val Ser Gln
        415                 420                 425

AGCAAAAAAA AAAAAACCGG AATTC                                          1325
```

(2) INFORMATION FOR SEQ ID NO:12:

(i) SEQUENCE CHARACTERISTICS:
        (A) LENGTH: 426 amino acids
        (B) TYPE: amino acid
        (D) TOPOLOGY: linear (ii) MOLECULE TYPE: protein (xi) SEQUENCE DESCRIPTION: SEQ ID NO:12:

```
Met Gly Leu Ser Tyr Gly Ile Phe Ile Cys Phe Leu Leu Leu Gly Gly
 1               5                  10                  15
```

```
Met Glu Leu Cys Cys Pro Gln Thr Ile Trp Pro Thr Glu Thr Tyr Tyr
            20                  25                  30

Pro Leu Thr Ser Arg Pro Pro Val Met Val Asp Cys Leu Glu Ser Gln
            35                  40                  45

Leu Val Val Thr Val Ser Lys Asp Leu Phe Gly Thr Gly Lys Leu Ile
        50                  55                  60

Arg Pro Ala Asp Leu Thr Leu Gly Pro Glu Asn Cys Glu Pro Leu Val
 65                  70                  75                  80

Ser Met Asp Thr Asp Asp Val Val Arg Phe Glu Val Gly Leu His Glu
                85                  90                  95

Cys Gly Ser Arg Val Gln Val Thr Asp Asn Ala Leu Val Tyr Ser Thr
            100                 105                 110

Phe Leu Ile His Ser Pro Arg Pro Ala Gly Asn Leu Ser Ile Leu Arg
            115                 120                 125

Thr Asn Arg Ala Glu Val Pro Ile Glu Cys His Tyr Pro Arg His Ser
    130                 135                 140

Asn Val Ser Ser Gln Ala Ile Leu Pro Thr Trp Val Pro Phe Arg Thr
145                 150                 155                 160

Thr Met Leu Phe Glu Glu Lys Leu Val Phe Ser Leu Arg Leu Met Glu
                165                 170                 175

Glu Asp Trp Gly Ser Glu Lys Gln Ser Pro Thr Phe Gln Leu Gly Asp
            180                 185                 190

Ile Ala His Leu Gln Ala Glu Val His Thr Gly Ser His Met Pro Leu
            195                 200                 205

Arg Leu Phe Val Asp His Cys Val Ala Thr Leu Thr Pro Asp Arg Asn
    210                 215                 220

Ala Phe Leu His His Lys Ile Val Asp Phe His Gly Cys Leu Val Asp
225                 230                 235                 240

Gly Leu Tyr Asn Ser Ser Ala Phe Lys Ala Pro Arg Pro Arg Pro
                245                 250                 255

Glu Thr Leu Gln Phe Thr Val Asp Val Phe His Phe Ala Lys Asp Ser
            260                 265                 270

Arg Asn Thr Ile Tyr Ile Thr Cys His Leu Lys Val Thr Pro Ala Asp
    275                 280                 285

Arg Val Pro Asp Gln Leu Asn Lys Ala Cys Ser Phe Ile Lys Ser Thr
    290                 295                 300

Lys Arg Trp Tyr Pro Val Glu Gly Ser Ala Asp Ile Cys Arg Cys Cys
305                 310                 315                 320

Asn Lys Gly Ser Cys Gly Leu Pro Gly Arg Ser Arg Leu Ser His
                325                 330                 335

Leu Glu Arg Gly Trp Arg Lys Ser Val Ser His Thr Arg Asn Arg Arg
            340                 345                 350

His Val Thr Glu Glu Ala Glu Ile Thr Val Gly Pro Leu Ile Phe Leu
            355                 360                 365

Gly Lys Ala Ser Asp His Gly Ile Glu Gly Ser Thr Ser Pro His Thr
        370                 375                 380

Ser Val Met Leu Gly Leu Gly Leu Ala Thr Val Ser Leu Thr Leu
385                 390                 395                 400

Ala Thr Ile Val Leu Val Leu Ala Lys Arg His Arg Thr Ala Ser His
                405                 410                 415

Pro Val Ile Cys Pro Ala Ser Val Ser Gln
            420                 425
```

(2) INFORMATION FOR SEQ ID NO:13:

(i) SEQUENCE CHARACTERISTICS:
  (A) LENGTH: 2236 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (vi) ORIGINAL SOURCE:
  (A) ORGANISM: Felis domesticus
  (D) DEVELOPMENTAL STAGE: Juvenile
  (E) HAPLOTYPE: Diploidy
  (F) TISSUE TYPE: Ovary
  (G) CELL TYPE: Oocyte (ix) FEATURE:
  (A) NAME/KEY: CDS
  (B) LOCATION: 28..2175

(xi) SEQUENCE DESCRIPTION: SEQ ID NO:13:

```
GAATTCGCGG CCGCGATACT TTTGGCT ATG GCC TCC AGA CAG AAA GGA GAT           51
                              Met Ala Ser Arg Gln Lys Gly Asp
                                1               5

AGT GGG AGT CCT TCA AGC TGG TTT AAT GCA GAT TGG AGC ACC TAC AGG         99
Ser Gly Ser Pro Ser Ser Trp Phe Asn Ala Asp Trp Ser Thr Tyr Arg
        10                  15                  20

TCA CTT TTT CTA CTC TTT ATC CTC GTG ACT TCA GTG AAT TCC ATA GGT         147
Ser Leu Phe Leu Leu Phe Ile Leu Val Thr Ser Val Asn Ser Ile Gly
 25                  30                  35                  40

GTT TTG CAG TTG GTG AAT CCT GTC TTC CCA GGT ACT GTC ACT TGC TAT         195
Val Leu Gln Leu Val Asn Pro Val Phe Pro Gly Thr Val Thr Cys Tyr
                 45                  50                  55

GAA ACT AGA ATG GCA GTG GAA TTT CCA AGT GAT TTT GGC ACC AAA AAA         243
Glu Thr Arg Met Ala Val Glu Phe Pro Ser Asp Phe Gly Thr Lys Lys
                     60                  65                  70

TGG CAT ACA TCT GTG GTG GAT CCC TTT AGT TTT GAA TTG TTG AAC TGC         291
Trp His Thr Ser Val Val Asp Pro Phe Ser Phe Glu Leu Leu Asn Cys
             75                  80                  85

ACT TAC ATC TTG GAT CCA GAA AAT CTC ACC TTA AAG GCC CCA TAT GAG         339
Thr Tyr Ile Leu Asp Pro Glu Asn Leu Thr Leu Lys Ala Pro Tyr Glu
         90                  95                  100

ACC TGT ACC AGA AGA ACG CTT GGC CAG CAC CGG ATG ATC ATC AGA CTC         387
Thr Cys Thr Arg Arg Thr Leu Gly Gln His Arg Met Ile Ile Arg Leu
105                 110                 115                 120

AAG GAC CAC AAT GCT GCT TCA AGA CAT AAC AGT TTG ATG TAT CAG ATC         435
Lys Asp His Asn Ala Ala Ser Arg His Asn Ser Leu Met Tyr Gln Ile
                125                 130                 135

AAC TGT CCA GTT ATG CAA GCA GAA GAA ACC CAT GAG CAT GCA GGA TCC         483
Asn Cys Pro Val Met Gln Ala Glu Glu Thr His Glu His Ala Gly Ser
            140                 145                 150

ACT ATC TGC ACA AAG GAT TCC ATG TCT TTT ACC TTT AAT GTC ATT CCT         531
Thr Ile Cys Thr Lys Asp Ser Met Ser Phe Thr Phe Asn Val Ile Pro
        155                 160                 165

GGC CTG GCT GAT GAA AAT ACG GAT ATC AAG AAT CCG ATG GGA TGG AGC         579
Gly Leu Ala Asp Glu Asn Thr Asp Ile Lys Asn Pro Met Gly Trp Ser
    170                 175                 180

ATT GAG GTT GGT GAT GGT ACA AAA GCC AAA ACT CTG ACT CTT CAG GAT         627
Ile Glu Val Gly Asp Gly Thr Lys Ala Lys Thr Leu Thr Leu Gln Asp
185                 190                 195                 200

GTC TTG AGA CAA GGA TAC AAT ATC CTG TTT GAT AAC CAC AAG ATC ACC         675
```

-continued

| | | | | | | | | | | | | | | | | |
|---|---|---|---|---|---|---|---|---|---|---|---|---|---|---|---|---|
| | Val | Leu | Arg | Gln | Gly | Tyr | Asn | Ile | Leu | Phe | Asp | Asn | His | Lys | Ile | Thr |
| | | | | 205 | | | | | 210 | | | | | 215 | | |
| TTC | CAG | GTG | TCA | TTC | AAT | GCC | ACT | GGA | GTG | ACT | CAC | TAC | ATG | CAA | GGT | 723 |
| Phe | Gln | Val | Ser | Phe | Asn | Ala | Thr | Gly | Val | Thr | His | Tyr | Met | Gln | Gly | |
| | | | 220 | | | | | 225 | | | | | 230 | | | |
| AAC | AGT | CAC | CTC | TAC | ATG | GTG | CCT | CTG | AAG | TTG | ATA | CAT | GAA | TCT | CTT | 771 |
| Asn | Ser | His | Leu | Tyr | Met | Val | Pro | Leu | Lys | Leu | Ile | His | Glu | Ser | Leu | |
| | | 235 | | | | | 240 | | | | | 245 | | | | |
| GGG | CAG | AAG | ATC | ATC | TTA | ACA | ACA | CGA | GTG | CTT | TGT | ATG | TCA | GAT | GCT | 819 |
| Gly | Gln | Lys | Ile | Ile | Leu | Thr | Thr | Arg | Val | Leu | Cys | Met | Ser | Asp | Ala | |
| | 250 | | | | | 255 | | | | | 260 | | | | | |
| GTG | ACC | TGT | AAT | GCC | ACA | CAT | GTG | ACT | CTG | ACC | ATA | CCA | GAG | TTT | CCT | 867 |
| Val | Thr | Cys | Asn | Ala | Thr | His | Val | Thr | Leu | Thr | Ile | Pro | Glu | Phe | Pro | |
| 265 | | | | | 270 | | | | | 275 | | | | | 280 | |
| GGG | AAG | TTA | AAA | TCT | GTG | AGC | TCT | GAA | AAT | AGG | AAC | TTT | GCT | GTA | AGC | 915 |
| Gly | Lys | Leu | Lys | Ser | Val | Ser | Ser | Glu | Asn | Arg | Asn | Phe | Ala | Val | Ser | |
| | | | | 285 | | | | | 290 | | | | | 295 | | |
| CAG | CTG | CAC | AAC | AAT | GGG | ATT | GAT | AAA | GAA | GAA | TCA | AGT | GGC | TTG | ACA | 963 |
| Gln | Leu | His | Asn | Asn | Gly | Ile | Asp | Lys | Glu | Glu | Ser | Ser | Gly | Leu | Thr | |
| | | | 300 | | | | | 305 | | | | | 310 | | | |
| TTG | CAC | TTC | AGC | AAA | ACT | CTT | CTC | AAA | ATG | GAA | TTC | TCT | GAA | AAA | TGC | 1011 |
| Leu | His | Phe | Ser | Lys | Thr | Leu | Leu | Lys | Met | Glu | Phe | Ser | Glu | Lys | Cys | |
| | | 315 | | | | | 320 | | | | | 325 | | | | |
| CTA | CCC | TAT | CAG | TTC | TAC | TTA | GCT | TCA | CTC | AAG | CTG | ACC | TTT | GCC | TTT | 1059 |
| Leu | Pro | Tyr | Gln | Phe | Tyr | Leu | Ala | Ser | Leu | Lys | Leu | Thr | Phe | Ala | Phe | |
| | 330 | | | | | 335 | | | | | 340 | | | | | |
| AAT | CAA | GAG | ACT | ATA | TCC | ACG | GTG | CTT | TAT | CCT | GAG | TGT | GTC | TGT | GAG | 1107 |
| Asn | Gln | Glu | Thr | Ile | Ser | Thr | Val | Leu | Tyr | Pro | Glu | Cys | Val | Cys | Glu | |
| 345 | | | | | 350 | | | | | 355 | | | | | 360 | |
| TCA | CCA | GTT | TCT | ATA | GTT | ACA | GGT | GAC | CTG | TGT | ACT | CAG | GAT | GGG | TTT | 1155 |
| Ser | Pro | Val | Ser | Ile | Val | Thr | Gly | Asp | Leu | Cys | Thr | Gln | Asp | Gly | Phe | |
| | | | | 365 | | | | | 370 | | | | | 375 | | |
| ATG | GAC | ATA | AAG | GTC | TAC | AGT | CAC | CAG | ACA | AAA | CCA | GCT | CTC | AAC | TTA | 1203 |
| Met | Asp | Ile | Lys | Val | Tyr | Ser | His | Gln | Thr | Lys | Pro | Ala | Leu | Asn | Leu | |
| | | | 380 | | | | | 385 | | | | | 390 | | | |
| GAA | ACC | CTA | AGG | GTG | GGA | GAC | TCA | TCC | TGC | CAA | CCT | ACC | TTC | CAG | GCT | 1251 |
| Glu | Thr | Leu | Arg | Val | Gly | Asp | Ser | Ser | Cys | Gln | Pro | Thr | Phe | Gln | Ala | |
| | | 395 | | | | | 400 | | | | | 405 | | | | |
| GCA | TCT | CAA | GGG | CTG | ATA | CTG | TTT | CAC | ATA | CCC | CTG | AAT | GGA | TGC | GGG | 1299 |
| Ala | Ser | Gln | Gly | Leu | Ile | Leu | Phe | His | Ile | Pro | Leu | Asn | Gly | Cys | Gly | |
| | 410 | | | | | 415 | | | | | 420 | | | | | |
| ACA | AGA | CAT | AAG | TTC | AAG | GAA | GGC | AAA | GTC | ATC | TAT | GAA | AAT | GAA | ATA | 1347 |
| Thr | Arg | His | Lys | Phe | Lys | Glu | Gly | Lys | Val | Ile | Tyr | Glu | Asn | Glu | Ile | |
| 425 | | | | | 430 | | | | | 435 | | | | | 440 | |
| CAT | GCT | GTC | TGG | GCG | GAT | CTT | CCT | CCA | AGC | ACA | ATT | TCT | AGA | GAT | AGT | 1395 |
| His | Ala | Val | Trp | Ala | Asp | Leu | Pro | Pro | Ser | Thr | Ile | Ser | Arg | Asp | Ser | |
| | | | 445 | | | | | 450 | | | | | 455 | | | |
| GAA | TTC | AGA | ATG | ACA | GTG | CAG | TGC | CAT | TAC | AGC | AAA | GGT | GAC | CTG | CTA | 1443 |
| Glu | Phe | Arg | Met | Thr | Val | Gln | Cys | His | Tyr | Ser | Lys | Gly | Asp | Leu | Leu | |
| | | 460 | | | | | 465 | | | | | 470 | | | | |
| ATA | AAT | ACC | AGA | GTC | CAA | AGT | CTT | CCT | CCT | CTA | GAG | GCC | TCA | GTG | AGG | 1491 |
| Ile | Asn | Thr | Arg | Val | Gln | Ser | Leu | Pro | Pro | Leu | Glu | Ala | Ser | Val | Arg | |
| | 475 | | | | | 480 | | | | | 485 | | | | | |
| CCA | GGT | CCA | CTT | GCC | TTA | ATC | CTG | CAA | ACC | TAC | CCA | GAT | AAA | TCC | TAC | 1539 |
| Pro | Gly | Pro | Leu | Ala | Leu | Ile | Leu | Gln | Thr | Tyr | Pro | Asp | Lys | Ser | Tyr | |
| | 490 | | | | | 495 | | | | | 500 | | | | | |
| CTC | CAA | CCT | TAC | GGG | GAG | AAG | GAG | TAC | CCT | GTG | GTG | AGA | TAC | CTC | CGC | 1587 |
| Leu | Gln | Pro | Tyr | Gly | Glu | Lys | Glu | Tyr | Pro | Val | Val | Arg | Tyr | Leu | Arg | |
| 505 | | | | | 510 | | | | | 515 | | | | | 520 | |
| CAA | CCA | ATT | TAT | CTG | GAA | GTG | AGA | GTC | CTA | AAT | AGG | TCT | GAC | CCC | AAC | 1635 |
| Gln | Pro | Ile | Tyr | Leu | Glu | Val | Arg | Val | Leu | Asn | Arg | Ser | Asp | Pro | Asn | |

-continued

```
Gln Pro Ile Tyr Leu Glu Val Arg Val Leu Asn Arg Ser Asp Pro Asn
            525                 530                 535

ATC AAG CTG GTC TTA GAT GAC TGC TGG GCA ACA CCC ACG ATG GAC CCA       1683
Ile Lys Leu Val Leu Asp Asp Cys Trp Ala Thr Pro Thr Met Asp Pro
        540                 545                 550

GCC TCC GTC CCC CAG TGG AAT ATT ATC ATG GAT GGC TGT GAA TAC AAC       1731
Ala Ser Val Pro Gln Trp Asn Ile Ile Met Asp Gly Cys Glu Tyr Asn
            555                 560                 565

CTG GAC AAC CAC AGA ACC ACC TTC CAT CCA GTT GGC TCC TCT GTG ACC       1779
Leu Asp Asn His Arg Thr Thr Phe His Pro Val Gly Ser Ser Val Thr
        570                 575                 580

TAT CCT ACT CAC TAT CGG AGG TTT GAT GTG AAG ACC TTT GCC TTT GTA       1827
Tyr Pro Thr His Tyr Arg Arg Phe Asp Val Lys Thr Phe Ala Phe Val
585                 590                 595                 600

TCA GAG GCC CAA GTG CTT TCT AGT CTG GTC TAC TTC CAC TGC AGT GTC       1875
Ser Glu Ala Gln Val Leu Ser Ser Leu Val Tyr Phe His Cys Ser Val
            605                 610                 615

TTA ATC TGC AGT CGA CTG TCT GCT GAC TCC CCT CTG TGT TCC GTG ACT       1923
Leu Ile Cys Ser Arg Leu Ser Ala Asp Ser Pro Leu Cys Ser Val Thr
        620                 625                 630

TGC CCT GTG TCA TTC AGA CAC AGG AGA GCC ACA GGC ACC ACT GAA GAA       1971
Cys Pro Val Ser Phe Arg His Arg Arg Ala Thr Gly Thr Thr Glu Glu
            635                 640                 645

GAG AAA ATG ATA GTG AGT CTT CCA GGA CCC ATC CTC CTG CTG TCA GAT       2019
Glu Lys Met Ile Val Ser Leu Pro Gly Pro Ile Leu Leu Leu Ser Asp
        650                 655                 660

AGC TCT TCA CTC AGA GAT GTG GTG GAC TCA AAA GGG TAT GGG GCT GCC       2067
Ser Ser Ser Leu Arg Asp Val Val Asp Ser Lys Gly Tyr Gly Ala Ala
665                 670                 675                 680

GGA TAT GTT GCT TTT AAG ACT GTG GTA GCT GTG GCT GCC TTA GCA GGC       2115
Gly Tyr Val Ala Phe Lys Thr Val Val Ala Val Ala Ala Leu Ala Gly
            685                 690                 695

CTC GTG GCA ACG CTA GGC TTC ATC ACC TAC CTG CGC AAG AAC AGA ACC       2163
Leu Val Ala Thr Leu Gly Phe Ile Thr Tyr Leu Arg Lys Asn Arg Thr
        700                 705                 710

ATG ATA AAT CAC TAAGGATTTT CAAATAAAAT GGTTGAAGTA AAAAAAAAA           2215
Met Ile Asn His
        715

AAAAAAAGCG GCCGCGAATT C                                                2236
```

(2) INFORMATION FOR SEQ ID NO:14:

(i) SEQUENCE CHARACTERISTICS:
        (A) LENGTH: 716 amino acids
        (B) TYPE: amino acid
        (D) TOPOLOGY: linear (ii) MOLECULE TYPE: protein (xi) SEQUENCE DESCRIPTION: SEQ ID NO:14:

```
Met Ala Ser Arg Gln Lys Gly Asp Ser Gly Ser Pro Ser Ser Trp Phe
1               5                   10                  15

Asn Ala Asp Trp Ser Thr Tyr Arg Ser Leu Phe Leu Leu Phe Ile Leu
            20                  25                  30

Val Thr Ser Val Asn Ser Ile Gly Val Leu Gln Leu Val Asn Pro Val
        35                  40                  45

Phe Pro Gly Thr Val Thr Cys Tyr Glu Thr Arg Met Ala Val Glu Phe
    50                  55                  60

Pro Ser Asp Phe Gly Thr Lys Lys Trp His Thr Ser Val Val Asp Pro
65                  70                  75                  80
```

-continued

```
Phe Ser Phe Glu Leu Leu Asn Cys Thr Tyr Ile Leu Asp Pro Glu Asn
                 85                  90                  95

Leu Thr Leu Lys Ala Pro Tyr Glu Thr Cys Thr Arg Arg Thr Leu Gly
            100                 105                 110

Gln His Arg Met Ile Ile Arg Leu Lys Asp His Asn Ala Ala Ser Arg
            115                 120                 125

His Asn Ser Leu Met Tyr Gln Ile Asn Cys Pro Val Met Gln Ala Glu
            130                 135                 140

Glu Thr His Glu His Ala Gly Ser Thr Ile Cys Thr Lys Asp Ser Met
145                 150                 155                 160

Ser Phe Thr Phe Asn Val Ile Pro Gly Leu Ala Asp Glu Asn Thr Asp
                165                 170                 175

Ile Lys Asn Pro Met Gly Trp Ser Ile Glu Val Gly Asp Gly Thr Lys
                180                 185                 190

Ala Lys Thr Leu Thr Leu Gln Asp Val Leu Arg Gln Gly Tyr Asn Ile
            195                 200                 205

Leu Phe Asp Asn His Lys Ile Thr Phe Gln Val Ser Phe Asn Ala Thr
    210                 215                 220

Gly Val Thr His Tyr Met Gln Gly Asn Ser His Leu Tyr Met Val Pro
225                 230                 235                 240

Leu Lys Leu Ile His Glu Ser Leu Gly Gln Lys Ile Ile Leu Thr Thr
                245                 250                 255

Arg Val Leu Cys Met Ser Asp Ala Val Thr Cys Asn Ala Thr His Val
            260                 265                 270

Thr Leu Thr Ile Pro Glu Phe Pro Gly Lys Leu Lys Ser Val Ser Ser
    275                 280                 285

Glu Asn Arg Asn Phe Ala Val Ser Gln Leu His Asn Asn Gly Ile Asp
    290                 295                 300

Lys Glu Glu Ser Ser Gly Leu Thr Leu His Phe Ser Lys Thr Leu Leu
305                 310                 315                 320

Lys Met Glu Phe Ser Glu Lys Cys Leu Pro Tyr Gln Phe Tyr Leu Ala
                325                 330                 335

Ser Leu Lys Leu Thr Phe Ala Phe Asn Gln Glu Thr Ile Ser Thr Val
            340                 345                 350

Leu Tyr Pro Glu Cys Val Cys Glu Ser Pro Val Ser Ile Val Thr Gly
            355                 360                 365

Asp Leu Cys Thr Gln Asp Gly Phe Met Asp Ile Lys Val Tyr Ser His
    370                 375                 380

Gln Thr Lys Pro Ala Leu Asn Leu Glu Thr Leu Arg Val Gly Asp Ser
385                 390                 395                 400

Ser Cys Gln Pro Thr Phe Gln Ala Ala Ser Gln Gly Leu Ile Leu Phe
                405                 410                 415

His Ile Pro Leu Asn Gly Cys Gly Thr Arg His Lys Phe Lys Glu Gly
            420                 425                 430

Lys Val Ile Tyr Glu Asn Glu Ile His Ala Val Trp Ala Asp Leu Pro
            435                 440                 445

Pro Ser Thr Ile Ser Arg Asp Ser Glu Phe Arg Met Thr Val Gln Cys
    450                 455                 460

His Tyr Ser Lys Gly Asp Leu Leu Ile Asn Thr Arg Val Gln Ser Leu
465                 470                 475                 480

Pro Pro Leu Glu Ala Ser Val Arg Pro Gly Pro Leu Ala Leu Ile Leu
                485                 490                 495

Gln Thr Tyr Pro Asp Lys Ser Tyr Leu Gln Pro Tyr Gly Glu Lys Glu
            500                 505                 510
```

```
Tyr Pro Val Val Arg Tyr Leu Arg Gln Pro Ile Tyr Leu Glu Val Arg
            515                 520                 525

Val Leu Asn Arg Ser Asp Pro Asn Ile Lys Leu Val Leu Asp Asp Cys
530                 535                 540

Trp Ala Thr Pro Thr Met Asp Pro Ala Ser Val Pro Gln Trp Asn Ile
545                 550                 555                 560

Ile Met Asp Gly Cys Glu Tyr Asn Leu Asp Asn His Arg Thr Thr Phe
                565                 570                 575

His Pro Val Gly Ser Ser Val Thr Tyr Pro Thr His Tyr Arg Arg Phe
            580                 585                 590

Asp Val Lys Thr Phe Ala Phe Val Ser Glu Ala Gln Val Leu Ser Ser
        595                 600                 605

Leu Val Tyr Phe His Cys Ser Val Leu Ile Cys Ser Arg Leu Ser Ala
    610                 615                 620

Asp Ser Pro Leu Cys Ser Val Thr Cys Pro Val Ser Phe Arg His Arg
625                 630                 635                 640

Arg Ala Thr Gly Thr Thr Glu Glu Lys Met Ile Val Ser Leu Pro
                645                 650                 655

Gly Pro Ile Leu Leu Ser Asp Ser Ser Leu Arg Asp Val Val
                660                 665                 670

Asp Ser Lys Gly Tyr Gly Ala Ala Gly Tyr Val Ala Phe Lys Thr Val
            675                 680                 685

Val Ala Val Ala Ala Leu Ala Gly Leu Val Ala Thr Leu Gly Phe Ile
        690                 695                 700

Thr Tyr Leu Arg Lys Asn Arg Thr Met Ile Asn His
705                 710                 715
```

(2) INFORMATION FOR SEQ ID NO:15:

(i) SEQUENCE CHARACTERISTICS:
        (A) LENGTH: 1840 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Felis domesticus
        (D) DEVELOPMENTAL STAGE: Juvenile
        (E) HAPLOTYPE: Diploidy
        (F) TISSUE TYPE: Ovary
        (G) CELL TYPE: Oocyte (ix) FEATURE:
        (A) NAME/KEY: CDS
        (B) LOCATION: 57..1766

(xi) SEQUENCE DESCRIPTION: SEQ ID NO:15:

```
GAATTCCGCG GCCGCAAGTA CAGGTCTTGC AGCCAGTGGG GGCTCCCGAT GGCATC        56

ATG TGG CTG CTG CAG CCC CTC TTG CTC TGT GTT CCC TTG TCT CTC GCT     104
Met Trp Leu Leu Gln Pro Leu Leu Leu Cys Val Pro Leu Ser Leu Ala
 1               5                  10                  15

GTG CAT GGC CAG CAG AAG CCC CAG GTA CCA GAT TAT CCC GGT GAA CTC     152
Val His Gly Gln Gln Lys Pro Gln Val Pro Asp Tyr Pro Gly Glu Leu
                20                  25                  30

CAT TGT GGG CTC CAG AGC CTT CAG TTT GCC ATA AAC CCG AGC CCC GGG     200
His Cys Gly Leu Gln Ser Leu Gln Phe Ala Ile Asn Pro Ser Pro Gly
```

```
                35                    40                    45
AAA GCG ACT CCT GCA CTC ATA GTC TGG GAC AAT CGC GGG CTG CCA CAC       248
Lys Ala Thr Pro Ala Leu Ile Val Trp Asp Asn Arg Gly Leu Pro His
         50                  55                  60

AAG CTG CAG AAC AAC TCT GGC TGC GGT ACC TGG GTA AGG GAG AGC CCG       296
Lys Leu Gln Asn Asn Ser Gly Cys Gly Thr Trp Val Arg Glu Ser Pro
65                  70                  75                  80

GGG GGC TCC GTG CTG TTA GAC GCC TCT TAC AGC AGC TGC TAT GTC AAC       344
Gly Gly Ser Val Leu Leu Asp Ala Ser Tyr Ser Ser Cys Tyr Val Asn
                    85                  90                  95

GAG TGG GTG AGC ACG ACC CAA TCC CCA GGA ACG TCG AGG CCC CCC ACC       392
Glu Trp Val Ser Thr Thr Gln Ser Pro Gly Thr Ser Arg Pro Pro Thr
                100                 105                 110

CCA GCA TCC AGG GTG ACT CCC CAG GAC TCC CAC TAC GTC ATG ATA GTC       440
Pro Ala Ser Arg Val Thr Pro Gln Asp Ser His Tyr Val Met Ile Val
            115                 120                 125

GGA GTT GAA GGC ACA GAT GCG GCT GGG CGC AGG GTT ACC AAC ACC AAG       488
Gly Val Glu Gly Thr Asp Ala Ala Gly Arg Arg Val Thr Asn Thr Lys
        130                 135                 140

GTG CTC AGG TGT CCT AGG AAT CCC CCA GAC CAA GCT TTG GTG TCG AGC       536
Val Leu Arg Cys Pro Arg Asn Pro Pro Asp Gln Ala Leu Val Ser Ser
145                 150                 155                 160

TTA AGT CCC TCT CCT CTT CAA AAC GTA GCA CTA GAA GCT CCA AAC GCT       584
Leu Ser Pro Ser Pro Leu Gln Asn Val Ala Leu Glu Ala Pro Asn Ala
                165                 170                 175

GAC TTG TGT GAC TCT GTC CCA AAG TGG GAC AGG CTT CCG TGT GCT TCT       632
Asp Leu Cys Asp Ser Val Pro Lys Trp Asp Arg Leu Pro Cys Ala Ser
                180                 185                 190

TCA CCC ATC ACT CAG GGA GAC TGC AAT AAG CTT GGT TGC TGC TAC AAA       680
Ser Pro Ile Thr Gln Gly Asp Cys Asn Lys Leu Gly Cys Cys Tyr Lys
            195                 200                 205

TCA GAG GCA AAT TCC TGT TAC TAT GGA AAC ACA GTG ACC TCA CGC TGT       728
Ser Glu Ala Asn Ser Cys Tyr Tyr Gly Asn Thr Val Thr Ser Arg Cys
        210                 215                 220

ACC CAA GAC GGC CAC TTC TCC ATC GCC GTG TCT CGG AAC GTG ACC TCA       776
Thr Gln Asp Gly His Phe Ser Ile Ala Val Ser Arg Asn Val Thr Ser
225                 230                 235                 240

CCC CCA CTG CTC TTA AAT TCT CTG CGC TTG GCC TTC GGG AAG GAC CGC       824
Pro Pro Leu Leu Leu Asn Ser Leu Arg Leu Ala Phe Gly Lys Asp Arg
                245                 250                 255

GAA TGT AAC CCT GTG AAA GCA ACA CGT GCC TTT GCC CTG TTC TTT TTT       872
Glu Cys Asn Pro Val Lys Ala Thr Arg Ala Phe Ala Leu Phe Phe Phe
                260                 265                 270

CCA TTT AAT TCC TGT GGC ACC ACG AGA TGG GTC ACT GGA GAC CAG GCA       920
Pro Phe Asn Ser Cys Gly Thr Thr Arg Trp Val Thr Gly Asp Gln Ala
            275                 280                 285

GTA TAT GAA AAT GAG CTG GTG GCA GCT AGA GAT GTG AGA ACT TGG AGC       968
Val Tyr Glu Asn Glu Leu Val Ala Ala Arg Asp Val Arg Thr Trp Ser
        290                 295                 300

CAT GGT TCT ATT ACC CGT GAC AGT ATC TTC AGG CTT CGA GTT AGC TGC      1016
His Gly Ser Ile Thr Arg Asp Ser Ile Phe Arg Leu Arg Val Ser Cys
305                 310                 315                 320

AGC TAC TCT GTA AGG AGT AAT GCC TTC CCG CTT AGC GTT CAG GTG TTT      1064
Ser Tyr Ser Val Arg Ser Asn Ala Phe Pro Leu Ser Val Gln Val Phe
                325                 330                 335

ACC ATC CCA CCA CCC CAT CTG AAA ACC CAG CAT GGA CCC CTC ACT CTG      1112
Thr Ile Pro Pro Pro His Leu Lys Thr Gln His Gly Pro Leu Thr Leu
                340                 345                 350

GAA CTC AAG ATT GCC AAA GAT AAG CAC TAT GGC TCC TAC TAC ACT ATT      1160
Glu Leu Lys Ile Ala Lys Asp Lys His Tyr Gly Ser Tyr Tyr Thr Ile
```

```
              355                 360                 365
GGT GAC TAC CCA GTG GTA AAG TTG CTT CGG GAT CCC ATT TAT GTG GAG    1208
Gly Asp Tyr Pro Val Val Lys Leu Leu Arg Asp Pro Ile Tyr Val Glu
    370                 375                 380

GTC TCT ATC CGC CAC AGA ACG GAC CCC TCC CTG GGG CTG CTC CTC CAT    1256
Val Ser Ile Arg His Arg Thr Asp Pro Ser Leu Gly Leu Leu Leu His
385                 390                 395                 400

AAC TGT TGG GCC ACA CCC GGC AAG AAC TCC CAG AGT CTG TCC CAG TGG    1304
Asn Cys Trp Ala Thr Pro Gly Lys Asn Ser Gln Ser Leu Ser Gln Trp
                405                 410                 415

CCC ATT CTG GTG AAA GGA TGC CCC TAC GTT GGA GAC AAC TAT CAA ACC    1352
Pro Ile Leu Val Lys Gly Cys Pro Tyr Val Gly Asp Asn Tyr Gln Thr
            420                 425                 430

CAG CTG ATC CCT GTC CAG AAG GCT CTG GAT ACA CCA TTT CCA TCT TAC    1400
Gln Leu Ile Pro Val Gln Lys Ala Leu Asp Thr Pro Phe Pro Ser Tyr
            435                 440                 445

TAC AAG CGC TTC AGT ATT TTC ACC TTC AGC TTT GTG GAC ACC ATG GCA    1448
Tyr Lys Arg Phe Ser Ile Phe Thr Phe Ser Phe Val Asp Thr Met Ala
    450                 455                 460

AAG TGG GCA CTC AGG GGA CCG GTG TAT CTG CAC TGT AAT GTA TCC ATC    1496
Lys Trp Ala Leu Arg Gly Pro Val Tyr Leu His Cys Asn Val Ser Ile
465                 470                 475                 480

TGC CAG CCT GCT GGG ACC TCC TCC TGT AGG ATA ACC TGT CCT GTT GCC    1544
Cys Gln Pro Ala Gly Thr Ser Ser Cys Arg Ile Thr Cys Pro Val Ala
                485                 490                 495

AGG CGA AGA AGA CAC TCT GAC CTC CAT CAT CAC AGC AGT ACT GCG AGC    1592
Arg Arg Arg Arg His Ser Asp Leu His His His Ser Ser Thr Ala Ser
                500                 505                 510

ATC TCT AGC AAG GGT CCC ATG ATT CTA CTC CAA GCC ACT ATG GAC TCT    1640
Ile Ser Ser Lys Gly Pro Met Ile Leu Leu Gln Ala Thr Met Asp Ser
            515                 520                 525

GCA GAG AAG CTC CAC AAA AAC TCA AGT TCT CCT ATA GAC TCC CAA GCT    1688
Ala Glu Lys Leu His Lys Asn Ser Ser Ser Pro Ile Asp Ser Gln Ala
            530                 535                 540

CTG TGG ATG GCA GGC CTT TCC GGG ACC CTA ATC TTT GGA TTC TTG TTA    1736
Leu Trp Met Ala Gly Leu Ser Gly Thr Leu Ile Phe Gly Phe Leu Leu
545                 550                 555                 560

GTG TCC TAC TTG GCT ATC AGG AAA CGG AGG TGAATTATTC CAGTTGTGTT      1786
Val Ser Tyr Leu Ala Ile Arg Lys Arg Arg
                565                 570

AATAAAACCA GATTGCATTA CCAAAAAAAA AAAAAAAAAA GCGGCCGCGA ATTC        1840

(2) INFORMATION FOR SEQ ID NO:16:

(i) SEQUENCE CHARACTERISTICS:
        (A) LENGTH: 570 amino acids
        (B) TYPE: amino acid
        (D) TOPOLOGY: linear (ii) MOLECULE TYPE: protein (xi) SEQUENCE DESCRIPTION: SEQ ID NO:16:

Met Trp Leu Leu Gln Pro Leu Leu Leu Cys Val Pro Leu Ser Leu Ala
  1               5                  10                  15

Val His Gly Gln Gln Lys Pro Gln Val Pro Asp Tyr Pro Gly Glu Leu
                 20                  25                  30

His Cys Gly Leu Gln Ser Leu Gln Phe Ala Ile Asn Pro Ser Pro Gly
             35                  40                  45

Lys Ala Thr Pro Ala Leu Ile Val Trp Asp Asn Arg Gly Leu Pro His
         50                  55                  60
```

-continued

```
Lys Leu Gln Asn Asn Ser Gly Cys Gly Thr Trp Val Arg Glu Ser Pro
 65                  70                  75                  80

Gly Gly Ser Val Leu Leu Asp Ala Ser Tyr Ser Ser Cys Tyr Val Asn
             85                  90                  95

Glu Trp Val Ser Thr Thr Gln Ser Pro Gly Thr Ser Arg Pro Pro Thr
            100                 105                 110

Pro Ala Ser Arg Val Thr Pro Gln Asp Ser His Tyr Val Met Ile Val
            115                 120                 125

Gly Val Glu Gly Thr Asp Ala Ala Gly Arg Arg Val Thr Asn Thr Lys
        130                 135                 140

Val Leu Arg Cys Pro Arg Asn Pro Pro Asp Gln Ala Leu Val Ser Ser
145                 150                 155                 160

Leu Ser Pro Ser Pro Leu Gln Asn Val Ala Leu Glu Ala Pro Asn Ala
                165                 170                 175

Asp Leu Cys Asp Ser Val Pro Lys Trp Asp Arg Leu Pro Cys Ala Ser
            180                 185                 190

Ser Pro Ile Thr Gln Gly Asp Cys Asn Lys Leu Gly Cys Cys Tyr Lys
            195                 200                 205

Ser Glu Ala Asn Ser Cys Tyr Tyr Gly Asn Thr Val Thr Ser Arg Cys
        210                 215                 220

Thr Gln Asp Gly His Phe Ser Ile Ala Val Ser Arg Asn Val Thr Ser
225                 230                 235                 240

Pro Pro Leu Leu Leu Asn Ser Leu Arg Leu Ala Phe Gly Lys Asp Arg
                245                 250                 255

Glu Cys Asn Pro Val Lys Ala Thr Arg Ala Phe Ala Leu Phe Phe Phe
            260                 265                 270

Pro Phe Asn Ser Cys Gly Thr Thr Arg Trp Val Thr Gly Asp Gln Ala
            275                 280                 285

Val Tyr Glu Asn Glu Leu Val Ala Ala Arg Asp Val Arg Thr Trp Ser
        290                 295                 300

His Gly Ser Ile Thr Arg Asp Ser Ile Phe Arg Leu Arg Val Ser Cys
305                 310                 315                 320

Ser Tyr Ser Val Arg Ser Asn Ala Phe Pro Leu Ser Val Gln Val Phe
                325                 330                 335

Thr Ile Pro Pro Pro His Leu Lys Thr Gln His Gly Pro Leu Thr Leu
            340                 345                 350

Glu Leu Lys Ile Ala Lys Asp Lys His Tyr Gly Ser Tyr Tyr Thr Ile
            355                 360                 365

Gly Asp Tyr Pro Val Val Lys Leu Leu Arg Asp Pro Ile Tyr Val Glu
        370                 375                 380

Val Ser Ile Arg His Arg Thr Asp Pro Ser Leu Gly Leu Leu Leu His
385                 390                 395                 400

Asn Cys Trp Ala Thr Pro Gly Lys Asn Ser Gln Ser Leu Ser Gln Trp
                405                 410                 415

Pro Ile Leu Val Lys Gly Cys Pro Tyr Val Gly Asp Asn Tyr Gln Thr
            420                 425                 430

Gln Leu Ile Pro Val Gln Lys Ala Leu Asp Thr Pro Phe Pro Ser Tyr
            435                 440                 445

Tyr Lys Arg Phe Ser Ile Phe Thr Phe Ser Phe Val Asp Thr Met Ala
        450                 455                 460

Lys Trp Ala Leu Arg Gly Pro Val Tyr Leu His Cys Asn Val Ser Ile
465                 470                 475                 480

Cys Gln Pro Ala Gly Thr Ser Ser Cys Arg Ile Thr Cys Pro Val Ala
                485                 490                 495
```

```
Arg Arg Arg Arg His Ser Asp Leu His His Ser Ser Thr Ala Ser
            500             505             510

Ile Ser Ser Lys Gly Pro Met Ile Leu Leu Gln Ala Thr Met Asp Ser
        515             520             525

Ala Glu Lys Leu His Lys Asn Ser Ser Ser Pro Ile Asp Ser Gln Ala
        530             535             540

Leu Trp Met Ala Gly Leu Ser Gly Thr Leu Ile Phe Gly Phe Leu Leu
545             550             555             560

Val Ser Tyr Leu Ala Ile Arg Lys Arg Arg
            565             570
```

(2) INFORMATION FOR SEQ ID NO:17:

(i) SEQUENCE CHARACTERISTICS:
        (A) LENGTH: 1319 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Felis domesticus
        (D) DEVELOPMENTAL STAGE: Juvenile
        (E) HAPLOTYPE: Diploidy
        (F) TISSUE TYPE: Ovary
        (G) CELL TYPE: Oocyte (ix) FEATURE:
        (A) NAME/KEY: CDS
        (B) LOCATION: 26..1297

(xi) SEQUENCE DESCRIPTION: SEQ ID NO:17:

```
GAATTCGCGG CCGCGCGTAG GCCGC ATG GGG CTG AGC TAC GGG CTT TTC ATC        52
                            Met Gly Leu Ser Tyr Gly Leu Phe Ile
                             1               5

TGT TTT CTG CTT TGG GCA GGC ACG GGG CTG TGC TAT CCC CCA ACC ACC       100
Cys Phe Leu Leu Trp Ala Gly Thr Gly Leu Cys Tyr Pro Pro Thr Thr
 10              15                  20                  25

ACC GAG GAT AAG ACC CAC CCC TCG TTG CCA TCA AGC CCC TCT GTG GTG       148
Thr Glu Asp Lys Thr His Pro Ser Leu Pro Ser Ser Pro Ser Val Val
             30                  35                  40

GTA GAG TGT CGG CAT GCC TGG CTG GTG GTC AAC GTC AGC AAA AAC CTT       196
Val Glu Cys Arg His Ala Trp Leu Val Val Asn Val Ser Lys Asn Leu
         45                  50                  55

TTT GGT ACT GGG AGG CTT GTG AGG CCT GCA GAC CTC ACC CTG GGT CCG       244
Phe Gly Thr Gly Arg Leu Val Arg Pro Ala Asp Leu Thr Leu Gly Pro
     60                  65                  70

GAG AAC TGT GAG CCC CTG ATC TCT GGG GAC TCA GAT GAT ACG GTC AGG       292
Glu Asn Cys Glu Pro Leu Ile Ser Gly Asp Ser Asp Asp Thr Val Arg
 75                  80                  85

TTT GAA GTC GAG CTC CAC AAG TGT GGC AAC AGC GTG CAG GTG ACC GAA       340
Phe Glu Val Glu Leu His Lys Cys Gly Asn Ser Val Gln Val Thr Glu
 90                  95                 100                 105

GAT GCC CTG GTG TAT AGC ACC TTC CTG CTC CAC AAC CCC CGC CCC ATG       388
Asp Ala Leu Val Tyr Ser Thr Phe Leu Leu His Asn Pro Arg Pro Met
             110                 115                 120

GGA AAC CTG TCC ATC CTG AGG ACC AAC CGC GCG GAA GTT CCC ATT GAG       436
Gly Asn Leu Ser Ile Leu Arg Thr Asn Arg Ala Glu Val Pro Ile Glu
         125                 130                 135
```

```
TGC CGT TAC CCC AGG CAT AGC AAC GTG AGC AGC GAG GCC ATC CTG CCC      484
Cys Arg Tyr Pro Arg His Ser Asn Val Ser Ser Glu Ala Ile Leu Pro
    140                 145                 150

ACC TGG GTG CCC TTC AGG ACC ACA ATG CTC TCA GAG GAG AAG CTG GCT      532
Thr Trp Val Pro Phe Arg Thr Thr Met Leu Ser Glu Glu Lys Leu Ala
155                 160                 165

TTC TCT CTG CGC CTG ATG GAG GAG GAC TGG GGC TCC GAG AAG CAG TCC      580
Phe Ser Leu Arg Leu Met Glu Glu Asp Trp Gly Ser Glu Lys Gln Ser
170                 175                 180                 185

CCC ACT TTC CAG TTG GGA GAC CTA GCC CAC CTC CAG GCC GAA GTC CAC      628
Pro Thr Phe Gln Leu Gly Asp Leu Ala His Leu Gln Ala Glu Val His
            190                 195                 200

ACC GGC CGC CAC ATA CCA CTG CGA CTG TTT GTG GAC TAC TGT GTG GCC      676
Thr Gly Arg His Ile Pro Leu Arg Leu Phe Val Asp Tyr Cys Val Ala
            205                 210                 215

ACG CTG ACA CCA GAC CAG AAC GCC TCC CCT CAT CAC ACC ATC GTG GAC      724
Thr Leu Thr Pro Asp Gln Asn Ala Ser Pro His His Thr Ile Val Asp
            220                 225                 230

TTC CAC GGC TGT CTC GTG GAT GGT CTC TCT GAT GCC TCT TCT GCC TTC      772
Phe His Gly Cys Leu Val Asp Gly Leu Ser Asp Ala Ser Ser Ala Phe
            235                 240                 245

AAA GCC CCC AGA CCC AGG CCG GAG ACT CTC CAG TTT ACA GTA GAC ACG      820
Lys Ala Pro Arg Pro Arg Pro Glu Thr Leu Gln Phe Thr Val Asp Thr
250                 255                 260                 265

TTC CAC TTT GCT AAT GAC CCC AGA AAC ATG ATC TAT ATC ACC TGC CAT      868
Phe His Phe Ala Asn Asp Pro Arg Asn Met Ile Tyr Ile Thr Cys His
            270                 275                 280

CTG AAA GTC ACT CCA GCT AGC CGA GTC CCA GAC CAG CTA AAC AAA GCC      916
Leu Lys Val Thr Pro Ala Ser Arg Val Pro Asp Gln Leu Asn Lys Ala
            285                 290                 295

TGT TCC TTC ATC AAG TCT TCT AAC AGG TGG TTC CCA GTA GAA GGC CCT      964
Cys Ser Phe Ile Lys Ser Ser Asn Arg Trp Phe Pro Val Glu Gly Pro
            300                 305                 310

GCT GAC ATC TGT AAC TGT TGT AAC AAA GGT AGC TGT GGC CTT CAG GGC      1012
Ala Asp Ile Cys Asn Cys Cys Asn Lys Gly Ser Cys Gly Leu Gln Gly
315                 320                 325

CGT TCC TGG AGG CTG TCC CAC CTA GAC AGA CCG TGG CAC AAG ATG GCT      1060
Arg Ser Trp Arg Leu Ser His Leu Asp Arg Pro Trp His Lys Met Ala
330                 335                 340                 345

TCC CGA AAT CGC AGG CAT GTG ACC GAA GAA GCG GAT ATC ACC GTG GGG      1108
Ser Arg Asn Arg Arg His Val Thr Glu Glu Ala Asp Ile Thr Val Gly
            350                 355                 360

CCT CTG ATC TTC CTG GGA AAG GCT GCC GAT CGT GGT GTG GAG GGG TCG      1156
Pro Leu Ile Phe Leu Gly Lys Ala Ala Asp Arg Gly Val Glu Gly Ser
            365                 370                 375

ACC TCG CCT CAC ACC TCT GTG ATG GTG GGC ATA GGC CTG GCC ACG GTG      1204
Thr Ser Pro His Thr Ser Val Met Val Gly Ile Gly Leu Ala Thr Val
            380                 385                 390

TTG TCC CTG ACT CTG GCT ACC ATT GTC CTG GGT CTC GCC AGG AGG CAT      1252
Leu Ser Leu Thr Leu Ala Thr Ile Val Leu Gly Leu Ala Arg Arg His
395                 400                 405

CAC ACT GCT TCC CGT CCT ATG ATC TGC CCT GTG TCT GCT TCC CAA          1297
His Thr Ala Ser Arg Pro Met Ile Cys Pro Val Ser Ala Ser Gln
410                 415                 420

TAAAAGAAGC GGCCGCGAAT TC                                             1319
```

(2) INFORMATION FOR SEQ ID NO:18:

(i) SEQUENCE CHARACTERISTICS:
        (A) LENGTH: 424 amino acids
        (B) TYPE: amino acid (D) TOPOLOGY: linear (ii) MOLECULE TYPE: protein (xi) SEQUENCE DESCRIPTION: SEQ ID NO:18:

```
Met Gly Leu Ser Tyr Gly Leu Phe Ile Cys Phe Leu Trp Ala Gly
  1               5                  10                  15

Thr Gly Leu Cys Tyr Pro Pro Thr Thr Thr Glu Asp Lys Thr His Pro
                 20                  25                  30

Ser Leu Pro Ser Ser Pro Ser Val Val Glu Cys Arg His Ala Trp
             35                  40                  45

Leu Val Val Asn Val Ser Lys Asn Leu Phe Gly Thr Gly Arg Leu Val
         50                  55                  60

Arg Pro Ala Asp Leu Thr Leu Gly Pro Glu Asn Cys Glu Pro Leu Ile
 65                  70                  75                  80

Ser Gly Asp Ser Asp Asp Thr Val Arg Phe Glu Val Glu Leu His Lys
                 85                  90                  95

Cys Gly Asn Ser Val Gln Val Thr Glu Asp Ala Leu Val Tyr Ser Thr
                100                 105                 110

Phe Leu Leu His Asn Pro Arg Pro Met Gly Asn Leu Ser Ile Leu Arg
            115                 120                 125

Thr Asn Arg Ala Glu Val Pro Ile Glu Cys Arg Tyr Pro Arg His Ser
130                 135                 140

Asn Val Ser Ser Glu Ala Ile Leu Pro Thr Trp Val Pro Phe Arg Thr
145                 150                 155                 160

Thr Met Leu Ser Glu Glu Lys Leu Ala Phe Ser Leu Arg Leu Met Glu
                165                 170                 175

Glu Asp Trp Gly Ser Glu Lys Gln Ser Pro Thr Phe Gln Leu Gly Asp
            180                 185                 190

Leu Ala His Leu Gln Ala Glu Val His Thr Gly Arg His Ile Pro Leu
            195                 200                 205

Arg Leu Phe Val Asp Tyr Cys Val Ala Thr Leu Thr Pro Asp Gln Asn
210                 215                 220

Ala Ser Pro His His Thr Ile Val Asp Phe His Gly Cys Leu Val Asp
225                 230                 235                 240

Gly Leu Ser Asp Ala Ser Ser Ala Phe Lys Ala Pro Arg Pro Arg Pro
                245                 250                 255

Glu Thr Leu Gln Phe Thr Val Asp Thr Phe His Phe Ala Asn Asp Pro
            260                 265                 270

Arg Asn Met Ile Tyr Ile Thr Cys His Leu Lys Val Thr Pro Ala Ser
            275                 280                 285

Arg Val Pro Asp Gln Leu Asn Lys Ala Cys Ser Phe Ile Lys Ser Ser
    290                 295                 300

Asn Arg Trp Phe Pro Val Glu Gly Pro Ala Asp Ile Cys Asn Cys Cys
305                 310                 315                 320

Asn Lys Gly Ser Cys Gly Leu Gln Gly Arg Ser Trp Arg Leu Ser His
                325                 330                 335

Leu Asp Arg Pro Trp His Lys Met Ala Ser Arg Asn Arg Arg His Val
            340                 345                 350

Thr Glu Glu Ala Asp Ile Thr Val Gly Pro Leu Ile Phe Leu Gly Lys
            355                 360                 365

Ala Ala Asp Arg Gly Val Glu Gly Ser Thr Ser Pro His Thr Ser Val
        370                 375                 380

Met Val Gly Ile Gly Leu Ala Thr Val Leu Ser Leu Thr Leu Ala Thr
385                 390                 395                 400
```

Ile Val Leu Gly Leu Ala Arg Arg His His Thr Ala Ser Arg Pro Met
            405                 410                 415

Ile Cys Pro Val Ser Ala Ser Gln
            420

(2) INFORMATION FOR SEQ ID NO:19:

(i) SEQUENCE CHARACTERISTICS:
        (A) LENGTH: 643 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Bos taurus
        (D) DEVELOPMENTAL STAGE: Juvenile
        (E) HAPLOTYPE: Diploidy
        (F) TISSUE TYPE: Ovary
        (G) CELL TYPE: Oocyte (ix) FEATURE:
        (A) NAME/KEY: CDS
        (B) LOCATION: 16..582

(xi) SEQUENCE DESCRIPTION: SEQ ID NO:19:

```
GAATTCGCGG CCGCC CTA AAC AGG ACT GAC CCC AAC ATC AAG TTG GTC TTA       51
                Leu Asn Arg Thr Asp Pro Asn Ile Lys Leu Val Leu
                 1               5                  10

GAT GAT TGC TGG GCA ACA TCC ACC ATG GAC CCA GCC TCT CTC CCT CAG       99
Asp Asp Cys Trp Ala Thr Ser Thr Met Asp Pro Ala Ser Leu Pro Gln
         15                  20                  25

TGG AAT ATT ATC GTG GAT GGC TGT GAA TAC AAC TTG GAC AAC CAC AGA      147
Trp Asn Ile Ile Val Asp Gly Cys Glu Tyr Asn Leu Asp Asn His Arg
 30                  35                  40

ACC ACC TTC CAT CCG GTT GGC TCC TCG GTG GCC TAT CCT AAT CAC TAC      195
Thr Thr Phe His Pro Val Gly Ser Ser Val Ala Tyr Pro Asn His Tyr
 45                  50                  55                  60

CAG AGG TTT GCT GTG AAG ACC TTT GCC TTT GTG TCA GAG GAC CCG GCG      243
Gln Arg Phe Ala Val Lys Thr Phe Ala Phe Val Ser Glu Asp Pro Ala
                 65                  70                  75

TTC TCT CAC TTG GTC TAC TTC CAC TGC AGC GCC TTA ATC TGC GAT CAA      291
Phe Ser His Leu Val Tyr Phe His Cys Ser Ala Leu Ile Cys Asp Gln
                 80                  85                  90

CTT TCT TCT AAC TTC CCC CTG TGT TCT GCG TCT TGC CTT GTG TCA TCC      339
Leu Ser Ser Asn Phe Pro Leu Cys Ser Ala Ser Cys Leu Val Ser Ser
                 95                 100                 105

AGA AGC AGG CGA GCC ACA GGG GCC ACT GAG GAA GAG AAG ATG ATA GTG      387
Arg Ser Arg Arg Ala Thr Gly Ala Thr Glu Glu Glu Lys Met Ile Val
        110                 115                 120

AGT CTC CCG GGC CCC ATC CTC CTG TTG TCA GAT GGC TCT TCA TTC AGA      435
Ser Leu Pro Gly Pro Ile Leu Leu Leu Ser Asp Gly Ser Ser Phe Arg
125                 130                 135                 140

GAT GCT GTG GAT TCT AAA GGG CAT GGG ACT TCT GGA TAT GCT GCT TTT      483
Asp Ala Val Asp Ser Lys Gly His Gly Thr Ser Gly Tyr Ala Ala Phe
                145                 150                 155

AAA ACT ATG GTT GCT GTA GTT GCC TTA GCA GGT GTT GTG GCA ACT CTA      531
Lys Thr Met Val Ala Val Val Ala Leu Ala Gly Val Val Ala Thr Leu
            160                 165                 170

AGC CTA ATC AGC TAC CTG CGC AAG AAA AGA ATC ACA GTG CTA AAC CAC      579
```

Ser Leu Ile Ser Tyr Leu Arg Lys Lys Arg Ile Thr Val Leu Asn His
175                 180                 185

TAATTGGATT TTCAATAAAA TGTGGAAGTA AAAAAAAAAA AAAAAAAAAA GCGGCCGCGA    639

ATTC    643

(2) INFORMATION FOR SEQ ID NO:20:

(i) SEQUENCE CHARACTERISTICS:
        (A) LENGTH: 188 amino acids
        (B) TYPE: amino acid
        (D) TOPOLOGY: linear (ii) MOLECULE TYPE: protein (xi) SEQUENCE DESCRIPTION: SEQ ID NO:20:

Leu Asn Arg Thr Asp Pro Asn Ile Lys Leu Val Leu Asp Asp Cys Trp
 1               5                  10                  15

Ala Thr Ser Thr Met Asp Pro Ala Ser Leu Pro Gln Trp Asn Ile Ile
             20                  25                  30

Val Asp Gly Cys Glu Tyr Asn Leu Asp Asn His Arg Thr Thr Phe His
         35                  40                  45

Pro Val Gly Ser Ser Val Ala Tyr Pro Asn His Tyr Gln Arg Phe Ala
     50                  55                  60

Val Lys Thr Phe Ala Phe Val Ser Glu Asp Pro Ala Phe Ser His Leu
 65                  70                  75                  80

Val Tyr Phe His Cys Ser Ala Leu Ile Cys Asp Gln Leu Ser Ser Asn
                 85                  90                  95

Phe Pro Leu Cys Ser Ala Ser Cys Leu Val Ser Ser Arg Ser Arg Arg
                100                 105                 110

Ala Thr Gly Ala Thr Glu Glu Glu Lys Met Ile Val Ser Leu Pro Gly
            115                 120                 125

Pro Ile Leu Leu Leu Ser Asp Gly Ser Ser Phe Arg Asp Ala Val Asp
        130                 135                 140

Ser Lys Gly His Gly Thr Ser Gly Tyr Ala Ala Phe Lys Thr Met Val
145                 150                 155                 160

Ala Val Val Ala Leu Ala Gly Val Val Ala Thr Leu Ser Leu Ile Ser
                165                 170                 175

Tyr Leu Arg Lys Lys Arg Ile Thr Val Leu Asn His
                180                 185

(2) INFORMATION FOR SEQ ID NO:21:

(i) SEQUENCE CHARACTERISTICS:
        (A) LENGTH: 1029 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Bos taurus
        (D) DEVELOPMENTAL STAGE: Juvenile
        (E) HAPLOTYPE: Diploidy
        (F) TISSUE TYPE: Ovary
        (G) CELL TYPE: Oocyte (ix) FEATURE:
        (A) NAME/KEY: CDS
        (B) LOCATION: 2..976

(xi) SEQUENCE DESCRIPTION: SEQ ID NO:21:

```
G AAT TCT GTA CAC TTG GCC TTC AGG AAT GAC AGC GAA TGT AAA CCT        46
  Asn Ser Val His Leu Ala Phe Arg Asn Asp Ser Glu Cys Lys Pro
  1               5                  10                  15

GTG ATG GCA ACA CAC ACT TTT GTT CTG TTC CGG TTT CCA TTT ACT ACT      94
Val Met Ala Thr His Thr Phe Val Leu Phe Arg Phe Pro Phe Thr Thr
                 20                  25                  30

TGT GGT ACT ACA AAA CAG ATC ACT GGA AAG CAA GCG GTA TAT GAA AAT     142
Cys Gly Thr Thr Lys Gln Ile Thr Gly Lys Gln Ala Val Tyr Glu Asn
             35                  40                  45

GAG CTG GTT GCA GCT CGG GAT GTG AGA ACT TGG AGC CGT GGT TCT ATT     190
Glu Leu Val Ala Ala Arg Asp Val Arg Thr Trp Ser Arg Gly Ser Ile
         50                  55                  60

ACC CGA GAC AGT ACC TTC AGG CTC CAA GTC AGT TGT AGC TAC TCT GCA     238
Thr Arg Asp Ser Thr Phe Arg Leu Gln Val Ser Cys Ser Tyr Ser Ala
     65                  70                  75

AGT AGC AGT GCT CTC CCA GTT AAT GTC CAA GTT CTT ACT CTC CCA CCA     286
Ser Ser Ser Ala Leu Pro Val Asn Val Gln Val Leu Thr Leu Pro Pro
 80                  85                  90                  95

CCC CTT CCT GAG ACC CTG CCT GGA AAC CTC ACT CTG GAA CTT AAG ATT     334
Pro Leu Pro Glu Thr Leu Pro Gly Asn Leu Thr Leu Glu Leu Lys Ile
                100                 105                 110

GCC AAA GAT AAA CCG TAT CGC TCC TAC TAC ACG GCT AGT GAC TAC CCA     382
Ala Lys Asp Lys Pro Tyr Arg Ser Tyr Tyr Thr Ala Ser Asp Tyr Pro
            115                 120                 125

GTG GTG AAG TTA CTT CGG GAT CCC ATC TAC GTG GAA GTC TCC ATC CAT     430
Val Val Lys Leu Leu Arg Asp Pro Ile Tyr Val Glu Val Ser Ile His
        130                 135                 140

CAG AGA ACA GAC CCC AGT CTC GAG CTG CGC CTG GAC CAG TGT TGG GCG     478
Gln Arg Thr Asp Pro Ser Leu Glu Leu Arg Leu Asp Gln Cys Trp Ala
    145                 150                 155

ACA CCT GGT GCA GAT GCC CTG CTC CAG CCC CAG TGG CCC TTG CTT GTG     526
Thr Pro Gly Ala Asp Ala Leu Leu Gln Pro Gln Trp Pro Leu Leu Val
160                 165                 170                 175

AAT GGG TGC CCC TAC ACA GGA GAC AAC TAT CAG ACA AAA CTG ATC CCT     574
Asn Gly Cys Pro Tyr Thr Gly Asp Asn Tyr Gln Thr Lys Leu Ile Pro
                180                 185                 190

GTC TGG GAA GCC TCA GAC CTG CCG TTT CCT TCT CAC TAC CAG CGC TTC     622
Val Trp Glu Ala Ser Asp Leu Pro Phe Pro Ser His Tyr Gln Arg Phe
            195                 200                 205

AGC ATT TCC ACC TTC AGC TTT GTG GAC TCA GTG GCA AAG CGG GCC CTC     670
Ser Ile Ser Thr Phe Ser Phe Val Asp Ser Val Ala Lys Arg Ala Leu
        210                 215                 220

AAG GGA CCG GTG TAT CTG CAC TGC AGT GCA TCG GTC TGC CAG CCT GCC     718
Lys Gly Pro Val Tyr Leu His Cys Ser Ala Ser Val Cys Gln Pro Ala
    225                 230                 235

GGG ACA CCA TCC TGT GTG ACA CTC TGT CCT GCC AGA CGA AGA AGA AGC     766
Gly Thr Pro Ser Cys Val Thr Leu Cys Pro Ala Arg Arg Arg Arg Ser
240                 245                 250                 255

TCT GAC ATC CAT TTT CAG AAC AAA ACG GCT AGC ATT TCT AGC AAG GGT     814
Ser Asp Ile His Phe Gln Asn Lys Thr Ala Ser Ile Ser Ser Lys Gly
                260                 265                 270

CCC TTG ATT CTA CTC CAA GCC ATT CAA GAC TCT TCA GAA AAG CTC CAC     862
Pro Leu Ile Leu Leu Gln Ala Ile Gln Asp Ser Ser Glu Lys Leu His
            275                 280                 285

AAA TAC TCA AGG TCT CCT GTA GAC TCT CAA GCT TTG TGG GTG GCT GGC     910
Lys Tyr Ser Arg Ser Pro Val Asp Ser Gln Ala Leu Trp Val Ala Gly
        290                 295                 300

CTA TCT GGA ATC TTA ATC GTT GGA GCC TTG TTC ATG TCC TAC CTG GCC     958
```

```
         Leu Ser Gly Ile Leu Ile Val Gly Ala Leu Phe Met Ser Tyr Leu Ala
             305                 310                 315

ATT AGG AAA TGG AGA TGAGTTGCTC AGCCCAAATG TGTTAATAAA ACCAGATTGC           1013
Ile Arg Lys Trp Arg
320

AGCCGGCCGC GAATTC                                                         1029
```

(2) INFORMATION FOR SEQ ID NO:22:

(i) SEQUENCE CHARACTERISTICS:
        (A) LENGTH: 324 amino acids
        (B) TYPE: amino acid
        (D) TOPOLOGY: linear (ii) MOLECULE TYPE: protein (xi) SEQUENCE DESCRIPTION: SEQ ID NO:22:

```
Asn Ser Val His Leu Ala Phe Arg Asn Asp Ser Glu Cys Lys Pro Val
 1               5                  10                  15

Met Ala Thr His Thr Phe Val Leu Phe Arg Phe Pro Phe Thr Thr Cys
                20                  25                  30

Gly Thr Thr Lys Gln Ile Thr Gly Lys Gln Ala Val Tyr Glu Asn Glu
             35                  40                  45

Leu Val Ala Ala Arg Asp Val Arg Thr Trp Ser Arg Gly Ser Ile Thr
 50                  55                  60

Arg Asp Ser Thr Phe Arg Leu Gln Val Ser Cys Ser Tyr Ser Ala Ser
 65                  70                  75                  80

Ser Ser Ala Leu Pro Val Asn Val Gln Val Leu Thr Leu Pro Pro Pro
                 85                  90                  95

Leu Pro Glu Thr Leu Pro Gly Asn Leu Thr Leu Glu Leu Lys Ile Ala
                100                 105                 110

Lys Asp Lys Pro Tyr Arg Ser Tyr Tyr Thr Ala Ser Asp Tyr Pro Val
                115                 120                 125

Val Lys Leu Leu Arg Asp Pro Ile Tyr Val Glu Val Ser Ile His Gln
130                 135                 140

Arg Thr Asp Pro Ser Leu Glu Leu Arg Leu Asp Gln Cys Trp Ala Thr
145                 150                 155                 160

Pro Gly Ala Asp Ala Leu Leu Gln Pro Gln Trp Pro Leu Leu Val Asn
                165                 170                 175

Gly Cys Pro Tyr Thr Gly Asp Asn Tyr Gln Thr Lys Leu Ile Pro Val
                180                 185                 190

Trp Glu Ala Ser Asp Leu Pro Phe Pro Ser His Tyr Gln Arg Phe Ser
                195                 200                 205

Ile Ser Thr Phe Ser Phe Val Asp Ser Val Ala Lys Arg Ala Leu Lys
            210                 215                 220

Gly Pro Val Tyr Leu His Cys Ser Ala Ser Val Cys Gln Pro Ala Gly
225                 230                 235                 240

Thr Pro Ser Cys Val Thr Leu Cys Pro Ala Arg Arg Arg Arg Ser Ser
                245                 250                 255

Asp Ile His Phe Gln Asn Lys Thr Ala Ser Ile Ser Ser Lys Gly Pro
                260                 265                 270

Leu Ile Leu Leu Gln Ala Ile Gln Asp Ser Ser Glu Lys Leu His Lys
            275                 280                 285

Tyr Ser Arg Ser Pro Val Asp Ser Gln Ala Leu Trp Val Ala Gly Leu
            290                 295                 300

Ser Gly Ile Leu Ile Val Gly Ala Leu Phe Met Ser Tyr Leu Ala Ile
305                 310                 315                 320
```

Arg Lys Trp Arg (2) INFORMATION FOR SEQ ID NO:23:

(i) SEQUENCE CHARACTERISTICS:
        (A) LENGTH: 1457 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Bos taurus
        (D) DEVELOPMENTAL STAGE: Juvenile
        (E) HAPLOTYPE: Diploidy
        (F) TISSUE TYPE: Ovary
        (G) CELL TYPE: Oocyte (ix) FEATURE:
        (A) NAME/KEY: CDS
        (B) LOCATION: 149..1411

(xi) SEQUENCE DESCRIPTION: SEQ ID NO:23:

```
CCCGGGCCTC CCTACTCTCA GGAAGGCACC CGCTCACCTC CTCAAGTTCT CGATCTCGGC        60

CGGGATGCTC TGAAGCTGGT TGCCGCCGAG GCTGAGGGTC TGCAGCGGCG CAGTCCAGCA       120

GCGAGGTGGG AGTGGCTTCG TGGGCACC ATG GGG CCG TGC TCT AGG CTG TTC         172
                              Met Gly Pro Cys Ser Arg Leu Phe
                                1               5

GTC TGC TTT CTG CTC TGG GGA AGC ACA GAG CTC TGC AGC CCC CAG CCC        220
Val Cys Phe Leu Leu Trp Gly Ser Thr Glu Leu Cys Ser Pro Gln Pro
 10              15                  20

TTC TGG GAT GAT GAA ACC GAG CGC TTC AGG CCA TCA AAG CCG CCC GCC        268
Phe Trp Asp Asp Glu Thr Glu Arg Phe Arg Pro Ser Lys Pro Pro Ala
 25              30                  35                  40

GTG ATG GTG GAG TGT CAG GAG GCC CAG CTG GTG GTC ACA GTC GAC AAA        316
Val Met Val Glu Cys Gln Glu Ala Gln Leu Val Val Thr Val Asp Lys
                 45                  50                  55

GAC CTT TTC GGC ACA GGG AAG CTC ATC CGG CCT GCG GAC CTC ACC CTG        364
Asp Leu Phe Gly Thr Gly Lys Leu Ile Arg Pro Ala Asp Leu Thr Leu
             60                  65                  70

GGC CCC GAC AAC TGT GAG CCG CTG GCC TCC GCG GAC ACG GAT GGC GTG        412
Gly Pro Asp Asn Cys Glu Pro Leu Ala Ser Ala Asp Thr Asp Gly Val
         75                  80                  85

GTT AGG TTT GCG GTC GGG CTG CAC GAG TGT GGC AAC ATC TTG CAG GTG        460
Val Arg Phe Ala Val Gly Leu His Glu Cys Gly Asn Ile Leu Gln Val
 90                  95                  100

ACC GAC AAT GCC CTG GTG TAC AGC ACC TTC CTG CTC CAC AAC CCC CGC        508
Thr Asp Asn Ala Leu Val Tyr Ser Thr Phe Leu Leu His Asn Pro Arg
105                 110                 115                 120

CCT GCA GGA AAC CTG TCC ATC CTG AGG ACT AAC CGC GCA GAG GTC CCC        556
Pro Ala Gly Asn Leu Ser Ile Leu Arg Thr Asn Arg Ala Glu Val Pro
                125                 130                 135

ATC GAG TGC CAC TAC CCC AGG CAG GGC AAT GTG AGT AGC TGG GCC ATC        604
Ile Glu Cys His Tyr Pro Arg Gln Gly Asn Val Ser Ser Trp Ala Ile
                140                 145                 150

CAG CCC ACC TGG GTG CCA TTC AGG ACC ACA GTG TTC TCG GAG GAG AAG        652
Gln Pro Thr Trp Val Pro Phe Arg Thr Thr Val Phe Ser Glu Glu Lys
            155                 160                 165

CTG GTT TTC TCT CTG CGC CTG ATG GAG GAG AAC TGG AGC GCC GAG AAG        700
```

```
                Leu Val Phe Ser Leu Arg Leu Met Glu Glu Asn Trp Ser Ala Glu Lys
                    170                 175                 180

ATG ACG CCC ACC TTC CAG CTG GGA GAC AGA GCC CAC CTC CAG GCC CAA              748
Met Thr Pro Thr Phe Gln Leu Gly Asp Arg Ala His Leu Gln Ala Gln
185                 190                 195                 200

GTG CAC ACT GGC AGC CAC GTG CCC CTG CGG CTG TTC GTG GAC CAC TGC              796
Val His Thr Gly Ser His Val Pro Leu Arg Leu Phe Val Asp His Cys
                    205                 210                 215

GTG GCC AGC CTG ACG CCA GAC TGG AGC ACC TCC CCT TAC CAC ACC ATC              844
Val Ala Ser Leu Thr Pro Asp Trp Ser Thr Ser Pro Tyr His Thr Ile
                220                 225                 230

GTG GAC TTC CAT GGT TGT CTC GTC GAT GGT CTC ACC GAT GCC TCC TCT              892
Val Asp Phe His Gly Cys Leu Val Asp Gly Leu Thr Asp Ala Ser Ser
                    235                 240                 245

GCT TTC AAA GCA CCC AGA CCC AGA CCG GAG ATC CTC CAG TTC ACA GTG              940
Ala Phe Lys Ala Pro Arg Pro Arg Pro Glu Ile Leu Gln Phe Thr Val
                250                 255                 260

GAT GTG TTC CGT TTT GCT AAT GAC TCC AGA AAC ATG ATA TAT ATC ACC              988
Asp Val Phe Arg Phe Ala Asn Asp Ser Arg Asn Met Ile Tyr Ile Thr
265                 270                 275                 280

TGC CAC CTG AAG GTC ACT CCG GTT GAC CGA GTC CCG GAC CAA CTA AAC             1036
Cys His Leu Lys Val Thr Pro Val Asp Arg Val Pro Asp Gln Leu Asn
                    285                 290                 295

AAA GCC TGT TCC TTC AGC AAG TCC TCC AAC AGG TGG TCC CCG GTT GAA             1084
Lys Ala Cys Ser Phe Ser Lys Ser Ser Asn Arg Trp Ser Pro Val Glu
                300                 305                 310

GGC CCC ACT GAC ATC TGT CGA TGC TGT AGC AAG GGG CGC TGT GGC ATT             1132
Gly Pro Thr Asp Ile Cys Arg Cys Cys Ser Lys Gly Arg Cys Gly Ile
                    315                 320                 325

TCA GGC CGT TCC ATG AGG CTG TCC CAC CGG GAG GGC AGG CCT GTT CCC             1180
Ser Gly Arg Ser Met Arg Leu Ser His Arg Glu Gly Arg Pro Val Pro
330                 335                 340

CGA AGT CGC AGG CAC GTG ACG GAG GAA GCA GAT GTC ACC GTG GGG CCG             1228
Arg Ser Arg Arg His Val Thr Glu Glu Ala Asp Val Thr Val Gly Pro
345                 350                 355                 360

TTG ATC TTC CTG AGG AAG ATG AAT GAC CGT GGC GTG GAA GGG CCC ACC             1276
Leu Ile Phe Leu Arg Lys Met Asn Asp Arg Gly Val Glu Gly Pro Thr
                    365                 370                 375

TCC TCT CCC CCT CTG GTG ATG CTG GGC TTA GGC CTG GCT ACT GTG ATG             1324
Ser Ser Pro Pro Leu Val Met Leu Gly Leu Gly Leu Ala Thr Val Met
                380                 385                 390

ACC TTG ACT CTG GCT GCC ATT GTC CTG GGT CTC ACT GGG AGG CTT CGG             1372
Thr Leu Thr Leu Ala Ala Ile Val Leu Gly Leu Thr Gly Arg Leu Arg
                    395                 400                 405

GCT GCT TCT CAC CCC GTG TGC CCT GTG TCT GCT TCC CAA TAAAAGAAGA              1421
Ala Ala Ser His Pro Val Cys Pro Val Ser Ala Ser Gln
                410                 415                 420

AAGTGAAAAA AAAAAAAAA AAGCGGCCGC GAATTC                                      1457

(2) INFORMATION FOR SEQ ID NO:24:

(i) SEQUENCE CHARACTERISTICS:
         (A) LENGTH: 421 amino acids
         (B) TYPE: amino acid
         (D) TOPOLOGY: linear (ii) MOLECULE TYPE: protein (xi) SEQUENCE DESCRIPTION: SEQ ID NO:24:

Met Gly Pro Cys Ser Arg Leu Phe Val Cys Phe Leu Leu Trp Gly Ser
 1               5                  10                  15
```

-continued

```
Thr Glu Leu Cys Ser Pro Gln Pro Phe Trp Asp Asp Glu Thr Glu Arg
         20                  25                  30

Phe Arg Pro Ser Lys Pro Pro Ala Val Met Val Glu Cys Gln Glu Ala
         35                  40                  45

Gln Leu Val Val Thr Val Asp Lys Asp Leu Phe Gly Thr Gly Lys Leu
 50                  55                  60

Ile Arg Pro Ala Asp Leu Thr Leu Gly Pro Asp Asn Cys Glu Pro Leu
 65                  70                  75                  80

Ala Ser Ala Asp Thr Asp Gly Val Val Arg Phe Ala Val Gly Leu His
             85                  90                  95

Glu Cys Gly Asn Ile Leu Gln Val Thr Asp Asn Ala Leu Val Tyr Ser
                100                 105                 110

Thr Phe Leu Leu His Asn Pro Arg Pro Ala Gly Asn Leu Ser Ile Leu
         115                 120                 125

Arg Thr Asn Arg Ala Glu Val Pro Ile Glu Cys His Tyr Pro Arg Gln
 130                 135                 140

Gly Asn Val Ser Ser Trp Ala Ile Gln Pro Thr Trp Val Pro Phe Arg
145                 150                 155                 160

Thr Thr Val Phe Ser Glu Glu Lys Leu Val Phe Ser Leu Arg Leu Met
             165                 170                 175

Glu Glu Asn Trp Ser Ala Glu Lys Met Thr Pro Thr Phe Gln Leu Gly
                180                 185                 190

Asp Arg Ala His Leu Gln Ala Gln Val His Thr Gly Ser His Val Pro
         195                 200                 205

Leu Arg Leu Phe Val Asp His Cys Val Ala Ser Leu Thr Pro Asp Trp
 210                 215                 220

Ser Thr Ser Pro Tyr His Thr Ile Val Asp Phe His Gly Cys Leu Val
225                 230                 235                 240

Asp Gly Leu Thr Asp Ala Ser Ser Ala Phe Lys Ala Pro Arg Pro Arg
             245                 250                 255

Pro Glu Ile Leu Gln Phe Thr Val Asp Val Phe Arg Phe Ala Asn Asp
                260                 265                 270

Ser Arg Asn Met Ile Tyr Ile Thr Cys His Leu Lys Val Thr Pro Val
         275                 280                 285

Asp Arg Val Pro Asp Gln Leu Asn Lys Ala Cys Ser Phe Ser Lys Ser
 290                 295                 300

Ser Asn Arg Trp Ser Pro Val Glu Gly Pro Thr Asp Ile Cys Arg Cys
305                 310                 315                 320

Cys Ser Lys Gly Arg Cys Gly Ile Ser Gly Arg Ser Met Arg Leu Ser
             325                 330                 335

His Arg Glu Gly Arg Pro Val Pro Arg Ser Arg His Val Thr Glu
                340                 345                 350

Glu Ala Asp Val Thr Val Gly Pro Leu Ile Phe Leu Arg Lys Met Asn
         355                 360                 365

Asp Arg Gly Val Glu Gly Pro Thr Ser Ser Pro Leu Val Met Leu
 370                 375                 380

Gly Leu Gly Leu Ala Thr Val Met Thr Leu Thr Leu Ala Ala Ile Val
385                 390                 395                 400

Leu Gly Leu Thr Gly Arg Leu Arg Ala Ala Ser His Pro Val Cys Pro
             405                 410                 415

Val Ser Ala Ser Gln
            420
```

(2) INFORMATION FOR SEQ ID NO:25:

(i) SEQUENCE CHARACTERISTICS:
            (A) LENGTH: 125 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:25:

AGTTCGTGCT TATCTGAACA TGTCTTGAGG GATTAGTATG TGTGCTCATT TGGGTTCTTT     60

CCGCTGTATG CTAGGCGTAT CTAGATGCAT TAGCTTGTTA ACACCTCATG TGGAGTAAAA    120

GATGT                                                                125

(2) INFORMATION FOR SEQ ID NO:26:

(i) SEQUENCE CHARACTERISTICS:
            (A) LENGTH: 111 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:26:

CAGGCGTAGG CGTGGACTGA AGTTCAAAGC CATGCGCCCG TTCTGATAGC ATACGTTTGA     60

AATGTCATTG TAGTTGCATG GCTGTATAAG CCAGTCTCAT AGATAAGGGA A             111

(2) INFORMATION FOR SEQ ID NO:27:

(i) SEQUENCE CHARACTERISTICS:
            (A) LENGTH: 96 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:27:

GCGGTCGGTC ATGTGATGCT GCGTATAGTA CGATTTTGAA TGCATTATGC GAAATTATTC     60

TAACGACCCG CGATATGGAG GTTGGATTAA GTTACA                               96

(2) INFORMATION FOR SEQ ID NO:28:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:28:

ATGGARAGRT GYCAMGARG                                                  19

(2) INFORMATION FOR SEQ ID NO:29:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:29:

GATCTAAGGA AGATCTATGG ATCC                                            24

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GATCTAAGGA GGTTGTATGG ATCC                                    24

(2) INFORMATION FOR SEQ ID NO:31:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GATCTATGAC CATGATTACG GATTCGCGTA GCCGTCGTCC TGCAGCGTCG CGACT          55

(2) INFORMATION FOR SEQ ID NO:32:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

GGGAAAACCC GGGCGTTACC CAACTTAATC GATTAGCAGC ACATCCCCCT TCGCCAG       57

(2) INFORMATION FOR SEQ ID NO:33:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

TTTTCCCAGT CGCGCTGCAG AACGACGGCT AGCGAATCCG TAATCATGGT CATA          54

(2) INFORMATION FOR SEQ ID NO:34:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

CTGGCCAAAG GGGATGTGG CTGCTAATCG ATTAAGTTGG GTAACGCCCG GG            52

(2) INFORMATION FOR SEQ ID NO:35:

(i) SEQUENCE CHARACTERISTICS:

(A) LENGTH: 220 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:35:

GATCTATGAC CATGATTACG GATTCGCTAG CCGTCGTTCT GCAGCGTCGC GACTGGGAAA      60

ATACTGGTAC TAATGCCTAA GCGATCGGCA GCAAGACGTC GGAGCGCTGAC CCTTTACCC    120

GGGCGTTACC CAACTTAATC GATTAGCAGC ACATCCCCCT TTCGCCAGTGG GCCCGCAAT    180

CCCTTGAATT AGCAAATCGT CGTGTAGGGG GAAAGCGGTC                          220

(2) INFORMATION FOR SEQ ID NO:36:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

GCGAAGCTTC CGACACCATC GAACGGCGC                                       29

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

GCGCACAATG TGCCTAATGA GTGAGCTAAC                                      30

(2) INFORMATION FOR SEQ ID NO:38:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CGCGGATCCG GACGAAGGCC AGCGCTTG                                        28

(2) INFORMATION FOR SEQ ID NO:39:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

GCGGTCGACT CATTAATGAT GATGATGATG ATGCGGGCTC GAGGTGGACC CTTCCACC       58

(2) INFORMATION FOR SEQ ID NO:40:

(i) SEQUENCE CHARACTERISTICS:
    (A) LENGTH: 1701 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..1698

(xi) SEQUENCE DESCRIPTION: SEQ ID NO:40:

```
ATG TGG CTG CTG CGG TGC GTT TTG CTG TGT GTT TCA TTA TCT CTT GCT           48
Met Trp Leu Leu Arg Cys Val Leu Leu Cys Val Ser Leu Ser Leu Ala
 1               5                  10                  15

GTG AGT GGC CAG CAT AAG CCT GAG GCA CCA GAT TAT TCC AGT GTG CTC           96
Val Ser Gly Gln His Lys Pro Glu Ala Pro Asp Tyr Ser Ser Val Leu
                20                  25                  30

CAC TGT GGG CCG TGG AGC TTC CAG TTT GCT GTA AAC CTC AAC CAG GAG          144
His Cys Gly Pro Trp Ser Phe Gln Phe Ala Val Asn Leu Asn Gln Glu
            35                  40                  45

GCA ACG TCT CCT CCT GTA CTA ATA GCT TGG GAC AAC CAA GGG CTG CTG          192
Ala Thr Ser Pro Pro Val Leu Ile Ala Trp Asp Asn Gln Gly Leu Leu
        50                  55                  60

CAC GAG CTG CAG AAT GAC TCC GAC TGT GGC ACC TGG ATA AGA AAA GGT          240
His Glu Leu Gln Asn Asp Ser Asp Cys Gly Thr Trp Ile Arg Lys Gly
 65                  70                  75                  80

CCA GGC AGC TCC GTG GTG TTG GAG GCA ACC TAT AGC AGC TGC TAT GTC          288
Pro Gly Ser Ser Val Val Leu Glu Ala Thr Tyr Ser Ser Cys Tyr Val
                85                  90                  95

ACT GAG TGG GTG AGT ATG ACC CAA TGG CCA GGG AGA CTG TGT GAA GCG          336
Thr Glu Trp Val Ser Met Thr Gln Trp Pro Gly Arg Leu Cys Glu Ala
                100                 105                 110

CCT CAT GCT ACC ATC CAG GCT GAC CCC CAA GGC CTG TCT CTC CAG GAC          384
Pro His Ala Thr Ile Gln Ala Asp Pro Gln Gly Leu Ser Leu Gln Asp
            115                 120                 125

TCC CAC TAC ATC ATG CCA GTT GGA GTT GAA GGA GCA GGC GCG GCT GAA          432
Ser His Tyr Ile Met Pro Val Gly Val Glu Gly Ala Gly Ala Ala Glu
        130                 135                 140

CAC AAG GTG GTT ACA GAG AGG AAG CTG CTC AAG TGT CCT ATG GAT CTT          480
His Lys Val Val Thr Glu Arg Lys Leu Leu Lys Cys Pro Met Asp Leu
145                 150                 155                 160

CTA GAT GCT CCA GAT ACT GAC TGG TGT GAC TCC ATC CCA GCA CGG GAC          528
Leu Asp Ala Pro Asp Thr Asp Trp Cys Asp Ser Ile Pro Ala Arg Asp
                165                 170                 175

AGA CTG CCA TGT GCA CCT TCA CCC ATC TCT CGA GGA GAC TGT GAA GGG          576
Arg Leu Pro Cys Ala Pro Ser Pro Ile Ser Arg Gly Asp Cys Glu Gly
                180                 185                 190

CTA GGC TGT TGT TAT AGC TCT GAA GAG GTG AAT TCC TGC TAC TAT GGA          624
Leu Gly Cys Cys Tyr Ser Ser Glu Glu Val Asn Ser Cys Tyr Tyr Gly
            195                 200                 205

AAC ACT GTG ACC TTG CAT TGT ACC CGA GAG GGC CAT TTC TCT ATT GCT          672
Asn Thr Val Thr Leu His Cys Thr Arg Glu Gly His Phe Ser Ile Ala
        210                 215                 220

GTG TCT CGG AAC GTG ACC TCG CCA CCA CTG CTC TTG GAT TCT GTG CGC          720
Val Ser Arg Asn Val Thr Ser Pro Pro Leu Leu Leu Asp Ser Val Arg
225                 230                 235                 240

TTG GCC CTT AGG AAT GAC AGT GCG TGT AAC CCT GTG ATG GCA ACA CAA          768
Leu Ala Leu Arg Asn Asp Ser Ala Cys Asn Pro Val Met Ala Thr Gln
                245                 250                 255

GCT TTT GTT CTG TTC CAG TTT CCA TTT ACT TCC TGT GGC ACC ACA AGA          816
Ala Phe Val Leu Phe Gln Phe Pro Phe Thr Ser Cys Gly Thr Thr Arg
```

|     |     |
| --- | --- |
| 260 | |
| 265 | |
| 270 | |

```
CAG ATC ACT GGA GAC CGA GCA GTA TAT GAA AAT GAA CTG GTG GCA ACT      864
Gln Ile Thr Gly Asp Arg Ala Val Tyr Glu Asn Glu Leu Val Ala Thr
        275                 280                 285

AGG GAT GTG AAA AAT GGG AGC CGT GGC TCT GTC ACT CGT GAC AGC ATC      912
Arg Asp Val Lys Asn Gly Ser Arg Gly Ser Val Thr Arg Asp Ser Ile
        290                 295                 300

TTC AGG CTC CAT GTC AGC TGC AGC TAC TCA GTA AGT AGC AAC TCT CTC      960
Phe Arg Leu His Val Ser Cys Ser Tyr Ser Val Ser Ser Asn Ser Leu
305                 310                 315                 320

CCA ATC AAT GTC CAG GTT TTC ACT CTC CCA CCA CCC TTT CCT GAG ACC     1008
Pro Ile Asn Val Gln Val Phe Thr Leu Pro Pro Pro Phe Pro Glu Thr
        325                 330                 335

CAG CCT GGA CCC CTC ACT CTG GAA CTT CAG ATT GCC AAA GAT AAA AAC     1056
Gln Pro Gly Pro Leu Thr Leu Glu Leu Gln Ile Ala Lys Asp Lys Asn
        340                 345                 350

TAT GGC TCT TAC TAC GGT GTT GGT GAC TAC CCA GTG GTG AAG TTG CTT     1104
Tyr Gly Ser Tyr Tyr Gly Val Gly Asp Tyr Pro Val Val Lys Leu Leu
        355                 360                 365

CGG GAT CCC ATT TAC GTG GAG GTC TCC ATC CTT CAC AGA ACA GAC CCC     1152
Arg Asp Pro Ile Tyr Val Glu Val Ser Ile Leu His Arg Thr Asp Pro
        370                 375                 380

TAC CTG GGG CTG CTC CTA CAA CAG TGT TGG GCA ACA CCC AGC ACT GAC     1200
Tyr Leu Gly Leu Leu Leu Gln Gln Cys Trp Ala Thr Pro Ser Thr Asp
385                 390                 395                 400

CCC CTG AGT CAG CCA CAG TGG CCC ATC CTG GTA AAG GGC TGC CCC TAC     1248
Pro Leu Ser Gln Pro Gln Trp Pro Ile Leu Val Lys Gly Cys Pro Tyr
        405                 410                 415

ATT GGA GAC AAC TAT CAG ACC CAG CTG ATC CCT GTC CAG AAA GCC TTG     1296
Ile Gly Asp Asn Tyr Gln Thr Gln Leu Ile Pro Val Gln Lys Ala Leu
        420                 425                 430

GAT CTT CCA TTT CCC TCT CAC CAC CAG CGC TTC AGC ATC TTC ACC TTC     1344
Asp Leu Pro Phe Pro Ser His His Gln Arg Phe Ser Ile Phe Thr Phe
        435                 440                 445

AGC TTT GTG AAC CCT ACA GTG GAG AAA CAG GCC CTC AGG GGA CCG GTG     1392
Ser Phe Val Asn Pro Thr Val Glu Lys Gln Ala Leu Arg Gly Pro Val
        450                 455                 460

CAT CTG CAC TGC AGC GTG TCA GTC TGC CAG CCT GCT GAG ACA CCA TCC     1440
His Leu His Cys Ser Val Ser Val Cys Gln Pro Ala Glu Thr Pro Ser
465                 470                 475                 480

TGT GTG GTG ACC TGT CCT GAT CTC AGT CGA AGA AGA AAT TTT GAC AAC     1488
Cys Val Val Thr Cys Pro Asp Leu Ser Arg Arg Arg Asn Phe Asp Asn
        485                 490                 495

AGT TCT CAG AAC ACT ACT GCT AGT GTT TCT AGC AAA GGC CCC ATG ATT     1536
Ser Ser Gln Asn Thr Thr Ala Ser Val Ser Ser Lys Gly Pro Met Ile
        500                 505                 510

CTA CTC CAA GCC ACT AAG GAC CCT CCA GAA AAG CTC CGT GTT CCT GTA     1584
Leu Leu Gln Ala Thr Lys Asp Pro Pro Glu Lys Leu Arg Val Pro Val
        515                 520                 525

GAC TCG AAA GTT CTG TGG GTG GCA GGC CTT TCT GGG ACC TTA ATC CTT     1632
Asp Ser Lys Val Leu Trp Val Ala Gly Leu Ser Gly Thr Leu Ile Leu
        530                 535                 540

GGA GCC TTG TTA GTA TCC TAC TTG GCT GTC AAG AAA CAG AAG AGT TGC     1680
Gly Ala Leu Leu Val Ser Tyr Leu Ala Val Lys Lys Gln Lys Ser Cys
545                 550                 555                 560

CCA GAC CAA ATG TGT CAA TAA                                         1701
Pro Asp Gln Met Cys Gln
        565
```

(2) INFORMATION FOR SEQ ID NO:41:

(i) SEQUENCE CHARACTERISTICS:
    (A) LENGTH: 566 amino acids
    (B) TYPE: amino acid
    (D) TOPOLOGY: linear (ii) MOLECULE TYPE: protein (xi) SEQUENCE DESCRIPTION: SEQ ID NO:41:

```
Met Trp Leu Leu Arg Cys Val Leu Leu Cys Val Ser Leu Ser Leu Ala
 1               5                  10                  15

Val Ser Gly Gln His Lys Pro Glu Ala Pro Asp Tyr Ser Ser Val Leu
             20                  25                  30

His Cys Gly Pro Trp Ser Phe Gln Phe Ala Val Asn Leu Asn Gln Glu
         35                  40                  45

Ala Thr Ser Pro Pro Val Leu Ile Ala Trp Asp Asn Gln Gly Leu Leu
     50                  55                  60

His Glu Leu Gln Asn Asp Ser Asp Cys Gly Thr Trp Ile Arg Lys Gly
 65                  70                  75                  80

Pro Gly Ser Ser Val Val Leu Glu Ala Thr Tyr Ser Ser Cys Tyr Val
                 85                  90                  95

Thr Glu Trp Val Ser Met Thr Gln Trp Pro Gly Arg Leu Cys Glu Ala
             100                 105                 110

Pro His Ala Thr Ile Gln Ala Asp Pro Gln Gly Leu Ser Leu Gln Asp
         115                 120                 125

Ser His Tyr Ile Met Pro Val Gly Val Glu Gly Ala Gly Ala Ala Glu
     130                 135                 140

His Lys Val Val Thr Glu Arg Lys Leu Leu Lys Cys Pro Met Asp Leu
145                 150                 155                 160

Leu Asp Ala Pro Asp Thr Asp Trp Cys Asp Ser Ile Pro Ala Arg Asp
                165                 170                 175

Arg Leu Pro Cys Ala Pro Ser Pro Ile Ser Arg Gly Asp Cys Glu Gly
            180                 185                 190

Leu Gly Cys Cys Tyr Ser Ser Glu Glu Val Asn Ser Cys Tyr Tyr Gly
        195                 200                 205

Asn Thr Val Thr Leu His Cys Thr Arg Glu Gly His Phe Ser Ile Ala
210                 215                 220

Val Ser Arg Asn Val Thr Ser Pro Pro Leu Leu Leu Asp Ser Val Arg
225                 230                 235                 240

Leu Ala Leu Arg Asn Asp Ser Ala Cys Asn Pro Val Met Ala Thr Gln
                245                 250                 255

Ala Phe Val Leu Phe Gln Phe Pro Phe Thr Ser Cys Gly Thr Thr Arg
            260                 265                 270

Gln Ile Thr Gly Asp Arg Ala Val Tyr Glu Asn Glu Leu Val Ala Thr
        275                 280                 285

Arg Asp Val Lys Asn Gly Ser Arg Gly Ser Val Thr Arg Asp Ser Ile
290                 295                 300

Phe Arg Leu His Val Ser Cys Ser Tyr Ser Val Ser Ser Asn Ser Leu
305                 310                 315                 320

Pro Ile Asn Val Gln Val Phe Thr Leu Pro Pro Phe Pro Glu Thr
                325                 330                 335

Gln Pro Gly Pro Leu Thr Leu Glu Leu Gln Ile Ala Lys Asp Lys Asn
            340                 345                 350

Tyr Gly Ser Tyr Tyr Gly Val Gly Asp Tyr Pro Val Val Lys Leu Leu
        355                 360                 365

Arg Asp Pro Ile Tyr Val Glu Val Ser Ile Leu His Arg Thr Asp Pro
```

```
              370             375            380
Tyr Leu Gly Leu Leu Gln Gln Cys Trp Ala Thr Pro Ser Thr Asp
385                 390             395                 400

Pro Leu Ser Gln Pro Gln Trp Pro Ile Leu Val Lys Gly Cys Pro Tyr
                405             410             415

Ile Gly Asp Asn Tyr Gln Thr Gln Leu Ile Pro Val Gln Lys Ala Leu
            420             425             430

Asp Leu Pro Phe Pro Ser His His Gln Arg Phe Ser Ile Phe Thr Phe
            435             440             445

Ser Phe Val Asn Pro Thr Val Glu Lys Gln Ala Leu Arg Gly Pro Val
    450             455             460

His Leu His Cys Ser Val Ser Val Cys Gln Pro Ala Glu Thr Pro Ser
465             470             475             480

Cys Val Val Thr Cys Pro Asp Leu Ser Arg Arg Arg Asn Phe Asp Asn
                485             490             495

Ser Ser Gln Asn Thr Thr Ala Ser Val Ser Ser Lys Gly Pro Met Ile
                500             505             510

Leu Leu Gln Ala Thr Lys Asp Pro Pro Glu Lys Leu Arg Val Pro Val
            515             520             525

Asp Ser Lys Val Leu Trp Val Ala Gly Leu Ser Gly Thr Leu Ile Leu
530             535             540

Gly Ala Leu Leu Val Ser Tyr Leu Ala Val Lys Lys Gln Lys Ser Cys
545             550             555             560

Pro Asp Gln Met Cys Gln
                565

(2) INFORMATION FOR SEQ ID NO:42:

(i) SEQUENCE CHARACTERISTICS:
        (A) LENGTH: 2266 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2235

(xi) SEQUENCE DESCRIPTION: SEQ ID NO:42:

ATG GCG TGC AGG CAG AGA GGA GGC TCT TGG AGT CCC TCA GGC TGG TTC      48
Met Ala Cys Arg Gln Arg Gly Gly Ser Trp Ser Pro Ser Gly Trp Phe
 1               5                  10                  15

AAT GCA GGC TGG AGC ACC TAC AGG TCG ATT TCT CTC TTC TTC GCC CTT      96
Asn Ala Gly Trp Ser Thr Tyr Arg Ser Ile Ser Leu Phe Phe Ala Leu
             20                  25                  30

GTG ACT TCA GGG AAC TCC ATA GAT GTT TCT CAG TTG GTA AAT CCT GCC     144
Val Thr Ser Gly Asn Ser Ile Asp Val Ser Gln Leu Val Asn Pro Ala
         35                  40                  45

TTT CCA GGC ACT GTC ACT TGC GAT GAA AGG GAA ATA ACA GTG GAG TTC     192
Phe Pro Gly Thr Val Thr Cys Asp Glu Arg Glu Ile Thr Val Glu Phe
     50                  55                  60

CCA AGC AGT CCT GGC ACC AAG AAA TGG CAT GCA TCT GTG GTG GAT CCT     240
Pro Ser Ser Pro Gly Thr Lys Lys Trp His Ala Ser Val Val Asp Pro
 65                  70                  75                  80

CTT GGT CTC GAC ATG CCG AAC TGC ACT TAC ATC CTG GAC CCA GAA AAG     288
Leu Gly Leu Asp Met Pro Asn Cys Thr Tyr Ile Leu Asp Pro Glu Lys
                 85                  90                  95

CTC ACC CTG AGG GCT ACC TAT GAT AAC TGT ACC AGG AGA GTG CAT GGT     336
```

```
            Leu Thr Leu Arg Ala Thr Tyr Asp Asn Cys Thr Arg Arg Val His Gly
                        100                 105                 110

GGA CAC CAG ATG ACC ATC AGA GTC ATG AAC AAC AGT GCT GCC TTA AGA             384
Gly His Gln Met Thr Ile Arg Val Met Asn Asn Ser Ala Ala Leu Arg
        115                 120                 125

CAC GGA GCT GTC ATG TAT CAG TTC TTC TGT CCA GCT ATG CAA GTA GAA             432
His Gly Ala Val Met Tyr Gln Phe Phe Cys Pro Ala Met Gln Val Glu
        130                 135                 140

GAG ACC CAG GGG CTT TCA GCA TCT ACA ATC TGC CAG AAG GAT TTC ATG             480
Glu Thr Gln Gly Leu Ser Ala Ser Thr Ile Cys Gln Lys Asp Phe Met
145                 150                 155                 160

TCT TTT TCC TTG CCA CGG GTC TTC TCT GGC TTG GCT GAC GAC AGT AAG             528
Ser Phe Ser Leu Pro Arg Val Phe Ser Gly Leu Ala Asp Asp Ser Lys
                165                 170                 175

GGG ACC AAA GTT CAG ATG GGA TGG AGC ATT GAG GTT GGT GAT GGT GCA             576
Gly Thr Lys Val Gln Met Gly Trp Ser Ile Glu Val Gly Asp Gly Ala
        180                 185                 190

AGA GCC AAA ACT CTG ACC CTG CCA GAG GCC ATG AAG GAA GGC TTC AGC             624
Arg Ala Lys Thr Leu Thr Leu Pro Glu Ala Met Lys Glu Gly Phe Ser
        195                 200                 205

CTC TTG ATT GAC AAC CAC AGG ATG ACC TTC CAT GTG CCA TTC AAT GCC             672
Leu Leu Ile Asp Asn His Arg Met Thr Phe His Val Pro Phe Asn Ala
    210                 215                 220

ACT GGA GTG ACT CAC TAT GTG CAA GGT AAC AGT CAT CTC TAC ATG GTG             720
Thr Gly Val Thr His Tyr Val Gln Gly Asn Ser His Leu Tyr Met Val
225                 230                 235                 240

TCT CTG AAG CTT ACA TTT ATA TCT CCT GGA CAG AAG GTG ATC TTC TCT             768
Ser Leu Lys Leu Thr Phe Ile Ser Pro Gly Gln Lys Val Ile Phe Ser
                245                 250                 255

TCA CAA GCT ATT TGT GCA CCA GAT CCT GTG ACC TGC AAT GCC ACA CAC             816
Ser Gln Ala Ile Cys Ala Pro Asp Pro Val Thr Cys Asn Ala Thr His
            260                 265                 270

ATG ACT CTC ACC ATA CCA GAG TTT CCT GGG AAG CTT AAG TCT GTG AGC             864
Met Thr Leu Thr Ile Pro Glu Phe Pro Gly Lys Leu Lys Ser Val Ser
        275                 280                 285

TTT GAA AAC CAG AAC ATT GAT GTG AGC CAG CTG CAT GAC AAT GGA ATT             912
Phe Glu Asn Gln Asn Ile Asp Val Ser Gln Leu His Asp Asn Gly Ile
    290                 295                 300

GAT CTA GAA GCA ACA AAT GGC ATG AAA TTG CAT TTC AGC AAA ACT CTG             960
Asp Leu Glu Ala Thr Asn Gly Met Lys Leu His Phe Ser Lys Thr Leu
305                 310                 315                 320

CTC AAA ACG AAA TTA TCT GAA AAA TGC CTA CTC CAT CAG TTC TAC TTA             1008
Leu Lys Thr Lys Leu Ser Glu Lys Cys Leu Leu His Gln Phe Tyr Leu
                325                 330                 335

GCT TCA CTC AAG CTG ACC TTT CTC CTT CGG CCA GAG ACA GTA TCC ATG             1056
Ala Ser Leu Lys Leu Thr Phe Leu Leu Arg Pro Glu Thr Val Ser Met
            340                 345                 350

GTG ATC TAT CCT GAG TGT CTC TGT GAG TCA CCC GTT TCT ATA GTT ACA             1104
Val Ile Tyr Pro Glu Cys Leu Cys Glu Ser Pro Val Ser Ile Val Thr
        355                 360                 365

GGG GAG CTG TGC ACC CAG GAT GGG TTT ATG GAC GTC GAG GTC TAC AGC             1152
Gly Glu Leu Cys Thr Gln Asp Gly Phe Met Asp Val Glu Val Tyr Ser
    370                 375                 380

TAC CAA ACA CAA CCA GCT CTT GAC CTG GGT ACT CTG AGG GTG GGA AAC             1200
Tyr Gln Thr Gln Pro Ala Leu Asp Leu Gly Thr Leu Arg Val Gly Asn
385                 390                 395                 400

TCA TCC TGC CAG CCT GTC TTT GAG GCT CAG TCT CAG GGG CTG GTA CGG             1248
Ser Ser Cys Gln Pro Val Phe Glu Ala Gln Ser Gln Gly Leu Val Arg
                405                 410                 415

TTC CAC ATA CCC CTG AAT GGA TGT GGA ACG AGA TAT AAG TTC GAA GAT             1296
```

```
          Phe His Ile Pro Leu Asn Gly Cys Gly Thr Arg Tyr Lys Phe Glu Asp
                  420                 425                 430

GAT AAA GTC GTC TAT GAA AAC GAA ATA CAT GCT CTC TGG ACG GAT TTT             1344
Asp Lys Val Val Tyr Glu Asn Glu Ile His Ala Leu Trp Thr Asp Phe
            435                 440                 445

CCT CCA AGC AAA ATA TCT AGA GAC AGT GAG TTC AGA ATG ACA GTG AAG             1392
Pro Pro Ser Lys Ile Ser Arg Asp Ser Glu Phe Arg Met Thr Val Lys
450                 455                 460

TGT TCT TAT AGC AGG AAT GAC ATG CTA CTA AAC ATC AAC GTT GAA AGC             1440
Cys Ser Tyr Ser Arg Asn Asp Met Leu Leu Asn Ile Asn Val Glu Ser
465                 470                 475                 480

CTT ACT CCT CCA GTG GCC TCA GTG AAG TTG GGT CCA TTT ACC TTG ATC             1488
Leu Thr Pro Pro Val Ala Ser Val Lys Leu Gly Pro Phe Thr Leu Ile
                485                 490                 495

CTG CAA AGC TAC CCA GAT AAT TCC TAC CAA CAA CCT TAT GGG GAA AAC             1536
Leu Gln Ser Tyr Pro Asp Asn Ser Tyr Gln Gln Pro Tyr Gly Glu Asn
            500                 505                 510

GAG TAC CCT CTA GTG AGA TTC CTC CGC CAA CCA ATT TAC ATG GAA GTG             1584
Glu Tyr Pro Leu Val Arg Phe Leu Arg Gln Pro Ile Tyr Met Glu Val
        515                 520                 525

AGA GTC CTA AAC AGG GAT GAC CCC AAC ATC AAG CTG GTC TTA GAT GAC             1632
Arg Val Leu Asn Arg Asp Asp Pro Asn Ile Lys Leu Val Leu Asp Asp
    530                 535                 540

TGC TGG GCG ACG TCC ACC ATG GAT CCA GAC TCT TTC CCC CAG TGG AAC             1680
Cys Trp Ala Thr Ser Thr Met Asp Pro Asp Ser Phe Pro Gln Trp Asn
545                 550                 555                 560

GTT GTC GTG GAT GGC TGT GCA TAT GAC CTG GAC AAC TAC CAG ACC ACC             1728
Val Val Val Asp Gly Cys Ala Tyr Asp Leu Asp Asn Tyr Gln Thr Thr
                565                 570                 575

TTC CAT CCA GTC GGC TCC TCT GTG ACC CAT CCT GAT CAC TAT CAG AGG             1776
Phe His Pro Val Gly Ser Ser Val Thr His Pro Asp His Tyr Gln Arg
            580                 585                 590

TTT GAC ATG AAG GCT TTT GCC TTT GTA TCA GAA GCC CAC GTG CTC TCT             1824
Phe Asp Met Lys Ala Phe Ala Phe Val Ser Glu Ala His Val Leu Ser
        595                 600                 605

AGC CTG GTC TAC TTC CAC TGC AGT GCC TTA ATC TGT AAT CGA CTC TCC             1872
Ser Leu Val Tyr Phe His Cys Ser Ala Leu Ile Cys Asn Arg Leu Ser
    610                 615                 620

CCT GAC TCC CCA CTG TGT TCT GTG ACC TGC CCT GTG TCC TCT AGG CAC             1920
Pro Asp Ser Pro Leu Cys Ser Val Thr Cys Pro Val Ser Ser Arg His
625                 630                 635                 640

AGG CGA GCC ACA GGG GCC ACT GAA GCA GAG AAA ATG ACA GTC AGC CTC             1968
Arg Arg Ala Thr Gly Ala Thr Glu Ala Glu Lys Met Thr Val Ser Leu
                645                 650                 655

CCA GGA CCC ATT CTC CTG TTG TCA GAT GAC TCC TCA TTC AGA GGT GTC             2016
Pro Gly Pro Ile Leu Leu Leu Ser Asp Asp Ser Ser Phe Arg Gly Val
            660                 665                 670

GGC TCA TCT GAT CTA AAA GCA AGT GGG AGC AGT GGG GAG AAG AGT AGG             2064
Gly Ser Ser Asp Leu Lys Ala Ser Gly Ser Ser Gly Glu Lys Ser Arg
        675                 680                 685

AGT GAA ACA GGG GAG GAG GTT GGC TCA CGA GGT GCT ATG GAC ACC AAA             2112
Ser Glu Thr Gly Glu Glu Val Gly Ser Arg Gly Ala Met Asp Thr Lys
    690                 695                 700

GGG CAC AAG ACT GCT GGA GAT GTT GGT TCC AAA GCT GTG GCT GCT GTG             2160
Gly His Lys Thr Ala Gly Asp Val Gly Ser Lys Ala Val Ala Ala Val
705                 710                 715                 720

GCT GCC TTT GCA GGT GTG GTG GCA ACT CTA GGC TTC ATC TAC TAC CTG             2208
Ala Ala Phe Ala Gly Val Val Ala Thr Leu Gly Phe Ile Tyr Tyr Leu
                725                 730                 735

TAC GAG AAA AGG ACT GTG TCA AAT CAC TAAATGGGCT TCTAAATAAA                   2255
```

```
Tyr Glu Lys Arg Thr Val Ser Asn His
            740                 745

GCAGTCAAAA T                                                    2266
```

(2) INFORMATION FOR SEQ ID NO:43:

(i) SEQUENCE CHARACTERISTICS:
        (A) LENGTH: 745 amino acids
        (B) TYPE: amino acid
        (D) TOPOLOGY: linear (ii) MOLECULE TYPE: protein (xi) SEQUENCE DESCRIPTION: SEQ ID NO:43:

```
Met Ala Cys Arg Gln Arg Gly Gly Ser Trp Ser Pro Ser Gly Trp Phe
 1               5                  10                  15

Asn Ala Gly Trp Ser Thr Tyr Arg Ser Ile Ser Leu Phe Phe Ala Leu
            20                  25                  30

Val Thr Ser Gly Asn Ser Ile Asp Val Ser Gln Leu Val Asn Pro Ala
        35                  40                  45

Phe Pro Gly Thr Val Thr Cys Asp Glu Arg Glu Ile Thr Val Glu Phe
    50                  55                  60

Pro Ser Ser Pro Gly Thr Lys Lys Trp His Ala Ser Val Val Asp Pro
65                  70                  75                  80

Leu Gly Leu Asp Met Pro Asn Cys Thr Tyr Ile Leu Asp Pro Glu Lys
                85                  90                  95

Leu Thr Leu Arg Ala Thr Tyr Asp Asn Cys Thr Arg Arg Val His Gly
            100                 105                 110

Gly His Gln Met Thr Ile Arg Val Met Asn Asn Ser Ala Ala Leu Arg
        115                 120                 125

His Gly Ala Val Met Tyr Gln Phe Phe Cys Pro Ala Met Gln Val Glu
    130                 135                 140

Glu Thr Gln Gly Leu Ser Ala Ser Thr Ile Cys Gln Lys Asp Phe Met
145                 150                 155                 160

Ser Phe Ser Leu Pro Arg Val Phe Ser Gly Leu Ala Asp Asp Ser Lys
                165                 170                 175

Gly Thr Lys Val Gln Met Gly Trp Ser Ile Glu Val Gly Asp Gly Ala
            180                 185                 190

Arg Ala Lys Thr Leu Thr Leu Pro Glu Ala Met Lys Glu Gly Phe Ser
        195                 200                 205

Leu Leu Ile Asp Asn His Arg Met Thr Phe His Val Pro Phe Asn Ala
    210                 215                 220

Thr Gly Val Thr His Tyr Val Gln Gly Asn Ser His Leu Tyr Met Val
225                 230                 235                 240

Ser Leu Lys Leu Thr Phe Ile Ser Pro Gly Gln Lys Val Ile Phe Ser
                245                 250                 255

Ser Gln Ala Ile Cys Ala Pro Asp Pro Val Thr Cys Asn Ala Thr His
            260                 265                 270

Met Thr Leu Thr Ile Pro Glu Phe Pro Gly Lys Leu Lys Ser Val Ser
        275                 280                 285

Phe Glu Asn Gln Asn Ile Asp Val Ser Gln Leu His Asp Asn Gly Ile
    290                 295                 300

Asp Leu Glu Ala Thr Asn Gly Met Lys Leu His Phe Ser Lys Thr Leu
305                 310                 315                 320

Leu Lys Thr Lys Leu Ser Glu Lys Cys Leu Leu His Gln Phe Tyr Leu
                325                 330                 335
```

-continued

```
Ala Ser Leu Lys Leu Thr Phe Leu Leu Arg Pro Glu Thr Val Ser Met
        340                 345                 350

Val Ile Tyr Pro Glu Cys Leu Cys Glu Ser Pro Val Ser Ile Val Thr
            355                 360                 365

Gly Glu Leu Cys Thr Gln Asp Gly Phe Met Asp Val Glu Val Tyr Ser
370                 375                 380

Tyr Gln Thr Gln Pro Ala Leu Asp Leu Gly Thr Leu Arg Val Gly Asn
385                 390                 395                 400

Ser Ser Cys Gln Pro Val Phe Glu Ala Gln Ser Gln Gly Leu Val Arg
                405                 410                 415

Phe His Ile Pro Leu Asn Gly Cys Gly Thr Arg Tyr Lys Phe Glu Asp
                420                 425                 430

Asp Lys Val Val Tyr Glu Asn Glu Ile His Ala Leu Trp Thr Asp Phe
            435                 440                 445

Pro Pro Ser Lys Ile Ser Arg Asp Ser Glu Phe Arg Met Thr Val Lys
450                 455                 460

Cys Ser Tyr Ser Arg Asn Asp Met Leu Leu Asn Ile Asn Val Glu Ser
465                 470                 475                 480

Leu Thr Pro Pro Val Ala Ser Val Lys Leu Gly Pro Phe Thr Leu Ile
                485                 490                 495

Leu Gln Ser Tyr Pro Asp Asn Ser Tyr Gln Gln Pro Tyr Gly Glu Asn
                500                 505                 510

Glu Tyr Pro Leu Val Arg Phe Leu Arg Gln Pro Ile Tyr Met Glu Val
                515                 520                 525

Arg Val Leu Asn Arg Asp Asp Pro Asn Ile Lys Leu Val Leu Asp Asp
530                 535                 540

Cys Trp Ala Thr Ser Thr Met Asp Pro Asp Ser Phe Pro Gln Trp Asn
545                 550                 555                 560

Val Val Val Asp Gly Cys Ala Tyr Asp Leu Asp Asn Tyr Gln Thr Thr
                565                 570                 575

Phe His Pro Val Gly Ser Ser Val Thr His Pro Asp His Tyr Gln Arg
                580                 585                 590

Phe Asp Met Lys Ala Phe Ala Phe Val Ser Glu Ala His Val Leu Ser
                595                 600                 605

Ser Leu Val Tyr Phe His Cys Ser Ala Leu Ile Cys Asn Arg Leu Ser
            610                 615                 620

Pro Asp Ser Pro Leu Cys Ser Val Thr Cys Pro Val Ser Ser Arg His
625                 630                 635                 640

Arg Arg Ala Thr Gly Ala Thr Glu Ala Glu Lys Met Thr Val Ser Leu
                645                 650                 655

Pro Gly Pro Ile Leu Leu Leu Ser Asp Asp Ser Ser Phe Arg Gly Val
                660                 665                 670

Gly Ser Ser Asp Leu Lys Ala Ser Gly Ser Ser Gly Glu Lys Ser Arg
                675                 680                 685

Ser Glu Thr Gly Glu Glu Val Gly Ser Arg Gly Ala Met Asp Thr Lys
690                 695                 700

Gly His Lys Thr Ala Gly Asp Val Gly Ser Lys Ala Val Ala Ala Val
705                 710                 715                 720

Ala Ala Phe Ala Gly Val Val Ala Thr Leu Gly Phe Ile Tyr Tyr Leu
                725                 730                 735

Tyr Glu Lys Arg Thr Val Ser Asn His
                740                 745
```

(2) INFORMATION FOR SEQ ID NO:44:

(i) SEQUENCE CHARACTERISTICS:
    (A) LENGTH: 560 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 15..506

(xi) SEQUENCE DESCRIPTION: SEQ ID NO:44:

```
GAATTCGCGG CCGC TCC TCT GTG ACC CAT CCT GAT CAC TAT CAG AGG TTT          50
               Ser Ser Val Thr His Pro Asp His Tyr Gln Arg Phe
                1               5                  10

GAC ATG AAG GCT TTT GCC TTT GTA TCA GAG GCC CAT GTG CTC TCT AGC          98
Asp Met Lys Ala Phe Ala Phe Val Ser Glu Ala His Val Leu Ser Ser
         15                  20                  25

CTG GTC TAC TTC CAC TGC AGT GCC TTA ATC TGC AAT CGA CTC TCT CCA         146
Leu Val Tyr Phe His Cys Ser Ala Leu Ile Cys Asn Arg Leu Ser Pro
     30                  35                  40

GAC TCC CCT CTG TGT TCT GTG ACC TGC CCT GTG TCA TCT AGG CAC AGG         194
Asp Ser Pro Leu Cys Ser Val Thr Cys Pro Val Ser Ser Arg His Arg
 45              50                  55                      60

CGA GCC ACA GGG GCC ACT GAA GCA GAG AAA ATG ACA GTC AGC CTC CCA         242
Arg Ala Thr Gly Ala Thr Glu Ala Glu Lys Met Thr Val Ser Leu Pro
                 65                  70                  75

GGA CCC ATT CTC CTG TTG TCA GAC GAC TCC TCA TTC AGA GGT GTT GGC         290
Gly Pro Ile Leu Leu Leu Ser Asp Asp Ser Ser Phe Arg Gly Val Gly
             80                  85                  90

TCA TCT GAT CTA AAA GCA AGT GGG AGC AGT GGG GAG AAC AGT AGG AGC         338
Ser Ser Asp Leu Lys Ala Ser Gly Ser Ser Gly Glu Asn Ser Arg Ser
         95                  100                 105

GAA ACA GGG GAG GAG GTT GGC TCA CGA GAT GTT ATG GAC ACC AAA GGG         386
Glu Thr Gly Glu Glu Val Gly Ser Arg Asp Val Met Asp Thr Lys Gly
     110                 115                 120

CAC AGG ACT GCT GGA GAT GTT GGT TCC AAA GCT GTG GCT GCT GTG GCT         434
His Arg Thr Ala Gly Asp Val Gly Ser Lys Ala Val Ala Ala Val Ala
125              130                 135                     140

GCC TTG GCA GGT GTG GTG GCA ACT CTA GGC TTC ATC TGT TAC CTG TAT         482
Ala Leu Ala Gly Val Val Ala Thr Leu Gly Phe Ile Cys Tyr Leu Tyr
                 145                 150                 155

AAG AAA AGG ACT GTG TCA AAT CAC TAAATGGGCT TCTAAATAAA GCAGTCAAAA        536
Lys Lys Arg Thr Val Ser Asn His
                 160

TAAAAAAAAA GCGGCCGCGA ATTC                                              560
```

(2) INFORMATION FOR SEQ ID NO:45:

(i) SEQUENCE CHARACTERISTICS:
        (A) LENGTH: 164 amino acids
        (B) TYPE: amino acid
        (D) TOPOLOGY: linear (ii) MOLECULE TYPE: protein (xi) SEQUENCE DESCRIPTION: SEQ ID NO:45:

```
Ser Ser Val Thr His Pro Asp His Tyr Gln Arg Phe Asp Met Lys Ala
 1               5                  10                  15

Phe Ala Phe Val Ser Glu Ala His Val Leu Ser Ser Leu Val Tyr Phe
             20                  25                  30

His Cys Ser Ala Leu Ile Cys Asn Arg Leu Ser Pro Asp Ser Pro Leu
```

```
                      35                  40                  45
Cys Ser Val Thr Cys Pro Val Ser Ser Arg His Arg Arg Ala Thr Gly
    50                  55                  60

Ala Thr Glu Ala Glu Lys Met Thr Val Ser Leu Pro Gly Pro Ile Leu
65                  70                  75                  80

Leu Leu Ser Asp Asp Ser Ser Phe Arg Gly Val Gly Ser Ser Asp Leu
                85                  90                  95

Lys Ala Ser Gly Ser Ser Gly Glu Asn Ser Arg Ser Glu Thr Gly Glu
            100                 105                 110

Glu Val Gly Ser Arg Asp Val Met Asp Thr Lys Gly His Arg Thr Ala
            115                 120                 125

Gly Asp Val Gly Ser Lys Ala Val Ala Ala Val Ala Ala Leu Ala Gly
130                 135                 140

Val Val Ala Thr Leu Gly Phe Ile Cys Tyr Leu Tyr Lys Lys Arg Thr
145                 150                 155                 160

Val Ser Asn His
```

(2) INFORMATION FOR SEQ ID NO:46:

(i) SEQUENCE CHARACTERISTICS:
  (A) LENGTH: 866 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 12..821

(xi) SEQUENCE DESCRIPTION: SEQ ID NO:46:

```
GAATTCGCGG C CGC CGT GGC TCT GTC ACT CGT GAC AGC ATC TTC AGG CTC          50
            Arg Arg Gly Ser Val Thr Arg Asp Ser Ile Phe Arg Leu
             1               5                  10

CAT GTC AGC TGC AGC TAC TCA GTA AGT AGC AAC TCT CTC CCA ATC AAG          98
His Val Ser Cys Ser Tyr Ser Val Ser Ser Asn Ser Leu Pro Ile Lys
     15                  20                  25

GTC CAG GTT TTT ACT CTC CCA CCA CCC TTT CCT GAG ACC CAG CCT GGA         146
Val Gln Val Phe Thr Leu Pro Pro Pro Phe Pro Glu Thr Gln Pro Gly
 30                  35                  40                  45

CCC CTC ACT CTG GAA CTT CAG ATT GCC AAA GAT AAA AAC TAT GGC TCC         194
Pro Leu Thr Leu Glu Leu Gln Ile Ala Lys Asp Lys Asn Tyr Gly Ser
                 50                  55                  60

TAC TAT GGT GTT GGT GAC TAC CCC GTG GTG AAG TTG CTT CGG GAT CCC         242
Tyr Tyr Gly Val Gly Asp Tyr Pro Val Val Lys Leu Leu Arg Asp Pro
             65                  70                  75

ATC TAT GTG GAG GTC TCC ATC CTT CAC AGA ACA GAC CCC TCC CTG GGG         290
Ile Tyr Val Glu Val Ser Ile Leu His Arg Thr Asp Pro Ser Leu Gly
         80                  85                  90

CTG CTC CTA CAT CAG TGT TGG GCA ACA CCC AGC ACA GAC CCA CTG AGT         338
Leu Leu Leu His Gln Cys Trp Ala Thr Pro Ser Thr Asp Pro Leu Ser
     95                 100                 105

CAG CCA CAG TGG CCC ATC CTG GTA AAG GGC TGC CCC TAC ATT GGA GAC         386
Gln Pro Gln Trp Pro Ile Leu Val Lys Gly Cys Pro Tyr Ile Gly Asp
110                 115                 120                 125

AAC TAT CAG ACC CAG CTG ATC CCT GTC CAG AAA GCC TTG GAT CTT CCA         434
Asn Tyr Gln Thr Gln Leu Ile Pro Val Gln Lys Ala Leu Asp Leu Pro
                130                 135                 140

TTT CCC TCT CAC TAC CAG CGC TTC AGC ATC TTC ACC TTC AGC TTT GTG         482
Phe Pro Ser His Tyr Gln Arg Phe Ser Ile Phe Thr Phe Ser Phe Val
```

```
                    145                 150                 155
GAC CCT ACA GCG GAG AAA CAG GCC CTC AGG GGA CCG GTG CAT CTG CAC    530
Asp Pro Thr Ala Glu Lys Gln Ala Leu Arg Gly Pro Val His Leu His
        160                 165                 170

TGC AGT GTG TCA GTC TGC CAG CCT GCT GAG ACA CCA TCC TGT GCG GTA    578
Cys Ser Val Ser Val Cys Gln Pro Ala Glu Thr Pro Ser Cys Ala Val
    175                 180                 185

ACC TGT CCT GAT CTC AGT CGA AGA AAT TCA GGC ACC ATT TTT CAG AAC    626
Thr Cys Pro Asp Leu Ser Arg Arg Asn Ser Gly Thr Ile Phe Gln Asn
190                 195                 200                 205

ACT ACT GCT AGT GTT TCT AGC AAA GGC CCC ATG ATT CTA CTC CAA GCC    674
Thr Thr Ala Ser Val Ser Ser Lys Gly Pro Met Ile Leu Leu Gln Ala
                210                 215                 220

ACT AAG GAC CCT CCA GAA AAG CTC CGT GCT CCT GTA GAC TCA AAA GTT    722
Thr Lys Asp Pro Pro Glu Lys Leu Arg Ala Pro Val Asp Ser Lys Val
            225                 230                 235

CTG TGG GTG GCA GGC CTT TCT GGG ACC TTA ATC CTT GGA GGC TTA GTA    770
Leu Trp Val Ala Gly Leu Ser Gly Thr Leu Ile Leu Gly Gly Leu Val
        240                 245                 250

GTA TCC TAC TTG GCT ATC AAA CAG CTG AAT TGT CCA GAC CAA ACA TGT    818
Val Ser Tyr Leu Ala Ile Lys Gln Leu Asn Cys Pro Asp Gln Thr Cys
    255                 260                 265

CAA TAAAACCAGA CTGTACTCCC AAAAAAAAAA AGCGGCCGCG AATTC              866
Gln

270

(2) INFORMATION FOR SEQ ID NO:47:

(i) SEQUENCE CHARACTERISTICS:
        (A) LENGTH: 270 amino acids
        (B) TYPE: amino acid
        (D) TOPOLOGY: linear (ii) MOLECULE TYPE: protein (xi) SEQUENCE DESCRIPTION: SEQ ID NO:47:

Arg Arg Gly Ser Val Thr Arg Asp Ser Ile Phe Arg Leu His Val Ser
  1               5                  10                  15

Cys Ser Tyr Ser Val Ser Ser Asn Ser Leu Pro Ile Lys Val Gln Val
                20                  25                  30

Phe Thr Leu Pro Pro Phe Pro Glu Thr Gln Pro Gly Pro Leu Thr
         35                  40                  45

Leu Glu Leu Gln Ile Ala Lys Asp Lys Asn Tyr Gly Ser Tyr Tyr Gly
     50                  55                  60

Val Gly Asp Tyr Pro Val Val Lys Leu Leu Arg Asp Pro Ile Tyr Val
 65                  70                  75                  80

Glu Val Ser Ile Leu His Arg Thr Asp Pro Ser Leu Gly Leu Leu Leu
                 85                  90                  95

His Gln Cys Trp Ala Thr Pro Ser Thr Asp Pro Leu Ser Gln Pro Gln
            100                 105                 110

Trp Pro Ile Leu Val Lys Gly Cys Pro Tyr Ile Gly Asp Asn Tyr Gln
        115                 120                 125

Thr Gln Leu Ile Pro Val Gln Lys Ala Leu Asp Leu Pro Phe Pro Ser
    130                 135                 140

His Tyr Gln Arg Phe Ser Ile Phe Thr Phe Ser Phe Val Asp Pro Thr
145                 150                 155                 160

Ala Glu Lys Gln Ala Leu Arg Gly Pro Val His Leu His Cys Ser Val
                165                 170                 175
```

```
Ser Val Cys Gln Pro Ala Glu Thr Pro Ser Cys Ala Val Thr Cys Pro
            180                 185                 190

Asp Leu Ser Arg Arg Asn Ser Gly Thr Ile Phe Gln Asn Thr Thr Ala
            195                 200                 205

Ser Val Ser Ser Lys Gly Pro Met Ile Leu Leu Gln Ala Thr Lys Asp
            210                 215                 220

Pro Pro Glu Lys Leu Arg Ala Pro Val Asp Ser Lys Val Leu Trp Val
225                 230                 235                 240

Ala Gly Leu Ser Gly Thr Leu Ile Leu Gly Leu Val Val Ser Tyr
                245                 250                 255

Leu Ala Ile Lys Gln Leu Asn Cys Pro Asp Gln Thr Cys Gln
            260                 265                 270
```

(2) INFORMATION FOR SEQ ID NO:48:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 15..683

(xi) SEQUENCE DESCRIPTION: SEQ ID NO:48:

```
GAATTCGCGG CCGC ATC CAC ACT GGC AGC CAC GTG CCA CTG CGG TTG TTT        50
                Ile His Thr Gly Ser His Val Pro Leu Arg Leu Phe
                 1               5                  10

GTG GAC CAC TGC GTG GCC ACA CCA ACA CCA GAC CAG AAT GCC TCC CCT        98
Val Asp His Cys Val Ala Thr Pro Thr Pro Asp Gln Asn Ala Ser Pro
             15                  20                  25

TAT CAC ACC ATC GTG GAC TTC CAT GGC TGT CTT GTC GAT GGT CTC ACT       146
Tyr His Thr Ile Val Asp Phe His Gly Cys Leu Val Asp Gly Leu Thr
 30                  35                  40

GAT GCC TCT TCT GCG TTC AAA GTT CCT CGA CCC GGG CCA GAT ACA CTC       194
Asp Ala Ser Ser Ala Phe Lys Val Pro Arg Pro Gly Pro Asp Thr Leu
 45                  50                  55                  60

CAG TTC ACA GTG GAT GTC TTC CAC TTT GCT AAT GAC TCC AGA AAC ATG       242
Gln Phe Thr Val Asp Val Phe His Phe Ala Asn Asp Ser Arg Asn Met
                 65                  70                  75

ATA TAC ATC ACC TGC CAC CTG AAG GCC ATC CCA GCT GAG CAG GAA CCA       290
Ile Tyr Ile Thr Cys His Leu Lys Ala Ile Pro Ala Glu Gln Glu Pro
                 80                  85                  90

GAC GAA CTC AAC AAA GCC TGT TCC TTC AGC AAG TCT TCC AAC AGC TGG       338
Asp Glu Leu Asn Lys Ala Cys Ser Phe Ser Lys Ser Ser Asn Ser Trp
             95                  100                 105

TTC CCA GTG GAA GGC CCA GCT GAC ATC TGT CAA TGC TGT AGC AAG GGT       386
Phe Pro Val Glu Gly Pro Ala Asp Ile Cys Gln Cys Cys Ser Lys Gly
         110                 115                 120

GAC TGT GGC ACT CCA AGC CAT TCC AGG AGG CAG CCC CAT GTC GTG AGC       434
Asp Cys Gly Thr Pro Ser His Ser Arg Arg Gln Pro His Val Val Ser
125                 130                 135                 140

CAG TGG TCC AGG TCT GCT TCT CGT AAC CGC AGG CAT GTG ACA GAA GAA       482
Gln Trp Ser Arg Ser Ala Ser Arg Asn Arg Arg His Val Thr Glu Glu
                145                 150                 155

GCA GAT ATC ACC GTG GGG CCA CTG ATC TTC CTG GAC AGG AGT GCT GAC       530
Ala Asp Ile Thr Val Gly Pro Leu Ile Phe Leu Asp Arg Ser Ala Asp
             160                 165                 170

TAT GAA GTA GAA CAG TGG GCC TTG CCG ACT GAC ACC TCC GTG CTG CTG       578
```

```
Tyr Glu Val Glu Gln Trp Ala Leu Pro Thr Asp Thr Ser Val Leu Leu
            175                 180                 185

CTG GGC ATA GGC CTG GCC GTG GTG GCA TCT CTG ACT CTG ACC GCT GTT            626
Leu Gly Ile Gly Leu Ala Val Val Ala Ser Leu Thr Leu Thr Ala Val
        190                 195                 200

ATC CTG ATT TTC ACC AGG AGG TGG CGC ACT GCC TCC CGC CCT GTG TCT            674
Ile Leu Ile Phe Thr Arg Arg Trp Arg Thr Ala Ser Arg Pro Val Ser
205                 210                 215                 220

GTT TCC CAA TAAAAGAAGA AAGCAGTAAA AAAAAGCGGC CGCGAATTC                     722
Val Ser Gln
```

(2) INFORMATION FOR SEQ ID NO:49:

(i) SEQUENCE CHARACTERISTICS:
        (A) LENGTH: 223 amino acids
        (B) TYPE: amino acid
        (D) TOPOLOGY: linear (ii) MOLECULE TYPE: protein (xi) SEQUENCE DESCRIPTION: SEQ ID NO:49:

```
Ile His Thr Gly Ser His Val Pro Leu Arg Leu Phe Val Asp His Cys
1                   5                  10                  15

Val Ala Thr Pro Thr Pro Asp Gln Asn Ala Ser Pro Tyr His Thr Ile
                20                  25                  30

Val Asp Phe His Gly Cys Leu Val Asp Gly Leu Thr Asp Ala Ser Ser
            35                  40                  45

Ala Phe Lys Val Pro Arg Pro Gly Pro Asp Thr Leu Gln Phe Thr Val
        50                  55                  60

Asp Val Phe His Phe Ala Asn Asp Ser Arg Asn Met Ile Tyr Ile Thr
65                  70                  75                  80

Cys His Leu Lys Ala Ile Pro Ala Glu Gln Glu Pro Asp Glu Leu Asn
                85                  90                  95

Lys Ala Cys Ser Phe Ser Lys Ser Ser Asn Ser Trp Phe Pro Val Glu
                100                 105                 110

Gly Pro Ala Asp Ile Cys Gln Cys Cys Ser Lys Gly Asp Cys Gly Thr
            115                 120                 125

Pro Ser His Ser Arg Arg Gln Pro His Val Val Ser Gln Trp Ser Arg
        130                 135                 140

Ser Ala Ser Arg Asn Arg Arg His Val Thr Glu Glu Ala Asp Ile Thr
145                 150                 155                 160

Val Gly Pro Leu Ile Phe Leu Asp Arg Ser Ala Asp Tyr Glu Val Glu
                165                 170                 175

Gln Trp Ala Leu Pro Thr Asp Ser Val Leu Leu Leu Gly Ile Gly
            180                 185                 190

Leu Ala Val Val Ala Ser Leu Thr Leu Thr Ala Val Ile Leu Ile Phe
        195                 200                 205

Thr Arg Arg Trp Arg Thr Ala Ser Arg Pro Val Ser Val Ser Gln
            210                 215                 220
```

(2) INFORMATION FOR SEQ ID NO:50:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

```
CGCCCTTCCC AGCAACTGCA CCATCACCAC CATGGG                                      36

(2) INFORMATION FOR SEQ ID NO:51:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:51:

GATCCCCATG GTGGTGGTGA TGGTGCAGTT GCTGGGAAGG GCGAT                            45

(2) INFORMATION FOR SEQ ID NO:52:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:52:

GATCCCTCGA GCCACCATCA CCACCATCAT G                                          31

(2) INFORMATION FOR SEQ ID NO:53:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:53:

AATTCATGAT GGTGGTGATG GTGGCTCGAG G                                          31

(2) INFORMATION FOR SEQ ID NO:54:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

CCCGGATCCG CAGACCATCT GGCCAACTGA G                                          31

(2) INFORMATION FOR SEQ ID NO:55:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

GCGCTCGAGG GCATATGGCT GCCAGTGTG                                             29

(2) INFORMATION FOR SEQ ID NO:56:
```

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:56:

CGCGCTAGCA GATCTATGGC GCCGAGCTGG AGGTTC                          36

(2) INFORMATION FOR SEQ ID NO:57:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

CGCGGATCCT ATTAATGGTG GTGATGGTGG TGACTAGTGG ACCCTTCCA            49

(2) INFORMATION FOR SEQ ID NO:58:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

CCCGCTAGCA GATCTATGGG GCTGAGCTAT GGAATTTTC                       39

(2) INFORMATION FOR SEQ ID NO:59:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:59:

CGCACTAGTT GACCCCTCTA TACCATGATC ACTA                            34

(2) INFORMATION FOR SEQ ID NO:60:

(i) SEQUENCE CHARACTERISTICS:
        (A) LENGTH: 1299 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "human ZPC"

(ix) FEATURE:
        (A) NAME/KEY: CDS
        (B) LOCATION: 11..1282

(xi) SEQUENCE DESCRIPTION: SEQ ID NO:60:

TGCAGGTACC ATG GAG CTG AGC TAT AGG CTC TTC ATC TGC CTC CTG CTC   49
           Met Glu Leu Ser Tyr Arg Leu Phe Ile Cys Leu Leu Leu
            1               5                  10

| | | | | | | | | | | | | | | | | |
|---|---|---|---|---|---|---|---|---|---|---|---|---|---|---|---|---|
| TGG | GGT | AGT | ACT | GAG | CTG | TGC | TAC | CCC | CAA | CCC | CTC | TGG | CTC | TTG | CAG | 97 |
| Trp | Gly | Ser | Thr | Glu | Leu | Cys | Tyr | Pro | Gln | Pro | Leu | Trp | Leu | Leu | Gln | |
| | 15 | | | | 20 | | | | | 25 | | | | | | |
| GGT | GGA | GCC | AGC | CAT | CCT | GAG | ACG | TCC | GTA | CAG | CCC | GTA | CTG | GTG | GAG | 145 |
| Gly | Gly | Ala | Ser | His | Pro | Glu | Thr | Ser | Val | Gln | Pro | Val | Leu | Val | Glu | |
| 30 | | | | | 35 | | | | | 40 | | | | | 45 | |
| TGT | CAG | GAG | GCC | ACT | CTG | ATG | GTC | ATG | GTC | AGC | AAA | GAC | CTT | TTT | GGC | 193 |
| Cys | Gln | Glu | Ala | Thr | Leu | Met | Val | Met | Val | Ser | Lys | Asp | Leu | Phe | Gly | |
| | | | | 50 | | | | | 55 | | | | | 60 | | |
| ACC | GGG | AAG | CTC | ATC | AGG | GCT | GCT | GAC | CTC | ACC | TTG | GGC | CCA | GAG | GCC | 241 |
| Thr | Gly | Lys | Leu | Ile | Arg | Ala | Ala | Asp | Leu | Thr | Leu | Gly | Pro | Glu | Ala | |
| | | | 65 | | | | | 70 | | | | | 75 | | | |
| TGT | GAG | CCT | CTG | GTC | TCC | ATG | GAC | ACA | GAA | GAT | GTG | GTC | AGG | TTT | GAG | 289 |
| Cys | Glu | Pro | Leu | Val | Ser | Met | Asp | Thr | Glu | Asp | Val | Val | Arg | Phe | Glu | |
| | | 80 | | | | | 85 | | | | | 90 | | | | |
| GTT | GGA | CTC | CAC | GAG | TGT | GGC | AAC | AGC | ATG | CAG | GTA | ACT | GAC | GAT | GCC | 337 |
| Val | Gly | Leu | His | Glu | Cys | Gly | Asn | Ser | Met | Gln | Val | Thr | Asp | Asp | Ala | |
| | 95 | | | | | 100 | | | | | 105 | | | | | |
| CTG | GTG | TAC | AGC | ACC | TTC | CTG | CTC | CAT | GAC | CCC | CGC | CCC | GTG | GGA | AAC | 385 |
| Leu | Val | Tyr | Ser | Thr | Phe | Leu | Leu | His | Asp | Pro | Arg | Pro | Val | Gly | Asn | |
| 110 | | | | | 115 | | | | | 120 | | | | | 125 | |
| CTG | TCC | ATC | GTG | AGG | ACT | AAC | CGC | GCA | GAG | ATT | CCC | ATC | GAG | TGC | CGC | 433 |
| Leu | Ser | Ile | Val | Arg | Thr | Asn | Arg | Ala | Glu | Ile | Pro | Ile | Glu | Cys | Arg | |
| | | | | 130 | | | | | 135 | | | | | 140 | | |
| TAC | CCC | AGG | CAG | GGC | AAT | GTG | AGC | AGC | CAG | GCC | ATC | CTG | CCC | ACC | TGG | 481 |
| Tyr | Pro | Arg | Gln | Gly | Asn | Val | Ser | Ser | Gln | Ala | Ile | Leu | Pro | Thr | Trp | |
| | | | | 145 | | | | | 150 | | | | | 155 | | |
| TTG | CCC | TTC | AGG | ACC | ACG | GTG | TTC | TCA | GAG | GAG | AAG | CTG | ACT | TTC | TCT | 529 |
| Leu | Pro | Phe | Arg | Thr | Thr | Val | Phe | Ser | Glu | Glu | Lys | Leu | Thr | Phe | Ser | |
| | | 160 | | | | | 165 | | | | | 170 | | | | |
| CTG | CGT | CTG | ATG | GAG | GAG | AAC | TGG | AAC | GCT | GAG | AAG | AGG | TCC | CCC | ACC | 577 |
| Leu | Arg | Leu | Met | Glu | Glu | Asn | Trp | Asn | Ala | Glu | Lys | Arg | Ser | Pro | Thr | |
| | 175 | | | | | 180 | | | | | 185 | | | | | |
| TTC | CAC | CTG | GGA | GAT | GCA | GCC | CAC | CTC | CAG | GCA | GAA | ATC | CAC | ACT | GGC | 625 |
| Phe | His | Leu | Gly | Asp | Ala | Ala | His | Leu | Gln | Ala | Glu | Ile | His | Thr | Gly | |
| 190 | | | | | 195 | | | | | 200 | | | | | 205 | |
| AGC | CAC | GTG | CCA | CTG | CGG | TTG | TTT | GTG | GAC | CAC | TGC | GTG | GCC | ACA | CCG | 673 |
| Ser | His | Val | Pro | Leu | Arg | Leu | Phe | Val | Asp | His | Cys | Val | Ala | Thr | Pro | |
| | | | | 210 | | | | | 215 | | | | | 220 | | |
| ACA | CCA | GAC | CAG | AAT | GCC | TCC | CCT | TAT | CAC | ACC | ATC | GTG | GAC | TTC | CAT | 721 |
| Thr | Pro | Asp | Gln | Asn | Ala | Ser | Pro | Tyr | His | Thr | Ile | Val | Asp | Phe | His | |
| | | | | 225 | | | | | 230 | | | | | 235 | | |
| GGC | TGT | CTT | GTC | GAC | GGT | CTC | ACT | GAT | GCC | TCT | TCT | GCA | TTC | AAA | GTT | 769 |
| Gly | Cys | Leu | Val | Asp | Gly | Leu | Thr | Asp | Ala | Ser | Ser | Ala | Phe | Lys | Val | |
| | | | 240 | | | | | 245 | | | | | 250 | | | |
| CCT | CGA | CCC | GGG | CCA | GAT | ACA | CTC | CAG | TTC | ACA | GTG | GAT | GTC | TTC | CAC | 817 |
| Pro | Arg | Pro | Gly | Pro | Asp | Thr | Leu | Gln | Phe | Thr | Val | Asp | Val | Phe | His | |
| | | 255 | | | | | 260 | | | | | 265 | | | | |
| TTT | GCT | AAT | GAC | TCC | AGA | AAC | ATG | ATA | TAC | ATC | ACC | TGC | CAC | CTG | AAG | 865 |
| Phe | Ala | Asn | Asp | Ser | Arg | Asn | Met | Ile | Tyr | Ile | Thr | Cys | His | Leu | Lys | |
| 270 | | | | | 275 | | | | | 280 | | | | | 285 | |
| GTC | ACC | CTA | GCT | GAG | CAG | GAC | CCA | GAT | GAA | CTC | AAC | AAG | GCC | TGT | TCC | 913 |
| Val | Thr | Leu | Ala | Glu | Gln | Asp | Pro | Asp | Glu | Leu | Asn | Lys | Ala | Cys | Ser | |
| | | | | 290 | | | | | 295 | | | | | 300 | | |
| TTC | AGC | AAG | CCT | TCC | AAC | AGC | TGG | TTC | CCA | GTG | GAA | GGC | CCG | GCT | GAC | 961 |
| Phe | Ser | Lys | Pro | Ser | Asn | Ser | Trp | Phe | Pro | Val | Glu | Gly | Pro | Ala | Asp | |
| | | | 305 | | | | | 310 | | | | | 315 | | | |
| ATC | TGT | CAA | TGC | TGT | AAC | AAA | GGT | GAC | TGT | GGC | ACT | CCA | AGC | CAT | TCC | 1009 |
| Ile | Cys | Gln | Cys | Cys | Asn | Lys | Gly | Asp | Cys | Gly | Thr | Pro | Ser | His | Ser | |
| | | 320 | | | | | 325 | | | | | 330 | | | | |

```
AGG AGG CAG CCT CAT GTC ATG AGC CAG TGG TCC AGG TCT GCT TCC CGT          1057
Arg Arg Gln Pro His Val Met Ser Gln Trp Ser Arg Ser Ala Ser Arg
335                 340                 345

AAC CGC AGG CAT GTG ACA GAA GAA GCA GAT GTC ACC GTG GGG CCA CTG          1105
Asn Arg Arg His Val Thr Glu Glu Ala Asp Val Thr Val Gly Pro Leu
350                 355                 360                 365

ATC TTC CTG GAC AGG AGG GGT GAC CAT GAA GTA GAG CAG TGG GCT TTG          1153
Ile Phe Leu Asp Arg Arg Gly Asp His Glu Val Glu Gln Trp Ala Leu
                370                 375                 380

CCT TCT GAC ACC TCA GTG GTG CTG CTG GGC GTA GGC CTG GCT GTG GTG          1201
Pro Ser Asp Thr Ser Val Val Leu Leu Gly Val Gly Leu Ala Val Val
            385                 390                 395

GTG TCC CTG ACT CTG ACT GCT GTT ATC CTG GTT CTC ACC AGG AGG TGT          1249
Val Ser Leu Thr Leu Thr Ala Val Ile Leu Val Leu Thr Arg Arg Cys
        400                 405                 410

CGC ACT GCC TCC CAC CCT GTG TCT GCT TCC GAA TAAAAGAAGA AAGCAAT           1299
Arg Thr Ala Ser His Pro Val Ser Ala Ser Glu
    415                 420
```

(2) INFORMATION FOR SEQ ID NO:61:

(i) SEQUENCE CHARACTERISTICS:
        (A) LENGTH: 424 amino acids
        (B) TYPE: amino acid
        (D) TOPOLOGY: linear (ii) MOLECULE TYPE: protein
        (A) DESCRIPTION: /desc =
            "deduced amino acid sequence of human ZPC"

(xi) SEQUENCE DESCRIPTION: SEQ ID NO:61:

```
Met Glu Leu Ser Tyr Arg Leu Phe Ile Cys Leu Leu Leu Trp Gly Ser
1               5                   10                  15

Thr Glu Leu Cys Tyr Pro Gln Pro Leu Trp Leu Leu Gln Gly Gly Ala
            20                  25                  30

Ser His Pro Glu Thr Ser Val Gln Pro Val Leu Val Glu Cys Gln Glu
        35                  40                  45

Ala Thr Leu Met Val Met Val Ser Lys Asp Leu Phe Gly Thr Gly Lys
    50                  55                  60

Leu Ile Arg Ala Ala Asp Leu Thr Leu Gly Pro Glu Ala Cys Glu Pro
65                  70                  75                  80

Leu Val Ser Met Asp Thr Glu Asp Val Val Arg Phe Glu Val Gly Leu
                85                  90                  95

His Glu Cys Gly Asn Ser Met Gln Val Thr Asp Asp Ala Leu Val Tyr
            100                 105                 110

Ser Thr Phe Leu Leu His Asp Pro Arg Pro Val Gly Asn Leu Ser Ile
        115                 120                 125

Val Arg Thr Asn Arg Ala Glu Ile Pro Ile Glu Cys Arg Tyr Pro Arg
    130                 135                 140

Gln Gly Asn Val Ser Ser Gln Ala Ile Leu Pro Thr Trp Leu Pro Phe
145                 150                 155                 160

Arg Thr Thr Val Phe Ser Glu Glu Lys Leu Thr Phe Ser Leu Arg Leu
                165                 170                 175

Met Glu Glu Asn Trp Asn Ala Glu Lys Arg Ser Pro Thr Phe His Leu
            180                 185                 190

Gly Asp Ala Ala His Leu Gln Ala Glu Ile His Thr Gly Ser His Val
        195                 200                 205

Pro Leu Arg Leu Phe Val Asp His Cys Val Ala Thr Pro Thr Pro Asp
    210                 215                 220
```

-continued

```
Gln Asn Ala Ser Pro Tyr His Thr Ile Val Asp Phe His Gly Cys Leu
225                 230                 235                 240

Val Asp Gly Leu Thr Asp Ala Ser Ser Ala Phe Lys Val Pro Arg Pro
                245                 250                 255

Gly Pro Asp Thr Leu Gln Phe Thr Val Asp Val Phe His Phe Ala Asn
            260                 265                 270

Asp Ser Arg Asn Met Ile Tyr Ile Thr Cys His Leu Lys Val Thr Leu
        275                 280                 285

Ala Glu Gln Asp Pro Asp Glu Leu Asn Lys Ala Cys Ser Phe Ser Lys
    290                 295                 300

Pro Ser Asn Ser Trp Phe Pro Val Glu Gly Pro Ala Asp Ile Cys Gln
305                 310                 315                 320

Cys Cys Asn Lys Gly Asp Cys Gly Thr Pro Ser His Ser Arg Arg Gln
                325                 330                 335

Pro His Val Met Ser Gln Trp Ser Arg Ser Ala Ser Arg Asn Arg Arg
            340                 345                 350

His Val Thr Glu Glu Ala Asp Val Thr Val Gly Pro Leu Ile Phe Leu
        355                 360                 365

Asp Arg Arg Gly Asp His Glu Val Glu Gln Trp Ala Leu Pro Ser Asp
    370                 375                 380

Thr Ser Val Val Leu Leu Gly Val Gly Leu Ala Val Val Val Ser Leu
385                 390                 395                 400

Thr Leu Thr Ala Val Ile Leu Val Leu Thr Arg Arg Cys Arg Thr Ala
                405                 410                 415

Ser His Pro Val Ser Ala Ser Glu
            420
```